US009566353B2

(12) United States Patent
Markiv et al.

(10) Patent No.: US 9,566,353 B2
(45) Date of Patent: Feb. 14, 2017

(54) FLUORESCENT FUSION POLYPEPTIDES AND METHODS OF USE

(71) Applicants: Anatoliy Markiv, Middlesex (GB); Ravi Venkata Durvasula, Albuquerque, NM (US); Angray Singh Kang, Leyton (GB)

(72) Inventors: Anatoliy Markiv, Middlesex (GB); Ravi Venkata Durvasula, Albuquerque, NM (US); Angray Singh Kang, Leyton (GB)

(73) Assignee: STC.UNM, Albuquerque, NM (US)

( * ) Notice: Subject to any disclaimer, the term of this patent is extended or adjusted under 35 U.S.C. 154(b) by 44 days.

(21) Appl. No.: 14/496,605

(22) Filed: Sep. 25, 2014

(65) Prior Publication Data

US 2015/0110720 A1 Apr. 23, 2015

Related U.S. Application Data

(62) Division of application No. 13/096,695, filed on Apr. 28, 2011, now Pat. No. 8,877,898.

(60) Provisional application No. 61/343,627, filed on Apr. 30, 2010.

(51) Int. Cl.
| | |
|---|---|
| *G01N 33/53* | (2006.01) |
| *G01N 33/58* | (2006.01) |
| *C07K 16/00* | (2006.01) |
| *A61N 5/06* | (2006.01) |
| *A61K 49/00* | (2006.01) |
| *C07K 14/00* | (2006.01) |
| *C07K 16/30* | (2006.01) |
| *C07K 16/32* | (2006.01) |
| *C12Q 1/04* | (2006.01) |
| *C07K 16/18* | (2006.01) |

(52) U.S. Cl.
CPC ....... *A61K 49/0045* (2013.01); *A61K 49/0058* (2013.01); *A61N 5/062* (2013.01); *C07K 14/001* (2013.01); *C07K 16/18* (2013.01); *C07K 16/30* (2013.01); *C07K 16/32* (2013.01); *C12Q 1/04* (2013.01); *G01N 33/53* (2013.01); *G01N 33/582* (2013.01); *C07K 2317/62* (2013.01); *C07K 2317/622* (2013.01); *C07K 2319/00* (2013.01); *C07K 2319/60* (2013.01)

(58) Field of Classification Search
CPC A61K 49/0045; A61K 49/0058; C07K 16/00; C07K 16/30; C07K 16/32; C07K 17/00; C07K 16/18; C07K 2317/62; C07K 2317/622; C07K 2319/00; C07K 2319/60; G01N 33/53; G01N 33/533; G01N 33/582; A61N 5/062
See application file for complete search history.

(56) References Cited

U.S. PATENT DOCUMENTS

| | | |
|---|---|---|
| 5,196,193 A | 3/1993 | Carroll |
| 5,661,040 A | 8/1997 | Huff et al. |
| 7,005,511 B2 | 2/2006 | Tsien et al. |
| 8,877,898 B2 | 11/2014 | Markiv et al. |
| 2003/0059835 A1 | 3/2003 | Tsien et al. |
| 2007/0244298 A1 | 10/2007 | Glick et al. |
| 2007/0265430 A1 | 11/2007 | Geiger et al. |
| 2008/0188007 A1 | 8/2008 | Morrow et al. |

FOREIGN PATENT DOCUMENTS

| | | |
|---|---|---|
| WO | 2008/085987 A2 | 1/2008 |
| WO | 2009/107129 A1 | 9/2009 |

OTHER PUBLICATIONS

Jubala et al., Vet Pathol 42: 468-476, 2005.*
Almeida et al. Transmission of *Xylella fastidiosa* to Grapevines by *Homalodisca coagulata* (Hemiptera: Cicadellidae). 2003. *J Econ Entomol*. 96:264-271.
Abedi et al. "Green fluorescent protein as a scaffold for intracellular presentation of peptide". 1998. *Nucleic Acids Res*. 26(2):623-630.
Arai et al. "Fluorolabeling of antibody variable domains with green fluorescent protein variants: application to an energy transfer-based homogeneous immunoassay". 2000. *Protein Engineering*. 13(5):369-376.
Bertani. Guest Commentary. "Lysogeny at Mid-Twentieth Century: P1, P2, and Other Experimental Systems". 2004. *J Bacteriol*. 186(3):595-600.
Bradford. "A Rapid and Sensitive Method for the Quantitation of Microgram Quantities of Protein Utilizing the Principle of Protein-Dye Binding".1976. *Anal Biochem*. 72:248-254.
Brady et al. "Crystallization and Preliminary X-ray Diffraction Study of a Chimaeric Fab' Fragment of Antibody Binding Tumour Cells". 1991. *J Mol. Biol*. 219(4):603-604.
Campbell et al. "A monomeric red fluorescent protein". 2002. *Proc Natl Acad Sci USA*. 99(12):7877-7882.
Casey et al. "Green fluorescent antibodies: novel in vitro tools", 2000. *Protein Engineering*. 13(6):445-452.
Cho et al. "Structure of the extracellular region of HER2 alone and in complex with the Herceptin Fab". 2003. *Nature*. 421(6924):756-760.
Extended Search Report (8 pgs), issued on Oct. 2, 2013. International Application No. PCT/US2011/034330, filed Apr. 28, 2011.
Griep et al. "Fluobodies: green fluorescent single-chain FV fusion proteins". 1999. *J Immunol Methods*. 230(1-2):121-130.

(Continued)

*Primary Examiner* — Phuong Huynh
(74) *Attorney, Agent, or Firm* — Mueting, Raasch & Gebhardt, P.A.

(57) ABSTRACT

Embodiments of the present invention provide for the facile generation of a stable recombinant fusion polypeptides with intrinsic fluorescent properties. The recombinant antibodies may be suitable for qualitative and/or quantitative immunofluorescence analysis. Generally, the fluorescent polypeptides include a fluorescent domain comprising a C-terminus and an N-terminus; a first antibody domain covalently linked to the C-terminus; and a second antibody domain covalently linked to the N-terminus.

4 Claims, 24 Drawing Sheets

(56) References Cited

OTHER PUBLICATIONS

Hamers-Casterman et al. "Naturally occurring antibodies devoid of light chains". 1993. *Nature*. 363(6428):446-448.

International Search Report (7 pgs), issued on Jan. 18, 2012. International Application No. PCT/US2011/034330, filed Apr. 28, 2011.

Khrameeva et al. "Mutants of Monomeric Red Fluorescent Protein mRFP1 at Residue 66: Structure Modeling by Molecular Dynamics and Search for Correlations with Spectral Properties". 2008. *Biochemistry (Moscow)*. 73(10):1085-1095.

Koprowski et al. "Colorectal Carcinoma Antigens Detected by Hybridoma Antibodies". 1979. *Somatic Cell Genet*. 5(6):957-972.

Lu et al. "Cloning, expression, purification, and characterizationof LC-1 ScFv with GFP tag". 2005. *J Zhejiang Univ Sci* 6B(8):832-837.

Markiv et al. "Module based antibody engineering: A novel synthetic REDantibody". 2011. *J. Immunol Methods*. 364(1-2):40-49.

Nguyen et al. "Surgery with molecular fluorescence imaging using activatable cell-penetrating peptides decreases residual cancer and improves survival". 2010. *Proc Natl. Acad Sci USA*. 107(9):4317-4322.

Pavoor et al. "Development of GFP-based biosensors possessing the binding properties of antibodies". 2009. *Proc Natl Acad Sci USA*. 106(29):11895-11900.

Prichard et al. "Informatics Tools for Quality in Anatomic Pathology". 2008. *Clin Lab Med*. 28(2):207-222.

Serebrovskaya et al. "Targeting cancer cells by using an antireceptor antibody-photosensitizer fusion protein". 2009. *Proc Natl Acad Sci USA*. 106(23):9221-9225.

Tatiana et al. "Blast 2 Sequences, a new tool for comparing protein and nucleotide sequences". 1999. *FEMS Microbiol Letters.*, 174:247-250.

Troise et al., "Differential binding of human immunoagents and Herceptin to the ErbB2 receptor". 2008. *FEBS J*. 275:4967-4979.

Tsien. "Constructing and Exploiting the Fluorescent Protein Paintbox (Nobel Lecture) ©". 2009. *Angew Chem Int Ed Engl*. 48:5612-5626.

Worn et al. "An intrinsically stable antibody scFv fragment can tolerate the loss of both disulfide bonds and fold correctly". 1998. *FEBS Letters*. 427:357-361.

Worn et al. Review Article. "Stability Engineering of Antibody Single-chain Fv Fragments". 2001. *J. Mol Biol*. 305(5):989-1010.

Written Opinion (5 pages), issued on Jan. 18, 2012. International Application No. PCT/US2011/034330, filed Apr. 28, 2011.

Yarbrough et al. "Refined crystal structure of DsRed, a red fluorescent protein from coral, at 2.0-Å resolution". 2001. *Proc Natl Acad Sci USA*. 98(2):462-467.

Yu et al. *Investigative Ophthalmology & Visusal Science*. 49(2):522-527. Feb. 2008.

Yurchenko et al. "Ubiquitous expression of mRFP-1 in vivo by site-directed transgenesis". 2007. *Transgenic Res*. 16(1):29-40.

Zhang et al. "Reaction Progress of Chromophore Biogenesis in Green Fluorescent Protein". 2006. *J. Am Chem Soc*. 128(14):4766-4772.

Zimmer. "Green Fluorescent Protein (GFP): Applications, Structure, and Related Photophysical Behavior". 2002. *Chem Rev*. 102(3):759-781.

\* cited by examiner

Table 1. PCR primers used

| Name | Oligonucleotide sequence | Cloning site | SEQ ID NO: |
|---|---|---|---|
| RFPBamHIF | CAGTGGATCCGAGGACGTCATCAAGGAGTTC | *BamHI* | 18 |
| RFPBamHIR | CAGTGGATCCGCCTCCGCCTGTGCGGCCCTCGGGCGCGCTCGTAC | *BamHI* | 19 |
| T7F | GCAGCTAATACGACTCACTATAGG | | 20 |

*Figure 7*

```
ccatggcccaggtgcagctgcagcagagcgatgcggaactggtgaaaccgggcgcgagcgtg
       M  A  Q  V  Q  L  Q  Q  S  D  A  E  L  V  K  P  G  A  S  V
aaaattagctgcaaagcgagcggctatacctttaccgatcatgcgattcattgggcgaaa
 K  I  S  C  K  A  S  G  Y  T  F  T  D  H  A  I  H  W  A  K
cagaaaccggaacagggcctggaatggattggctatattagcccggggcaacgatgatatt
 Q  K  P  E  Q  G  L  E  W  I  G  Y  I  S  P  G  N  D  D  I
aaataTAACgaaaaatttaaaggcaaagcgaccctgaccgcggataaaagcagcagcacc
 K  Y  N  E  K  F  K  G  K  A  T  L  T  A  D  K  S  S  S  T
gcgtatatgcagctgaacagcctgaccagcgaagatagcgcggtgtattttttgcaaacgc
 A  Y  M  Q  L  N  S  L  T  S  E  D  S  A  V  Y  F  C  K  R
agctattatggccattggggccagggcaccacccctgaccgtgagcagcggcggaggcgga
 S  Y  Y  G  H  W  G  Q  G  T  T  L  T  V  S  S  G  G  G  G
tccgaggacgtcatcaaggagttcatgcgcttcaaggtgcgcatggagggctccgtgaac
 S  E  D  V  I  K  E  F  M  R  F  K  V  R  M  E  G  S  V  N
ggccacgagttcgagatcgagggcgagggcgagggccgcccctacgagggcacccagacc
 G  H  E  F  E  I  E  G  E  G  E  G  R  P  Y  E  G  T  Q  T
gccaagctgaaggtgaccaagggcggccccctgcccttcgcctgggacatcctgtcccct
 A  K  L  K  V  T  K  G  G  P  L  P  F  A  W  D  I  L  S  P
cagttccagtacggctccaaggcctacgtgaagcacccgccgacatccccgactacttg
 Q  F  Q  Y  G  S  K  A  Y  V  K  H  P  A  D  I  P  D  Y  L
aagctgtccttccccgagggcttcaagtgggagcgcgtgatgaacttcgaggacggcggc
 K  L  S  F  P  E  G  F  K  W  E  R  V  M  N  F  E  D  G  G
gtggtgaccgtgacccaggactcctccctgcaggacggcgagttcatctacaaggtgaag
 V  V  T  V  T  Q  D  S  S  L  Q  D  G  E  F  I  Y  K  V  K
ctgcgcggcaccaacttccctccgacggcccgtaatgcagaagaagaccatgggctgg
 L  R  G  T  N  F  P  S  D  G  P  V  M  Q  K  K  T  M  G  W
gaggcctccaccgagcggatgtaccccgaggacggcgccctgaagggcgagatcaagatg
 E  A  S  T  E  R  M  Y  P  E  D  G  A  L  K  G  E  I  K  M
aggctgaagctgaaggacggcggccactacgacgccgaggtcaagaccacctacatggcc
 R  L  K  L  K  D  G  G  H  Y  D  A  E  V  K  T  T  Y  M  A
aagaagcccgtgcagctgcccggcgcctacaagaccgacatcaagctggacatcacctcc
 K  K  P  V  Q  L  P  G  A  Y  K  T  D  I  K  L  D  I  T  S
cacaacgaggactacaccatcgtggaacagtacgagcgcgccgagggccgcacaggcgga
 H  N  E  D  Y  T  I  V  E  Q  Y  E  R  A  E  G  R  T  G  G
ggcggatccgatattcagatgacccagagcccggcgagcctgagcgtgagcgtgggcgaa
 G  G  S  D  I  Q  M  T  Q  S  P  A  S  L  S  V  S  V  G  E
accgtgaccattacctgccgcgcgagcgaaaacatttatagcaacctggcgtggtatcag
 T  V  T  I  T  C  R  A  S  E  N  I  Y  S  N  L  A  W  Y  Q
cagaaacagggcaaaagcccgcagctgctggtgtatgcggcgaccaacctggcggatggc
 Q  K  Q  G  K  S  P  Q  L  L  V  Y  A  A  T  N  L  A  D  G
gtgccgagccgctttagcggcagcggcagcggcacccagtatagcctgaaaattaacagc
 V  P  S  R  F  S  G  S  G  S  G  T  Q  Y  S  L  K  I  N  S
ctgcagagcgaagattttggcagctattattgccagcacttttggggcaccccgtatacc
 L  Q  S  E  D  F  G  S  Y  Y  C  Q  H  F  W  G  T  P  Y  T
tttggcggcggcacccgcctggaaattaaacgcgcggatgcggccgcactcgagcaccac
 F  G  G  G  T  R  L  E  I  K  R  A  D  A  A  A  L  E  H  H
caccaccaccaccac
 H  H  H  H  H  H
```

*Figure 11*

```
ggatccgaggacgtcatcaaggagttcatgcgcttcaaggtgcgcatggagggctccgtg
 G   S   E   D   V   I   K   E   F   M   R   F   K   V   R   M   E   G   S   V
aacggccacgagttcgagatcgagggcgagggcgagggccgcccctacgagggcacccag
 N   G   H   E   F   E   I   E   G   E   G   E   G   R   P   Y   E   G   T   Q
accgccaagctgaaggtgaccaagggcggccccctgcccttcgcctgggacatcctgtcc
 T   A   K   L   K   V   T   K   G   G   P   L   P   F   A   W   D   I   L   S
cctcagttccagtacggctccaaggcctacgtgaagcacccgccgacatccccgactac
 P   Q   F   Q   Y   G   S   K   A   Y   V   K   H   P   A   D   I   P   D   Y
ttgaagctgtccttccccgagggcttcaagtgggagcgcgtgatgaacttcgaggacggc
 L   K   L   S   F   P   E   G   F   K   W   E   R   V   M   N   F   E   D   G
ggcgtggtgaccgtgacccaggactcctccctgcaggacggcgagttcatctacaaggtg
 G   V   V   T   V   T   Q   D   S   S   L   Q   D   G   E   F   I   Y   K   V
aagctgcgcggcaccaacttcccctccgacggccccgtaatgcagaagaagactatgggc
 K   L   R   G   T   N   F   P   S   D   G   P   V   M   Q   K   K   T   M   G
tgggaggcctccaccgagcggatgtaccccgaggacggcgccctgaagggcgagatcaag
 W   E   A   S   T   E   R   M   Y   P   E   D   G   A   L   K   G   E   I   K
atgaggctgaagctgaaggacggcggccactacgacgccgaggtcaagaccacctacatg
 M   R   L   K   L   K   D   G   G   H   Y   D   A   E   V   K   T   T   Y   M
gccaagaagcccgtgcagctgccggcgcctacaagaccgacatcaagctggacatcacc
 A   K   K   P   V   Q   L   P   G   A   Y   K   T   D   I   K   L   D   I   T
tcccacaacgaggactacaccatcgtggaacagtacgagcgcgccgagggccgcacaggc
 S   H   N   E   D   Y   T   I   V   E   Q   Y   E   R   A   E   G   R   T   G
ggaggcggatcc
 G   G   G   S
```

*Figure 12*

```
ggatccgatccgatggtgagcaaaggcgaagaactgtttaccggcgtggtgccgattctg
 G  S  D  P  M  V  S  K  G  E  E  L  F  T  G  V  V  P  I  L
gtggaactggatggcgatgtgaacggccataaatttagcgtgagcggcgaaggcgaaggc
 V  E  L  D  G  D  V  N  G  H  K  F  S  V  S  G  E  G  E  G
gatgcgacctatggcaaactgaccctgaaatttatttgcaccaccggcaaactgccggtg
 D  A  T  Y  G  K  L  T  L  K  F  I  C  T  T  G  K  L  P  V
ccgtggccgaccctggtgaccacctttggctatggcctgatgtgctttgcgcgttatccg
 P  W  P  T  L  V  T  T  F  G  Y  G  L  M  C  F  A  R  Y  P
gatcacatgaaacagcatgatttttttaaaagcgcgatgccggaaggctatgtgcaggaa
 D  H  M  K  Q  H  D  F  F  K  S  A  M  P  E  G  Y  V  Q  E
cgtaccatttttttttaaagatgatggcaactataaaacccgtgcggaagtgaaatttgaa
 R  T  I  F  F  K  D  D  G  N  Y  K  T  R  A  E  V  K  F  E
ggcgatacccTggtgaaccgtattgaactgaaaggcattgattttaaagaagatggcaac
 G  D  T  L  V  N  R  I  E  L  K  G  I  D  F  K  E  D  G  N
attctgggccataaactggaatataactataacagccataacgtgtatattatggcggat
 I  L  G  H  K  L  E  Y  N  Y  N  S  H  N  V  Y  I  M  A  D
aaacagaaaaacggcattaaagtgaactttaaaattcgtcataacattgaagatggcagc
 K  Q  K  N  G  I  K  V  N  F  K  I  R  H  N  I  E  D  G  S
gtgcagctggcggatcattatcagcagaacacccgattggcgatggcccgtgctgctg
 V  Q  L  A  D  H  Y  Q  Q  N  T  P  I  G  D  G  P  V  L  L
ccggataaccattatctgagctatcagagcgcgctgagcaaagatccgaacgaaaaacgt
 P  D  N  H  Y  L  S  Y  Q  S  A  L  S  K  D  P  N  E  K  R
gatcacatggtgctgctggaatttgtgaccgcggcgggcattaccggcggcggcggatcc
 D  H  M  V  L  L  E  F  V  T  A  A  G  I  T  G  G  G  G  S
```

*Figure 13*

```
ggatccgatccgatggtgagcaaaggcgaagaactgtttaccggcgtggtgccgattctg
 G  S  D  P  M  V  S  K  G  E  E  L  F  T  G  V  V  P  I  L
gtggaactggatggcgatgtgaacggccataaatttagcgtgagcggcgaaggcgaaggc
 V  E  L  D  G  D  V  N  G  H  K  F  S  V  S  G  E  G  E  G
gatgcgacctatggcaaactgaccctgaaatttatttgcaccaccggcaaactgccggtg
 D  A  T  Y  G  K  L  T  L  K  F  I  C  T  T  G  K  L  P  V
ccgtggccgaccctggtgaccaccctgacctggggcgtgcagtgctttgcgcgttatccg
 P  W  P  T  L  V  T  T  L  T  W  G  V  Q  C  F  A  R  Y  P
gatcacatgaaacagcatgattttttttaaaagcgcgatgccggaaggctatgtgcaggaa
 D  H  M  K  Q  H  D  F  F  K  S  A  M  P  E  G  Y  V  Q  E
cgtaccatttttttttaaagatgatggcaactataaaacccgtgcggaagtgaaatttgaa
 R  T  I  F  F  K  D  D  G  N  Y  K  T  R  E  V  K  F  E
ggcgatacccttggtgaaccgtattgaactgaaaggcattgatttttaaagaagatggcaac
 G  D  T  L  V  N  R  I  E  L  K  G  I  D  F  K  E  D  G  N
attctgggccataaactggaatataacgcgattagcgataacgtgtatattaccgcggat
 I  L  G  H  K  L  E  Y  N  A  I  S  D  N  V  Y  I  T  A  D
aaacagaaaaacggcattaaagcgaactttaaaattcgtcataacattgaagatggcagc
 K  Q  K  N  G  I  K  A  N  F  K  I  R  H  N  I  E  D  G  S
gtgcagctggcggatcattatcagcagaacacccccgattggcgatggcccggtgctgctg
 V  Q  L  A  D  H  Y  Q  Q  N  T  P  I  G  D  G  P  V  L  L
ccggataaccattatctgagcacccagagcgcgctgagcaaagatccgaacgaaaaacgt
 P  D  N  H  Y  L  S  T  Q  S  A  L  S  K  D  P  N  E  K  R
gatcacatggtgctgctggaatttgtgaccgcggcgggcattaccggcggcggcggatcc
 D  H  M  V  L  L  E  F  V  T  A  A  G  I  T  G  G  G  G  S
```

*Figure 14*

A
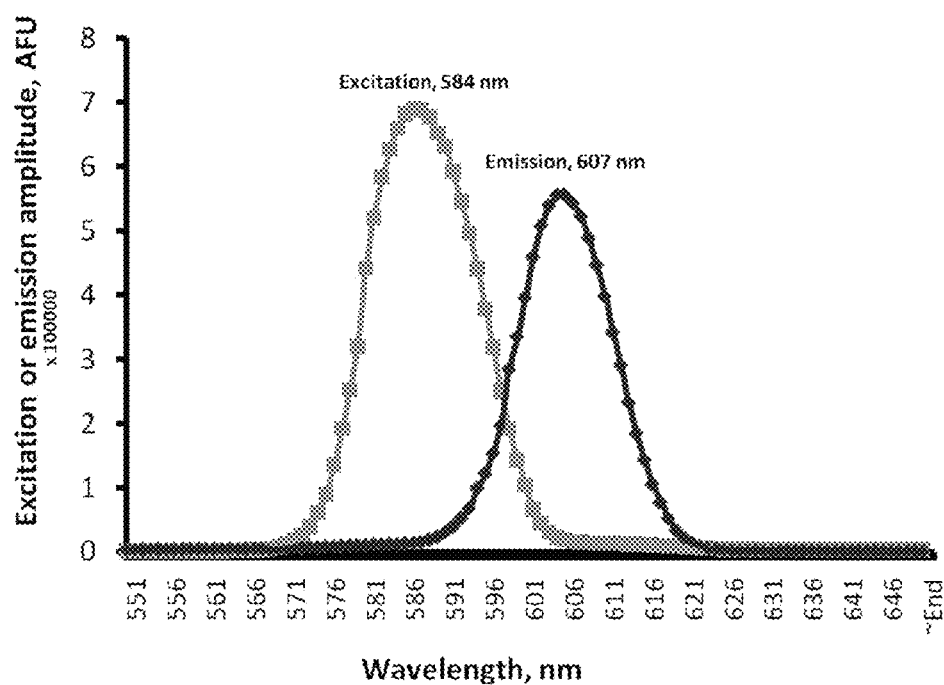
B
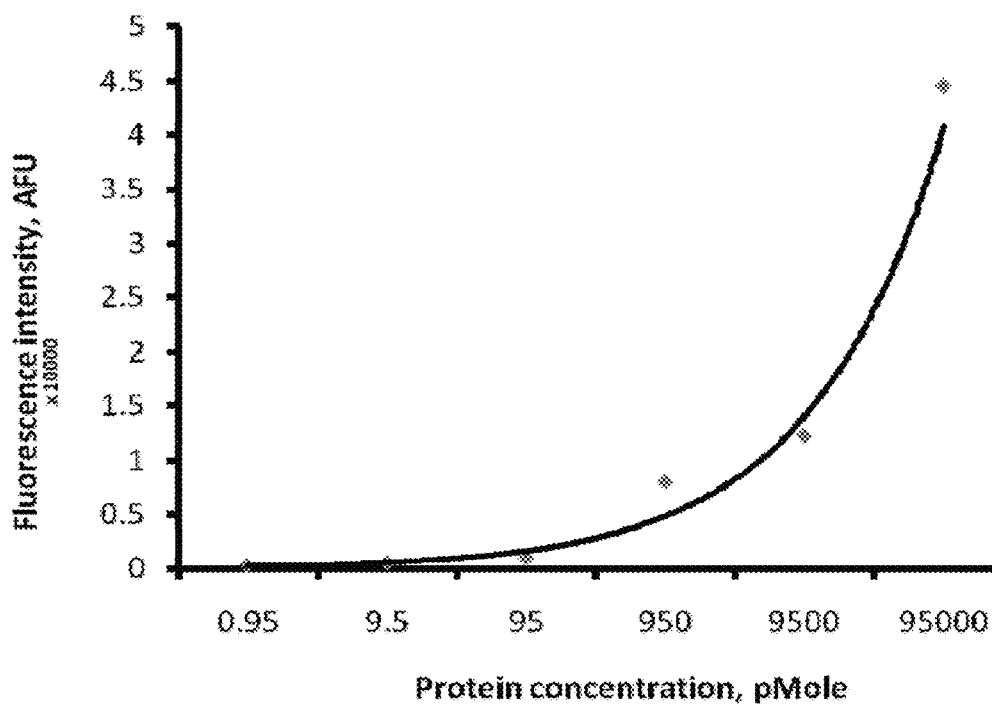
*Figure 15*

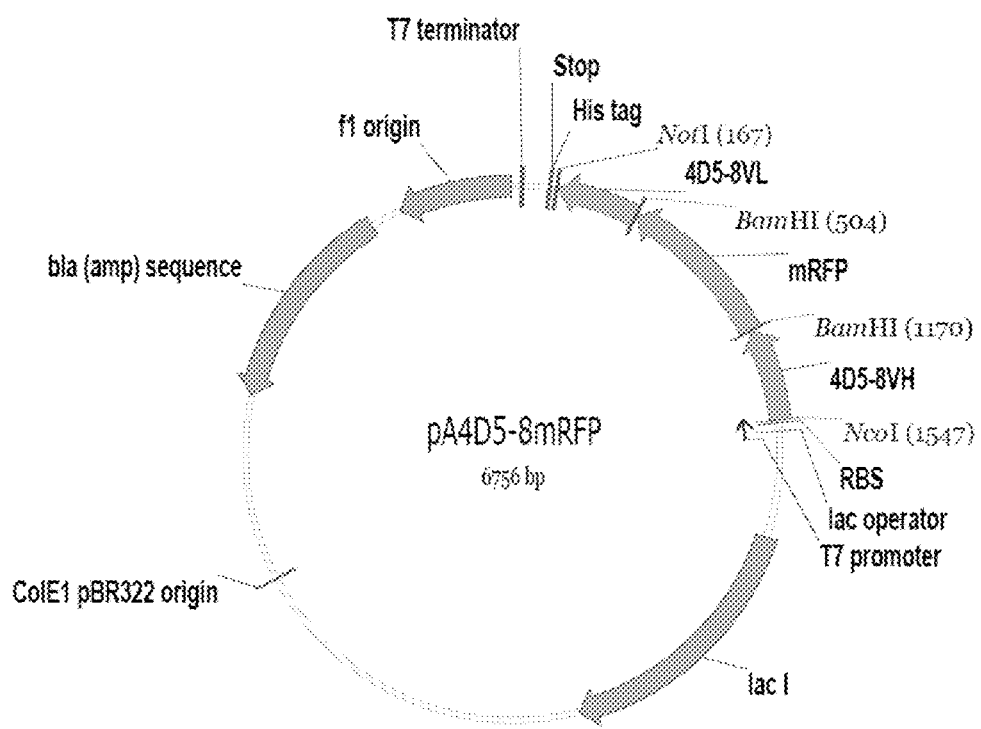
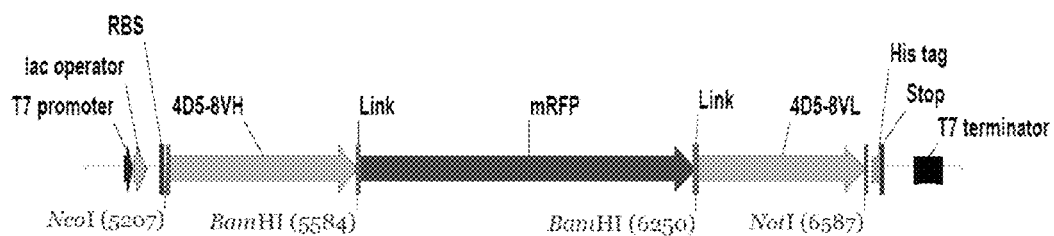
*Figure 16B*

FLUORESCENT FUSION POLYPEPTIDES AND METHODS OF USE

CROSS-REFERENCE TO RELATED APPLICATION

This application is a divisional application of U.S. patent application Ser. No. 13/096,695, filed Apr. 28, 2011, now U.S. Pat. No. 8,877,898, which claims priority to U.S. Provisional Patent Application Ser. No. 61/343,627, filed Apr. 30, 2010, each of which is hereby incorporated by reference in its entirety.

GOVERNMENT FUNDING

This invention was made with government support under R01 AI066045 awarded by the National Institutes of Health. The government has certain rights in the invention.

BACKGROUND

Nanotechnology and synthetic biology are converging areas with the potential to create novel drugs and diagnostic molecules, and to inspire a plethora of innovative applications exemplified by the advances made in the area of antibody engineering since the late 1980s. Recently efforts have been directed towards creating antibody fragments with novel effector functions as fusions with fluorescent proteins. These have used scFv fused directly to the fluorescent protein either at the C-terminus or the N-terminus, resulting in additive properties of the scFv and the fluorophore. Alternative efforts have produced a green fluorescent protein (GFP) scaffold that retains fluorophore activity and is capable of accommodating two proximal, randomized binding loops.

SUMMARY OF THE INVENTION

In one aspect, the invention provides a polypeptide that generally includes a fluorescent domain that possesses a C-terminus and an N-terminus, a first antibody domain covalently linked to the C-terminus, and a second antibody domain covalently linked to the N-terminus.

In some embodiments, at least one covalent link comprises a linker comprising no more than 10 amino acids.

In some embodiments, at least one of the fluorescent domain, the first antibody domain, or the second antibody domain comprises an affinity tag.

In some embodiments, the first antibody domain and the second antibody domain specifically bind to a single target molecule, while in other embodiments, the first antibody domain and the second antibody domain specifically bind to different target molecules.

In some embodiments, the first antibody domain comprises a variable light chain ($V_L$) comprising an N-terminus. In some embodiments, the second antibody domain comprises a variable heavy chain ($V_H$) comprising a C-terminus. In some embodiments, the polypeptide can include both a first antibody domain comprises a variable light chain ($V_L$) comprising an N-terminus and a second antibody domain comprises a variable heavy chain ($V_H$) comprising a C-terminus. In certain of these embodiments, the N-terminus of first antibody domain and C-terminus of the second antibody domain are separated by a distance of no less than 30 Å and no more than 40 Å.

In some embodiments, the fluorescent domain comprises at least a portion of a monomeric fluorescent protein sufficient to emit a fluorescent signal.

In some embodiments, the fluorescent domain comprises at least a portion of a dimeric fluorescent protein sufficient to emit a fluorescent signal.

In some embodiments, the fluorescent domain comprises an amino acid sequence comprising at least 90% amino acid sequence similarity to at least one of: amino acids 122-338 of SEQ ID NO:2, amino acids 3-219 of SEQ ID NO:4, amino acids 3-235 of SEQ ID NO:6, or amino acids 3-235 of SEQ ID NO:8.

In some embodiments, the fluorescent domain comprises an amino acid sequence comprising at least 90% amino acid sequence identity to at least one of: amino acids 122-338 of SEQ ID NO:2, amino acids 3-219 of SEQ ID NO:4, amino acids 3-235 of SEQ ID NO:6, or amino acids 3-235 of SEQ ID NO:8.

Moreover, in certain embodiments, the polypeptide can include features of any combination of two or more embodiments summarized above.

In another aspect, the invention provides a composition that generally includes two or more different fluorescent fusion polypeptides summarized above.

In some embodiments, such a composition can include a first fluorescent fusion protein that includes a first fluorescent domain and a second fluorescent fusion protein that includes a second fluorescent domain. In certain of these embodiments, the first fluorescent domain can emit a first fluorescent signal and the second fluorescent domain can emit a second fluorescent signal. In some of these embodiments, the first fluorescent signal comprises a first emission peak, the second fluorescent signal comprises a second emission peak, and the first emission peak is different than the second emission peak.

In some embodiments, a first fluorescent polypeptide specifically binds to a different target molecule than a second fluorescent fusion polypeptide.

In another aspect, the invention provides a polynucleotide that encodes any one of the polypeptides summarized above.

In another aspect, the invention provides a cell that includes such a polynucleotide.

In some embodiments, the cell can further include a second polynucleotide that encodes a second polypeptide as summarized above. In some of these embodiments, the fluorescent domain of one polypeptide can emit a first fluorescent signal comprising a first emission peak, the fluorescent domain of the second polypeptide can emit a second fluorescent signal comprising a second emission peak, and the first emission peak can be different than the second emission peak.

In another aspect, the invention provides a cell that includes any one of the polypeptides summarized above. In some of these embodiments, the cell may be a microbe, while in other embodiments, the cell may be an animal cell such as, for example, a tumor cell.

In another aspect, the invention provides a cell that includes the any one of the compositions summarized above. In some of these embodiments, the cell may be a microbe, while in other embodiments, the cell may be an animal cell such as, for example, a tumor cell.

In another aspect, the invention provides a method that generally includes introducing into a cell any one of the polynucleotides summarized above. In some of these embodiments, the cell may be a microbe, while in other embodiments, the cell may be an animal cell such as, for example, a tumor cell.

In another aspect, the invention provides a method that generally includes releasing a microbe into an environment, wherein the microbe comprises any one of the polynucleotides summarized above and at least one additional heterologous polynucleotide, and detecting the microbe by detecting the fluorescent signal. In some embodiments, the method can include detecting the fluorescent signal at a plurality of time points.

In another aspect, the invention provides a method that generally includes releasing a microbe into an environment inhabited by a pathogen, wherein the microbe include a polynucleotide summarized above that encodes a polypeptide that interferes with transmission of the pathogen, and permitting the cell to express and export the polypeptide encoded by the polynucleotide summarized above so that the polypeptide interferes with transmission of the pathogen. In some of these embodiments, the exported polypeptides binds to the pathogen. In other of these embodiments, the exported polypeptide binds to a compound produced by the pathogen. In some embodiments, the microbe is a symbiont of a host organism, which is further a host organism to the pathogen. In certain embodiments, the method can further include detecting a fluorescent signal produced by the fluorescent domain of the polypeptide encoded by the polynucleotide summarized above. In some embodiments, the method can include detecting the fluorescent signal at a plurality of time points.

In another aspect, the invention provides a method that generally includes detecting a fluorescent signal produced by cell, wherein the cell comprises a polynucleotide as summarized above that encodes a polypeptide comprising a fluorescent domain. In some embodiments, the method further includes detecting the fluorescent signal before, during, or after surgery to remove tumor cells emitting the fluorescent signal. In some embodiments, the method includes detecting the fluorescent signal at a plurality of time points. In some embodiments, the method includes exposing the cell to white light under conditions effective for the fluorescent signal to generate an amount of a reactive oxygen species effective to kill the cell.

In another aspect the invention provides a method that generally includes administering to a subject any one of the polypeptides summarized above, wherein at least one antibody domain of the polypeptide specifically binds to a marker of inflammation, and detecting a fluorescent signal produced by the fluorescent domain of the polypeptide. In some embodiments, the method includes detecting the fluorescent signal at a plurality of time points. In some embodiments, detecting the fluorescent signal may be performed non-invasively.

In another aspect, the invention provides a method that generally includes providing a sample that comprises the analyte, contacting the sample with any one or more of the polypeptides summarized above, wherein at least one antibody domain specifically binds to the analyte, removing unbound polypeptides, and detecting a fluorescent signal produced by the polypeptide specifically bound to the analyte, thereby detecting presence of the analyte in the sample. In some embodiments, the method can further include immobilizing at least a portion of the sample on a substrate. In some embodiments, the method can further include contacting at least a portion of the sample with a second polypeptide as summarized above, wherein at least one antibody domain of the second polypeptide specifically binds to the second analyte unbound removing second polypeptide, and detecting fluorescent signal produced by the second polypeptide specifically bound to the second analyte, thereby detecting presence of the second analyte in the sample. In some embodiments, the method can further include quantifying the fluorescent signal.

In another aspect, the invention provides a kit that generally includes a first container comprising a first polypeptide as summarized above comprising a first fluorescent domain that produces a fluorescent signal comprising a first emission peak, and at least one antibody domain that specifically binds to a first analyte and a second container comprising a second polypeptide as summarized above comprising a second fluorescent domain that produces a fluorescent signal comprising a second emission peak, and at least one antibody domain that specifically binds to a second analyte.

In another aspect, the invention provides a method of making a fusion polypeptide. Generally, the method includes creating an expression vector that comprises a polynucleotide operably linked to a promoter, wherein the polynucleotide encodes an fusion polypeptide comprising: a fluorescent domain comprising a C-terminus and an N-terminus, a first antibody domain covalently linked to the C-terminus, and a second antibody domain covalently linked to the N-terminus; introducing the expression vector into a host cell; and growing the host cell comprising the expression vector in conditions effective for the host cell to express the fusion polypeptide.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

FIG. 7 shows the PCR primers used in certain exemplary embodiment.

FIG. 11 shows the nucleic acid (SEQ ID NO:1) and amino acid sequence (SEQ ID NO:2) for the $V_H$, $V_L$, and fluorophore of B72.3RFP. The tertiary structure is illustrated in FIG. 1. Gray shaded amino acids correspond to the $V_H$ domain; bold text amino acids correspond to the fluorescent domain (mRFP domain); and underlined amino acids correspond to the $V_L$ domain.

FIG. 12 shows the nucleic acid (SEQ ID NO:3) and amino acid sequence (SEQ ID NO:4) of mRFP1. The fluorescent domain is reflected in amino acids 3-219 of SEQ ID NO:4.

FIG. 13 shows the nucleic acid (SEQ ID NO:5) and amino acid sequence (SEQ ID NO:6) of mCitrine. The fluorescent domain is reflected in amino acids 3-235 of SEQ ID NO:6.

FIG. 14 shows the nucleic acid (SEQ ID NO:7) and amino acid sequence (SEQ ID NO:8) of mCerulean. The fluorescent domain is reflected in amino acids 3-235 of SEQ ID NO:8.

FIG. 15: (A) Excitation and emission peaks of REDantibody 4D5-8. (B) Detection of REDantibody 4D5-8 based on concentration dependent emission at 607 nm.

FIG. 16A-E shows plasmid maps of vectors used to express 4D5-8 antibodies. Fluorescent proteins were inserted in-between the $V_H/V_L$ regions of 4D5-8. A) The plasmid map for parent plasmid pA4D5-81. B) The plasmid map and expression cassette for construct pA4D5-8mRFP. C) The plasmid map for construct pA4D5-81-mCit. D) The plasmid map for construct pA4D5-81-mCer. E) The plasmid map for construct pA4D5-81-BFP.

DETAILED DESCRIPTION OF EXEMPLARY EMBODIMENTS

Figure 1:
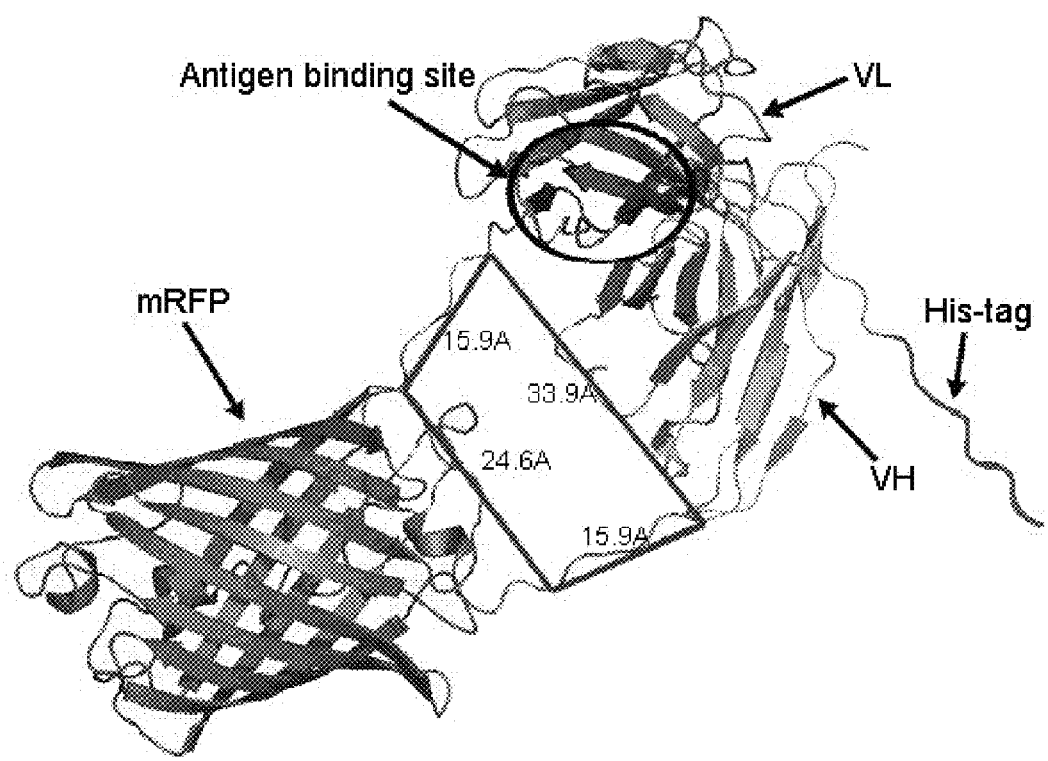
FIG. 1: Ribbon representation of a REDantibody molecule 3D model. The $V_H$ chain is shown in green, RFP domain in red, the $V_L$ chain in yellow. His-tag is shown in blue and linkers between $V_H$-RFP and RFP-$V_L$ are in cyan with the distances indicated. Antigen binding site is indicated as a black circle on antibody structure. All distances are shown as a grey lines and are indicated in the angstroms (Å).

The present invention involves novel fusion proteins constructs, polynucleotides that encode the constructs, and methods, including therapeutic, diagnostic, and detection methods, employing such constructs.

We describe herein fusion proteins that include a fluorescent protein domain linked to one or more antibody domains. In one exemplary embodiment, illustrated in FIG. 1, we used monomeric red fluorescent protein (mRFP) derived from Discosoma to link the $V_H$ and $V_L$ domain pairing of the recombinant anti-carbohydrate antibodies B72.3, CA19.9, and 4D5 anti-p185HER2.

Many antibody structures have been determined by X-ray crystallography. These analyses have revealed that the native distance between the C-terminus on the variable heavy chain and the N-terminus on the variable light chain is often approximately 35 Å. To generate conventional single chain fragment of the variable region (scFv) antibodies, a 20-30 amino acid linker may be introduced between these two sites and thus provide a flexible region of approximately 35 Å. This spacing between the $V_H$ and $V_L$ can influence the functionality of the scFv because the non-covalent interactions between $V_H/V_L$ interfaces are involved in antigen recognition. Nevertheless, the $V_H/V_L$ pairing exist in equilibrium with the unpaired state, often resulting in aggregation of the variable chains and, therefore, reduced antigen recognition and decreased stability relative to the Fab fragment or whole immunoglobulin.

We have engineered a fusion polypeptide that uses a β-barrel fluorescent domain to bridge the $V_H$ and the $V_L$ and enhance stability of the antibody domains by maintaining the correct spatial geometry between the antibody domains. Moreover, the fluorescent domain anchors the N-terminus and the C-terminus on the same plane with similar spatial dimension to the Fv in the context of a Fab fragment so that appropriate $V_H/V_L$ interface interactions may be achieved resulting in functional binding sites.

Generally, prior antibody-fluorophore conjugates have been established as valuable tools in basic and applied research, despite having limitations of photobleaching, batch variation, Fc receptor binding, aggregation, and partial loss of binding. Some of these issues can be addressed by using recombinant single-chain fragment variable antibody fused directly to genetically encoded fluorescent reporters. However, conventional single-chain fragment variable domains linked by long flexible linkers are themselves prone to disassociation and aggregation.

Here we report the design, assembly, bacterial production, and purification of a modular model that may be used generally to produce novel antibody-fluorescent protein fusion molecules. In one particular embodiment, the insertion of fluorescent protein mRFP1 in-between the $V_H/V_L$ regions of anti-p185HER2-ECD antibody 4D5-8 resulted in optimal $V_H/V_L$ interface interactions to create 4D5-8 REDantibody. The bacterially expressed monomeric molecule used in flow cytometry and cell staining studies with SKBr-3 cells retained the fluorophore properties and antibody specificity functions. The molecular model may be generalized beyond the use of mRFP1 and the 4D5-REDantibody and may, instead, use the fluorescent domain of any suitable fluorescent protein, as described in more detail below. Thus, references to REDantibody are merely an exemplary and should not be construed as limiting.

Thus, in one aspect, the invention provides a fusion polypeptide that includes a fluorescent domain comprising a C-terminus and an N-terminus, a first antibody domain covalently linked to the C-terminus, and a second antibody domain covalently linked to the N-terminus.

In some embodiments, the polypeptide can include a linker that provides the covalent linkage between the fluorescent domain and one of the antibody domains. In such embodiments, the polypeptide can include two linkers so that a linker provides the link between the fluorescent domain and each of the antibody domains. The linker may be of any suitable length. In some embodiments, the linker assists in providing the stability of the molecule by contributing to spacing between the C-terminus of one antibody domain and the N-terminus of the second antibody domain that reflects the spacing natively found in a Fab fragment or full IgG. In such embodiments, the length of the linker may be no more than 10 amino acids such as, for example, no more than nine amino acids, no more than eight amino acids, no more than seven amino acids, no more than six amino acids, no more than five amino acids, no more than four amino acids, no more then three amino acids, or no more than two amino acids. When two linkers are present, the length of one linker may be identical or different than the length of the other linker. In one embodiment, the linker can include five amino acids such as, for example, Gly-Gly-Gly-Gly-Ser_(SEQ ID NO:21).

As used herein, an antibody domain is that portion of the fusion polypeptide that exhibits affinity interaction with a ligand that is to some degree specific. As used herein, "specific" and variations thereof refer to having a differential or a non-general affinity, to any degree, for a particular target. In some embodiments, an antibody domain can include any suitable portion of an immunoglobulin. As immunoglobulin structure and function are well characterized, those of skill in the art are well equipped to determine the amount and the particular portions of an immunoglobulin necessary to provide desired target recognition. In some embodiments, an antibody domain can include, for example, a $V_L$ or a $V_H$ chain. In some of these embodiments, one antibody domain can include a $V_L$ chain while the second antibody domain can include a $V_H$ chain. In particular embodiments, a $V_L$ chain can be covalently linked to the C-terminus of the fluorescent domain and a $V_H$ chain can be covalently linked to the N-terminus of the fluorescent domain.

In some embodiments, the terminus of the antibody domains that are covalently linked to the fluorescent domain—either directly or via a linker, if present—may be separated by a predetermined distance. The minimum predetermined distance may be at least 30 Å such as, for example, at least 31 Å, at least 32 Å, at least 33 Å, at least 34 Å, at least 35 Å, at least 36 Å, at least 37 Å, at least 38 Å, or at least 39 Å. The maximum predetermined distance may be no more than 40 Å such as, for example, no more than 39 A, no more than 38 Å, no more than 37 Å, no more than 36 Å, no more than 35 Å, no more than 34 Å, no more than 33 Å, no more than 32 Å, or no more than 31 Å. The predetermined distance may be within a range defined by any minimum and any maximum distance described herein. Also, in certain embodiments, the predetermined distance may be any of the minimum or maximum endpoints described herein. Thus, the predetermined distance may be 30 Å, 31 Å, 32 Å, 33 Å, 34 Å, 35 Å, 36 Å, 37 Å, 38 Å, 39 Å, or 40 Å.

In some embodiments, the antibody domains may specifically bind to the same or to different target molecules. Thus, embodiments in which both antibody domains specifically bind to the same target molecule can be characterized as mono-specific. In contrast, a fluorescent fusion polypeptide that includes antibody domains that specifically bind to different target molecules may be characterized as bi-specific polypeptides.

The antibody domains may be, or be derived from, any suitable antibody. For example, we report herein producing a fluorescent fusion polypeptide that includes antibody domains derived from antibodies that specifically bind to human breast cancer markers (FIG. 8 through FIG. 10) as well as a fluorescent fusion polypeptide that includes antibody domains derived from antibodies that specifically bind to *T. cruzi* markers (FIG. 2 through FIG. 6). Other exemplary antibody domains can include, for example, CA125 anti-MUC16, H23 anti-MUC1 and 1C3 anti-*Plasmodium falciparum* chitinase. The modular nature of the fluorescent fusion polypeptides described herein permit great design flexibility and the possibility of exploiting the known binding affinity and specificity of any known antibody.

The fluorescent domain includes at least a portion of any suitable fluorescent polypeptide sufficient to emit a fluorescent signal. The structure and function of fluorescent polypeptides are well characterized. Thus, a person of ordinary skill in the art can readily determine the portion of a fluorescent polypeptide that is required to maintain fluorescent functionality.

In some embodiments, the fluorescent domain can optionally provide structural integrity to the molecule in addition to providing a source for the fluorescent signal. Thus, in some embodiments, the fluorescent domain can include a portion of the fluorescent polypeptide sufficient to emit a fluorescent signal and to provide desired steric stability.

In some embodiments, the fluorescent fusion polypeptide can include at least a portion of a monomeric fluorescent protein sufficient to emit a fluorescent signal. Many monomeric fluorescent polypeptides possess a β-barrel structure that is capable of maintaining a desired predetermined distance between the C-terminus of one antibody domain and the N-terminus of the second antibody domain.

Portions of certain dimeric fluorescent polypeptides also may be suitable for use as the fluorescent domain. Dimeric fluorescent polypeptides may naturally orient so that they can provide steric stability as described above while avoiding steric interference with the antigen-binding site formed by the antibody domains.

Thus, in some embodiments, the fluorescent domain can include at least a portion of mRFP, mCitrine, mCerulean, GFP(wt), EBFP, Sapphire, T-Sapphire, ECFP, mCFP, CyPet, Midori-Ishi Cyan, mTFP1, EGFP, AcGFP, TurboGFP, Emerald, Azami Green, EYFP, Topaz, Venus, yPet, PhiYFP, mBanana, Kusabira Orange, mOrange, dTomato, DsRed-Monomer, mTangerine, mStrawberry, Jred, mCherry, HcRed1, mRasberry, or mPlum. Thus, while reference is occasionally made herein to REDantibody, the use of this particular construct is merely an exemplary embodiment.

In some embodiments, the fluorescent domain can include an amino acid sequence that bears a specified level of amino acid sequence similarity to a reference polypeptide. The reference polypeptide may be, or be a fluorescently active portion of, a fluorescent polypeptide.

Amino acid similarity of two polypeptides can be determined by aligning the residues of the two polypeptides (for example, a candidate polypeptide and the fluorescent domain of, for example, any one of SEQ ID NO:2, SEQ ID NO:4, SEQ ID NO:6, or SEQ ID NO:8) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate polypeptide is the polypeptide being compared to the reference polypeptide. In some embodiments, the reference polypeptide may be, e.g., the fluorescent domain of any one of SEQ ID NO:2, SEQ ID NO:4, SEQ ID NO:6, or SEQ ID NO:8 such as, for example, amino acids 122-338 of SEQ ID NO:2, amino acids 3-219 of SEQ ID NO:4, amino acids 3-235 of SEQ ID NO:6, or amino acids 3-235 of SEQ ID NO:8.

A pair-wise comparison analysis of amino acid sequences can be carried out using the BESTFIT algorithm in the GCG package (version 10.2, Madison Wis.). Alternatively, polypeptides may be compared using the Blastp program of the BLAST 2 search algorithm, as described by Tatiana et al., (FEMS *Microbiol Lett*, 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a polypeptide of the invention may be selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH2. Likewise, biologically active analogs of a polypeptide containing deletions or additions of one or more contiguous or noncontiguous amino acids that do not eliminate a functional activity of the polypeptide are also contemplated.

The fluorescent domain can include a polypeptide with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to the reference amino acid sequence.

In certain embodiments, the fluorescent domain can include a polypeptide with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence.

In some embodiments, at least one of the fluorescent domain, the first antibody domain, or the second antibody can include an affinity tag. Affinity tags are routinely used to assist with the isolation and/or collection of recombinant polypeptides. Affinity tags, their use, and the methods of isolating polypeptides equipped with an affinity tag are well known to those of skill in the art. Exemplary affinity tags include, for example, a Histidine-rich tag (His-tag). A recombinant protein containing a His-tag can be purified and detected easily because the string of histidine residues binds to several types of immobilized metal ions such as, for example, nickel, cobalt or copper, under specific buffer conditions. In addition, anti-His-tag antibodies are commercially available for use in assay methods involving His-tagged proteins. In either case, the tag provides a means of specifically purifying or detecting the recombinant protein without a protein-specific antibody or probe. It is also possible to use alternative conventional tags including, for example, tags that include three or more amino acids, which bind to known corresponding affinity acceptors.

Another feature of the fluorescent fusion polypeptide involves the isoelectric point (pI). Table 2 summarizes the predicted pI values for exemplary antibody single chains with the predicted pI values for corresponding antibody-RFP constructs. Generally, incorporating the antibody chain into a fluorescent fusion polypeptide lowers the pI.

TABLE 2

|  | Molecular Weight | Predicted pI |
| --- | --- | --- |
| B72.3 | 26.5 kDa | 7.32 |
| B72.3-RFP | 51.5 kDa | 6.37 |
| CA19.9 | 26.4 kDa | 8.30 |
| CA19.9-RFP | 51.4 kDa | 6.54 |
| H23 | 26.2 kDa | 9.03 |
| H23-RFP | 51.2 kDa | 7.37 |
| 4D5-8 | 27.0 kDa | 8.32 |
| 4D5-8-RFP | 45.1 kDa | 6.19 |
| CA125 | 26.3 kDa | 7.86 |
| CA125-RFP | 51.3 kDa | 6.43 |

A compound can precipitate from solution when in an environment close to its pI. At physiological pH (approximately pH 7.4), the pI values of many single chain antibodies are close enough to the environmental pI that they are at risk for precipitating out of solution. Incorporating the antibody chain into a fluorescent fusion polypeptide can alter the pI so that the antibody chain is less likely to precipitate at physiological pH, thereby broadening the effective utility of the antibody chain. The $V_H$ and $V_L$ in the context of a whole antibody has a pI that is compatible with physiological pH. Once the $V_H$ and $V_L$ are engineered as single chain Fv, the pI can shift considerably resulting in a pI close to the physiological pH, this would result in the protein having a net zero charge and lead to aggregation and precipitation. We observed 4D5-8 scFv with a $(Gly_4Ser)_3$ linker with a predicted pI of 8.32 to precipitate at pH 7.4. Whereas the corresponding REDantibody 4D5-8 with a predicted pI of 6.19 was soluble at pH 7.4.

One further feature of the fluorescent fusion polypeptides described herein results from the polypeptides being able to be generated in situ. Because the polypeptides are genetically encoded, once a polynucleotide encoding the fluorescent fusion polypeptide is introduced into the cell, the cell will produce the polypeptide. Thus, intracellular target molecules can be detected without disrupting the cell to allow antibody access to these target molecules.

In some embodiments, the fluorescent domain can include a photoactivated fluorescent polypeptide. The mRFP1 (SEQ ID NO:4) is one such fluorescent polypeptide. Photoactivated fluorescent polypeptides can be regenerated by changing the light source. This can allow one to obtain repeated signal measurements from a single fluorescent fusion protein by regenerating the molecules ability to emit the fluorescent signal.

In another aspect, the invention provides compositions that include two or more fluorescent fusion polypeptide described herein. The fluorescent domain, first antibody domain, and second antibody domain of the second fluorescent fusion polypeptide can, independent of the other domains, be similar or different than the corresponding domain of any other fluorescent fusion polypeptide in the composition. Thus, a composition may include a mixture of fluorescent fusion polypeptides that may have similar or identical antibody domains so that the two different fluorescent fusion polypeptides bind to the same target molecules, but possess different fluorescent domains so that the two different fluorescent fusion polypeptides emit different fluorescent signals. Conversely, in other embodiments, a composition can include fluorescent fusion polypeptides that have different antibody domains so that the two fluorescent fusion polypeptides bind to different target molecules, but have the same fluorescent domain so that they produce the same fluorescent signal. Finally, the composition can include two entirely distinct fluorescent polypeptides so that the two fluorescent fusion polypeptides in the composition bind to different target molecules and emit different fluorescent signals.

Different fluorescent signals may be characterized in any suitable manner. For example, fluorescent signals may be characterized by the color of the signal emitted by the fluorescent domain. When more precision is desired, the fluorescent signal may be characterized in terms of the wavelength of one or more characteristic emission peaks.

In another aspect, the invention provides polynucleotides that encode any of the fluorescent fusion polypeptides described herein, and the complements of such polynucleotide sequences. Also included in the present invention are polynucleotides that hybridize, under standard hybridization conditions, to a polynucleotide that encodes any of the fluorescent fusion polypeptides described herein, and the complements of such polynucleotide sequences. Also included in the present invention are polynucleotides having a sequence identity of at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to a nucleotide sequence that encodes any of the fluorescent fusion polypeptides described herein.

As used herein, "sequence identity" refers to the identity between two polynucleotide sequences. Sequence identity is generally determined by aligning the residues of the two polynucleotides to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate sequence is the sequence being compared to a known sequence. For example, two polynucleotide sequences can be compared using the Blastn program of the BLAST 2 search algorithm, as described by Tatiana et al., FEMS Microbiol Lett., 1999; 174: 247-250, and available on the world wide web at ncbi.nlm.nih.gov/BLAST/. The default values for all BLAST 2 search parameters may be used, including reward for match=1, penalty for mismatch=−2, open gap penalty=5, extension gap penalty=2, gap x_dropoff=50, expect=10, wordsize=11, and filter on.

In another aspect, the invention provides a method that includes introducing a polynucleotide as just described into a cell. In some embodiments, the cell can be a prokaryote or a eukaryote. Thus, the cell may be a single-celled organism such as, for example, a bacterium or a yeast cell. In other embodiments, the cell may be a cell from a multicellular organism. Exemplary cells from a multicellular organism include, for example, tumor cells. The method includes introducing the polynucleotide into the cell using methods routine to those of skill in the art and appropriate for introducing foreign nucleic acid molecules into the host cell. For example, routine heat shock transformation methods may be used to introduce the polynucleotide into, for example, a bacterial cell. For mammalian cells, the polynucleotide may be introduced into the cells using, for example, nanoparticle delivery.

Thus, in yet another aspect, the invention provides a cell that includes a fluorescent fusion protein as described herein, a composition as described herein that includes one or more fluorescent fusion proteins, or a polynucleotide that encodes a fluorescent fusion protein as described herein. The cells may be in vitro—as may be the case with a tumor cell obtained through a biopsy being analyzed—or in vivo—as may be the case in methods, discussed in more detail below, in which the fluorescent fusion polypeptide is used to detect a particular cell population in situ.

In some embodiments, the method can further include detecting a fluorescent signal produced by the fluorescent domain of the fluorescent fusion polypeptide encoded by the polynucleotide and expressed by the host cell. Depending upon the cell and the nature of the antibody domains of the fluorescent fusion polypeptide encoded by the polynucleotide, methods that include detecting the fluorescent signal can have varying applications. For example, the polynucleotide may be introduced into a microbe that is further genetically modified so that, after the genetically modified microbe is released into an environment, the movement or spread of the microbe in the environment may be monitored. As such, the method can include detecting the fluorescent signal over a plurality of time points so that time course data may be obtained. As another example, the cell may be a tumor cell. The introduction of a polynucleotide that encodes a fluorescent fusion polypeptide may permit detection of tumor cells over time to, for example, monitor the metastatic activity of the tumor cells. Alternatively, the polynucleotide may be introduced into tumor cells in advance of surgery so that a surgeon is better able to distinguish diseased and healthy tissues. This can help improve the likelihood that all tumor cells are surgically removed as well as decrease the extent to which healthy cells or tissues are removed. As yet another example, the method can include non-invasive imaging; the fluorescent fusion polypeptide may be detectable non-invasively through the skin. For example, the fluorescent fusion polypeptide may be designed to detect markers of inflammation and a polynucleotide encoding that polypeptide administered to a subject. If the fluorescent domain emits a signal in the near-IR portion of the spectrum, the signal may be visible through the skin.

In some embodiments, the fluorescent fusion polypeptide may provide therapeutic activity. Fluorescence can induce the conversion of molecular hydrogen ($H_2$) and molecular oxygen ($O_2$) to hydrogen peroxide: $H_2 + O_2 \rightarrow H_2O_2$. With sufficient excitation (e.g., from white light), fluorescence from the fluorescent domain can produce enough $H_2O_2$ to kill a cell harboring the fluorescent fusion polypeptide. This feature could be exploited in conjunction with, for example, illuminating tumor cells. Expression of the fluorescent fusion polypeptide may not only help identify diseased cells, but may also provide some level of cytotoxicity.

In another aspect, one or more of the fluorescent fusion polypeptides may be used in any conventional detection method in place of an antibody with corresponding antigen recognition activity. Indeed, use of a fluorescent fusion polypeptide described herein may eliminate the final labeling step of, for example, a conventional sandwich assay.

In yet another aspect the invention provides a kit that includes, in separate containers, a first fluorescent fusion polypeptide and a second fluorescent fusion polypeptide. In other embodiments, the kits can include, in separate containers, a first polynucleotide that encodes a first fluorescent fusion polypeptide, and a second polynucleotide that encodes a second fluorescent fusion polypeptide.

In another aspect, the invention provides a method of using the fluorescent fusion polypeptide as a nanoprobe. Although immunodetection, the mainstay of clinical diagnostic laboratories has changed formats considerably over the past 50 years, the basic principles have remained fundamentally the same: i.e., antibody-antigen interaction determination, either qualitative (yes/no), if yes, where (imaging), or quantitative (how much), and various combinations of these metrics. The scope for the application of immunoassays is wide, from over-the-counter pregnancy tests, HIV testing, substance of abuse monitoring, detecting mycotoxins in food and feed, measuring markers of cardiac health to screening biopsies for tumor-associated markers. The ability to readily manipulate antibody gene sequences using simple bacterial expression systems allowed various strategies to be developed for accessing and modifying antibodies. One application of such modified antibodies involves creating recombinant antibody fragments as fusions with marker molecules. Currently, it is possible to tag antibodies with different colored fluorescent chemical tags and to use these reagents in multi-analyte detection. However, antibodies tagged in this manner can vary from batch to batch in the amount of fluorescent chemical that is conjugated to the antibody. That is, the amount of fluorescent chemical tagged to the antibody is not absolute, some may have more than others and in some instances the chemical coupling can interfere with the binding properties of the antibody. Hence, use of these tagged antibodies yields an 'averaged' result, which is acceptable for a qualitative assay, but is limited in quantitative assays.

In contrast, the fluorescent fusion polypeptides described herein include a single fluorophore so that every labeled antibody carries a single fluorescent molecule to tag antigens with a particular color. These fluorescent fusion polypeptides make possible new approaches based on the integration of multiple readouts in a range of quantitative and/or qualitative settings, from cell surfaces to antigens in microarrays, etc.

We have engineered monomeric red fluorescent protein mRFP from a coral *Discosoma* (Campbell, R. E., et al., 2002, Proc Natl Acad Sci USA 99, 7877-7882.) and inserted it between the $V_H$ and $V_L$ domains of a range of recombinant anti-cancer antibodies such as, for example, B72.3, CA19.9, and 4D5-8 replacing the flexible peptide linker. This is, however, a general approach that may be used to produce fluorescent fusion polypeptides that include a portion of $V_H$ and $V_L$ domains of any antibody of interest. Indeed, we have applied this approach successfully to six different scF$_v$s. Moreover, the mRFP can be readily interchanged with a range of other fluorescent proteins that have almost identical external tertiary structure (Tsien, R. Y., 2009, Angew Chem Int Ed Engl 48, 5612-5626), thus opening up the possibility of creating palettes of stable recombinant monoclonal antibodies with defined spectral properties for use in, for example, protein arrays, live cell imaging, and/or immunocytochemical imaging.

As noted above, in some applications, the fluorescent fusion polypeptides may be used for in vivo imaging, using the fluorescent fusion polypeptides to label, for example, diseased cells and/or tissues to aid surgery. The fluorescent fusion polypeptides may provide a navigational map to assist surgeons in identifying both diseased and healthy tissue on a molecular level and, therefore, assist in increasing the accuracy and precision of the surgical procedure to remove diseased tissue while limiting the extent to which healthy tissue is collaterally removed during surgery.

In the case of cancer, surgery with molecular fluorescence imaging using activatable cell-penetrating peptides decreased the residual cancer and improved survival in a mouse xenograft model (Nguyen, Q. T., et al., Proc Natl Acad Sci USA 107, 4317-4322). Thus, fluorescence imaging may provide a dual opportunity to exploit the fluorescent fusion polypeptides described herein. The fluorescent fusion polypeptides may be useful for detecting the presence of tumors using in vitro detection methods on cells or tissues obtained from a biopsy sample, then used in vivo for guiding the subsequent surgical removal or ablation of diseased cells and/or tissues.

In yet another aspect, fluorescent antibodies may be used in connection with pest management and/or disease control. Evolving methods for control of vector-borne diseases rely on modification of insects rather than elimination of insects by, for example, application of pesticides. These new strategies involve either direct transformation of an insect genome via mobile DNA elements (transgenesis) or expression of gene products in the host insect via transformed symbiotic microbes (paratransgenesis). Transgenesis and/or paratransgenesis may supplement conventional insect control methods and, therefore, decrease the extent to which conventional methods must be used—i.e., transgenesis and paratransgenesis may not necessarily completely supplant traditional insecticide campaigns but can decrease reliance on insecticides and, therefore, the negative environmental effects of insecticide use.

Paratransgenesis is a "Trojan Horse" approach to control of disease transmission. It employs the interactions between disease-transmitting vectors, bacterial symbionts of the vectors, and transmitted pathogens. Symbiotic bacteria are isolated and genetically transformed in vitro to export molecules that interfere with pathogen transmission. The genetically altered symbionts are then introduced into the host vector where expression of engineered molecules affects the host's ability to transmit the pathogen, i.e., its vector competence. This approach attempts to decrease pathogen transmission without adverse effects on the vectors themselves. Furthermore, it can employ, as a gene delivery mechanism, bacterial flora native to the host vector. There are several requirements for such an approach to work: (1) A population of symbiotic bacteria must exist within a given disease-transmitting vector, (2) Symbiotic bacteria should be specific to a given vector, (3) Bacterial symbionts should be amenable to culture and genetic manipulation, (4) Genetically altered symbionts should remain stable, (5) Fitness of the genetically altered symbionts to re-infect host vectors should not be compromised. Furthermore, their normal symbiotic functions should not be altered, (6) Transgene products released from the genetically altered symbionts should interact with the target pathogen(s) and (7) A method must exist for dispersal of the genetically altered symbionts amongst naturally occurring populations of vectors with minimal non-target spread of foreign genes to environmental bacteria and other arthropods.

So, for example, Pierce's Disease is a deadly disease of grapevines that causes significant economic loss to the wine industry of California. It is caused by the bacterium *Xylella fastidiosa*, which is spread by xylem-feeding sharpshooters. The predominant vector of this disease in the U.S. is the Glassy Winged Sharpshooter (GWSS), *Homalodisca vitripennis*. *Xylella* is xylem-limited in host plants and is not thought to survive outside the vector insect or host plant. GWSS is a xylem-feeder and carpets of bacteria on the surface of the precibarial chamber of the mouthparts of the insect have long been thought to be the principle source of transmission of pathogenic *Xylella* strains into susceptible plants. The anterior mouthparts of *H. vitripennis* are colonized with a variety of other environmental bacteria some of which appear to have a symbiotic association with the insect. Two such organisms are *Alcaligenes xylosoxidans dentrificans* (AXD) and *Pantoea agglomerans*, both environmental gram-negative bacteria commonly found in the *rhizosphere* of grape plants. Both *X. fastidiosa* and the two symbionts are located in physical proximity in the cibarium of GWSS in an extracellular environment. Fluorescent antibodies as described herein may be engineered into AXD and/or *P. agglomerans* so that the fluorescent antibodies are expressed, target the surface of *Xylella*, and prevent transmission of this pathogen by *H. vitripennis*. The fluorescent antibodies may provide two related but distinct functions: they can (1) function as transmission-blocking molecules that disrupt *Xylella* pathogenesis in grape plants, and (2) intrinsically fluoresce so that one can monitor gene flow in the environment as a risk assessment strategy.

To develop a panel of anti-*X. fastidiosa* surface proteins, five scFv libraries were constructed using spleens from mice previously immunized with whole, heat-inactivated *X. fastidiosa* cells. These libraries were used to select and isolate scFv's against the surface molecule MopB (4XfMopB1 & 4XfMopB3) of *X. fastidiosa*. Antibody scFv's selected against surface components of *X. fastidiosa* can be engineered into the fluorescent antibody format described herein and evaluated for plasmid-based expression in *E. coli* and *P. agglomerans*. Candidates that are expressed and secreted in *P. agglomerans* can be used to establish stable bacteria that can express the antibody using transposon insertion into the *P. agglomerans* genome.

On the outer membrane of Gram-negative bacteria, macromolecules such as lipopolysaccharides and proteins are produced. MopB is the major outer membrane protein in *X. fastidiosa*. MopB is a member of ompA protein family. Two constructs of *X. fastidiosa* MopB (truncated and full length mature) have been expressed and purified.

Furthermore, mouse immunoglobulin DNA libraries against heat-killed whole *X. fastidiosa* have been constructed and used in ribosome technology to select specific scFv antibodies against MopB and these have been characterized to confirm binding to *X. fastidiosa*. Using these libraries, one can isolate scFv antibodies against other surface proteins that may play a critical role in *X. fastidiosa* attachment or pathogenicity in the insect or plant. Since the complete genome of *X. fastidiosa* is known, using a bioinformatics approach can identify additional potential *X. fastidiosa* surface proteins. Thus, one can clone these candidates in a similar manner as MopB and use the recombinant proteins to isolate alternative surface specific scFv's.

In other approaches, paratransgenesis using a fluorescent polypeptide as described herein may be used to inhibit the effects of pathogens affecting other agricultural species, maricultural species, or livestock species. With the platform established as just described, analogous corresponding paratransgenesis systems may be designed. Such systems can permit inhibition of the pathogen and/or detection of the engineered microbe.

In another aspect, microbes may be genetically-engineered to produce and export fluorescent antibodies that interfere with animal pathogens. For example, *E. coli* Nissle (EcN) may be used as a bacterial delivery system to produce and export fluorescent antibodies that interfere with pathogenesis of, for example, *Clostridium difficile*. In this aspect, EcN are used for paratransgenesis. Resident bacteria such as, for example, EcN are isolated and genetically transformed in vitro to export molecules that interfere with pathogen transmission. The genetically altered bacteria are then introduced into the host where expression of engineered molecules disrupts virulence of the pathogen such as, for example, *C. difficile*. This approach results in a decrease of deleterious effects of the pathogen by delivering local passive immunity. Furthermore, it employs, as a gene delivery mechanism, bacterial flora that can reside in the host. This paratransgenic platform can be used to produce recombinant EcN that expresses antibodies that specifically bind *C. difficile* Toxin A and/or Toxin B.

Molecular Design

The X-ray crystallographic structure of Fab B72.3 (PDB: 1BBJ) reveals that the distance between the C-terminus Ser114 on the variable heavy chain and the N-terminus Asp1 on the variable light chain is approximately 34 Å. A search of the Protein Data Base (PDB) was carried out to identify structures with N- and C-termini in the same spatial plane with spacing close to 20-30 Å. Fortuitously, mRFP met these criteria with the distance between Val17 and His221 of the termini in fast maturing red fluorescent protein DsRed variant (PDB 2VAE) being approximately 26 Å. Thus, direct fusion of the $V_H$ to the N-terminus and $V_L$ to the C-terminus would have resulted in a linkage 8 Å shorter than the optimal spacing revealed by X-ray crystallographic structure of B72.3. This was overcome by modeling the N- and C-termini to include $Gly_4Ser$ linkers on each end of RFP (FIG. 1). The resulting model could accommodate the variable regions of the antibody with a molecular geometry approaching that determined from the X-ray studies.

Molecular Biology

The $V_H$-RFP-$V_L$-His-Tag (REDantibody) constructs were assembled in a modified pET-26b vector (EMD Chemicals Inc., Gibbstown, N.J.) with a pelB leader sequence to direct secretion to the periplasm of *E. coli* (FIG. 2A) or in a modified pET-32a vector (EMD Chemicals Inc., Gibbstown, N.J.) without a pelB leader for cytoplasmic expression. The synthetic genes of the $V_H$-$V_L$ scFv antibodies were designed to encode an in-frame BamHI site between the $V_H$ and $V_L$ regions and the whole flanked by NcoI and NotI sites for in-frame directional cloning. The mRFP gene was inserted into each of these plasmids to make expression plasmids pBAK1B72.3RFP and pBAK1CA19.9RFP as shown in FIG. 2A. The pBAK14D5RFP was assembled in a similar manner after removing an internal BamHI site. The expression cassettes starts from pelB leader sequence followed by $V_H$ chain, RFP, $V_L$ chain and an octa-His-tag at the C terminus of the resulting protein sequence as shown in FIG. 2B.

Protein Expression & Purification

Figure 3:
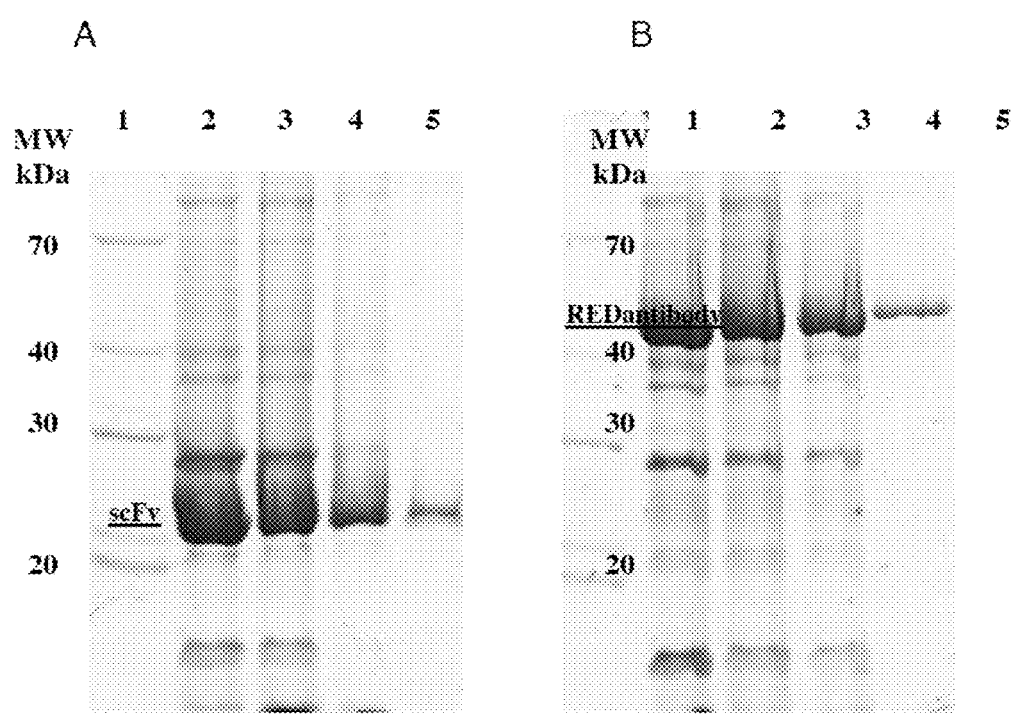
FIG. 3: Expression and purification (A) CA19.9 scFv and (B) CA19.9 REDantibody. The purified savCA19.9 (A) and REDantibodyCA19.9 (B) were resolved by 12% SUS-PAGE and stained with Coomassie Brilliant Blue R250. Lane 1: molecular weight markers, 70, 40, 30 and 20 kDa; lane 2: Ni-NTA column elution 1; lane 3: Ni-NTA column elution 2; lane 4: Ni-NTA column elution 3; lane 5: Ni-NTA column elution 4.
Figure 4:
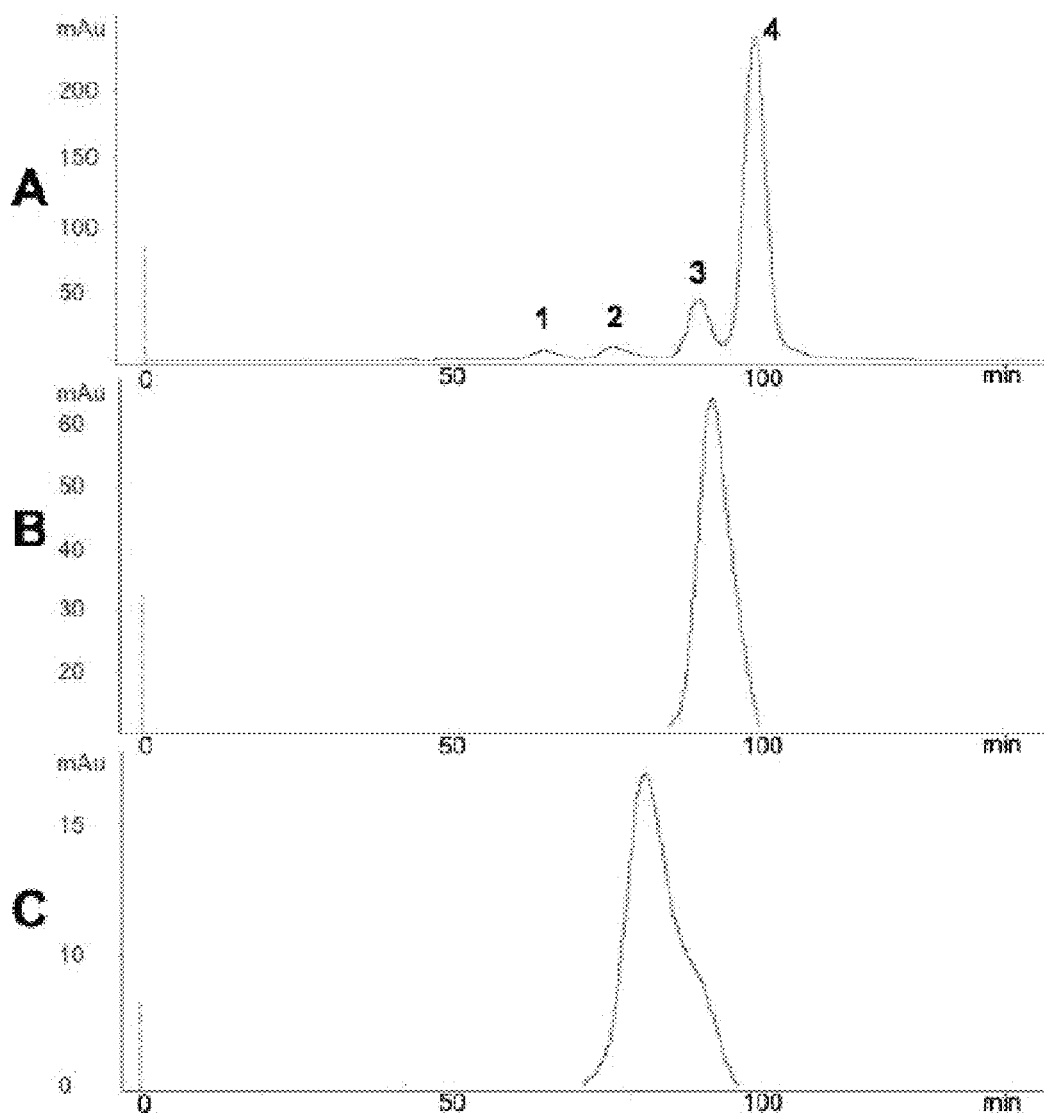
FIG. 4: Gel filtration on Sephadex G200 column. Panel A—standard proteins (peak1—200 kDa, peak 2—66 kDa, peak 3—29 kDa, peak 4—12.4 kDa); Panel B—mRFP1 and panel C REDantibodyCA19.9.
Figure 5:
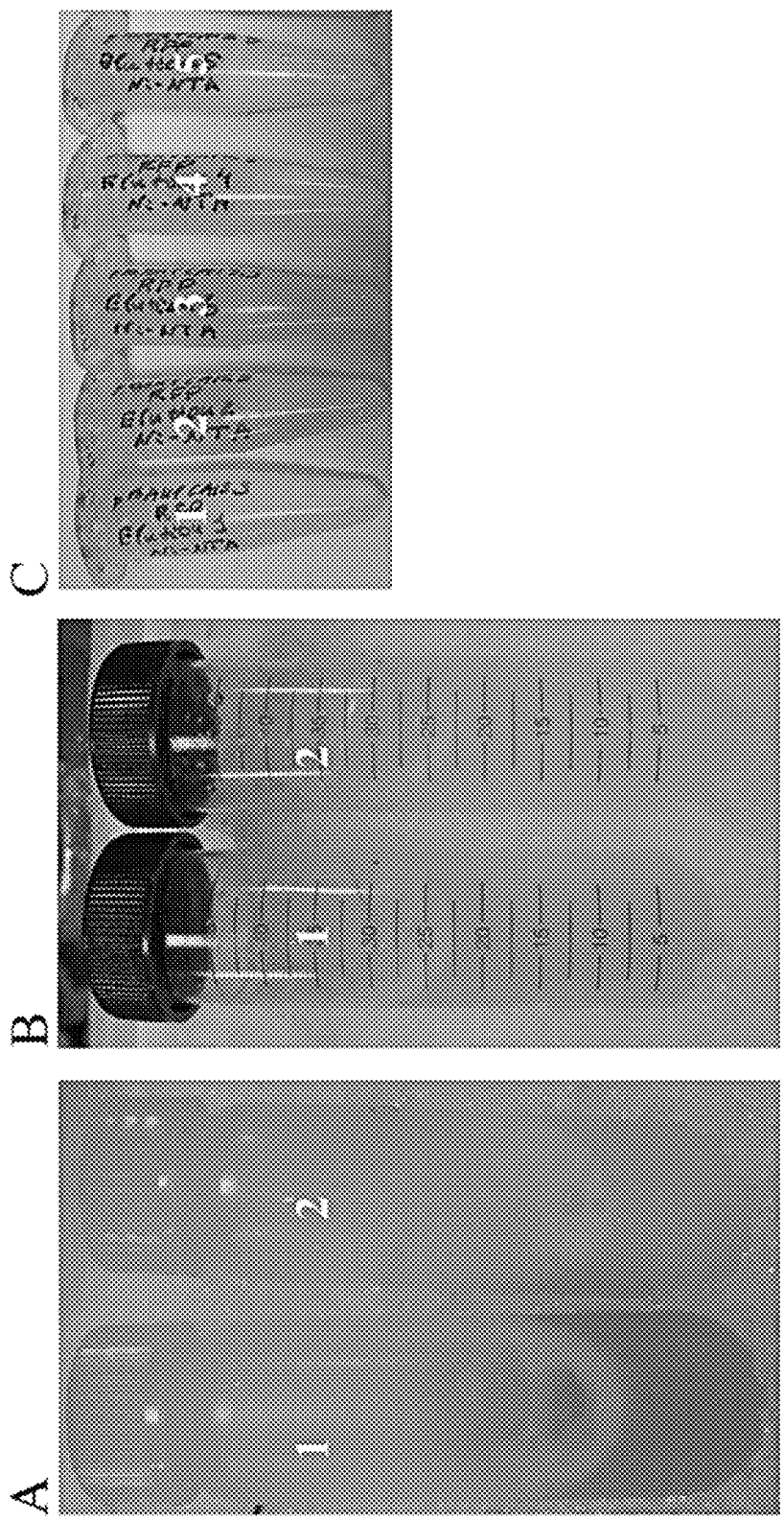
FIG. 5: REDantibody expression and purification. (A) E. coli cells expressing REDantibody (A1) and scFv (A2) resuspended in periplasmic buffer, (B) periplasmic fraction of extracted REDantibody (B1) and scFv antibody (B2) and (C) is REDantibody fractions 1-5 eluted from the Ni-NTA column and labeled as C1-05 respectively.
Figure 6:
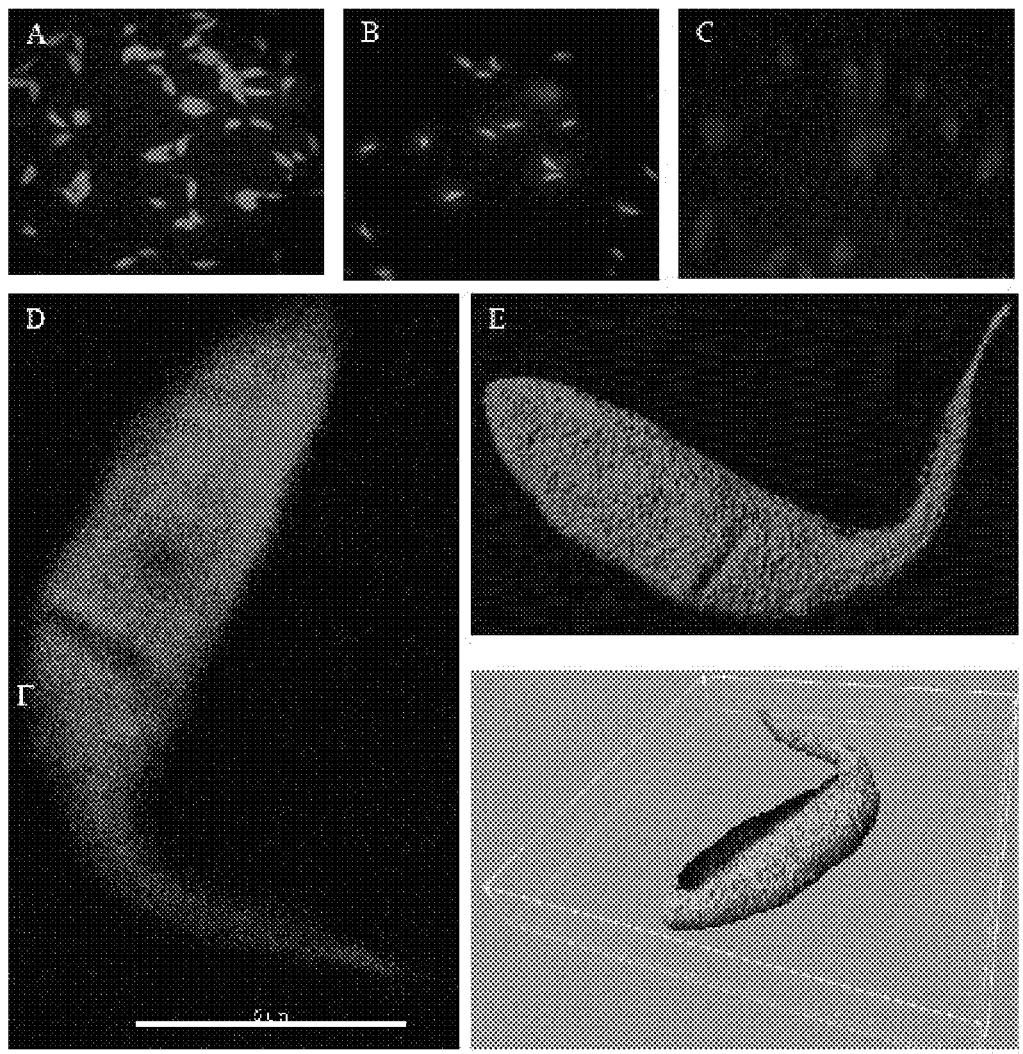
FIG. 6: Immunofluorescent microscopic analysis of T. cruzi epimastigotes stained with REDantibody CA19.9 (A), REDantibody B72.3 (B) and negative control REDantibody 4D5 (C). T. cruzi epimastigote is stained with REDantibody CA19.9 and viewed by microscopy reveals a maximum intensity fluorescent image (D). The surface staining combined with confocal microscopy reveals a slight invagination on the parasite surface (E). A cut-away of the image (E) reveals the staining is limited to the surface of the T. cruzi epimastigote (F).

The recombinant scFv and the corresponding REDantibody proteins were expressed in BL 21 (DE3) pRARE *E. coli* strain and recovered from the periplasmic extract or in Rosetta gami B(DE3) *E. coli* strain and recovered from the cytoplasmic extract and purified via Ni-NTA affinity chromatography. Protein expression and purification processes were monitored by SDS-PAGE. The protein concentration of the recovered functional protein was determined for each construct: mRFP (20 mg/L), REDantibody 4D5 (5 mg/L), REDantibody CA19.9 (0.88 mg/L), and REDantibody 72.3 (0.9 mg/L). The predicted molecular weights of the scFv and REDantibody recombinant proteins were approximately 25 kDa and 51 kDa, respectively, as shown in FIG. 3. The SDS-PAGE analysis of the Ni-NTA affinity enriched recombinant antibodies also had other protein bands corresponding to co-enriched *E. coli* host proteins. The size exclusion column was calibrated using a standard range 200 kDa-12 kDa (Sigma-Aldrich, St. Louis, Mo.) prior to use (FIG. 4A). The mRFP protein elution corresponded to monomer of 25 kDa (FIG. 4B). A single REDantibody peak eluted at fractions/time corresponding to ~51 kDa, (FIG. 4C). Moreover, the color of REDantibody *E. coli* culture, periplasmic, and elution fractions were pink (FIG. 5 A-C, respectively).

Fluorophor Measurements

The excitation and emission peaks of REDantibody 4D5-8 were determined to be 584 nm and 607 nm as shown in FIG. 15A. The concentration dependent emission at 607 nm permitted accurate detection of 9.5 pmole of this REDantibody as shown in FIG. 15B.

BIAcore Measurements

The association and disassociation rate for REDantibody 4D5-8 binding to p185HER2-ECD was determined to be $2.19 \times 10^{-4} \pm 0.13 \times 10^{-4}$ $M^{-1}s^{-1}$ and $4.43 \times 10^{-5} \pm 1.04 \times 10^{-5}$ $s^{-1}$, respectively and the KD calculated to be 2.2±0.8 nM.

Immunofluorescent Staining and Confocal Microscopy

Functional analysis of the REDantibody was based on well-characterized properties of B72.3 and CA19.9 antibodies to recognize sialyl-Tn and sialylated Lewis (Le)$^a$ blood group antigen, respectively, which are part of a panel of markers used in cancer diagnostics. The same sialyl-Tn antigen has previously been detected on the surface of the human pathogen *Trypanosoma cruzi* using B72.3 monoclonal antibody.

The CA19.9 also binds to sialyl glycans on the parasite surface. The 4D5 REDantibody was constructed for use as a negative control since it recognizes a peptide epitope on p185HER2, but not sialyl glycan. This was confirmed by the fluorescent staining of *T. cruzi* epimastigotes using purified recombinant anti-glycan REDantibody shown in FIG. 6A and FIG. 6B. The control REDantibody 4D5 did not label the parasites (FIG. 6C). The maximum intensity fluorescence staining image with REDantibody CA19.9 (FIG. 6D) revealed the appearance of a cleft area on the parasite surface with reduced staining Confocal three-dimensional imaging (FIG. 6E) confirmed the presence of a depression corresponding to the cleft observed earlier. The cut away image of the confocal image revealed that the staining was restricted to the surface of the parasite (FIG. 6F).

Immunofluorescent tagging of molecules, in particular antibodies, is a widely used tool in clinical diagnostics and research. Historically, fluorophores exemplified by FITC, TRITC/CY-3, and TRITC/CY-5 have been chemically linked to antibodies, resulting in some instances with reduced binding to target antigen and/or a heterogeneous number of labels incorporated into each antibody molecule. The heterogeneity of labels incorporated into each antibody molecule limits the utility of these molecules for quantitative analysis. Significant advances have been made in conjugation chemistry to attempt to overcome some of these difficulties. For example, approaches have been developed that result in recombinant scFv that incorporate a free cysteine at the C-terminus for specific conjugation chemistry. Others have gone one step further and fused scFv directly to GFP. However conventional scFv are prone to aggregation. It is not clear whether fusing a scFv directly to GFP would impact the aggregation properties of the scFv. More recently, GFP has been modified to incorporate two loops that can form recognition motifs even though the resulting molecule is not an antibody as such.

We sought to overcome two issues faced with creating antibody fluorophores. Firstly, we incorporated a single fluorophore per binding site. Secondly, we spatially orientated the $V_H/V_L$ interfaces for optimal pairing. Our earlier attempts to construct similar bridged molecules using a related β-barrel structure of green fluorescent protein (GFP) resulted in molecules that did not bind to the target antigen.

Figure 2:
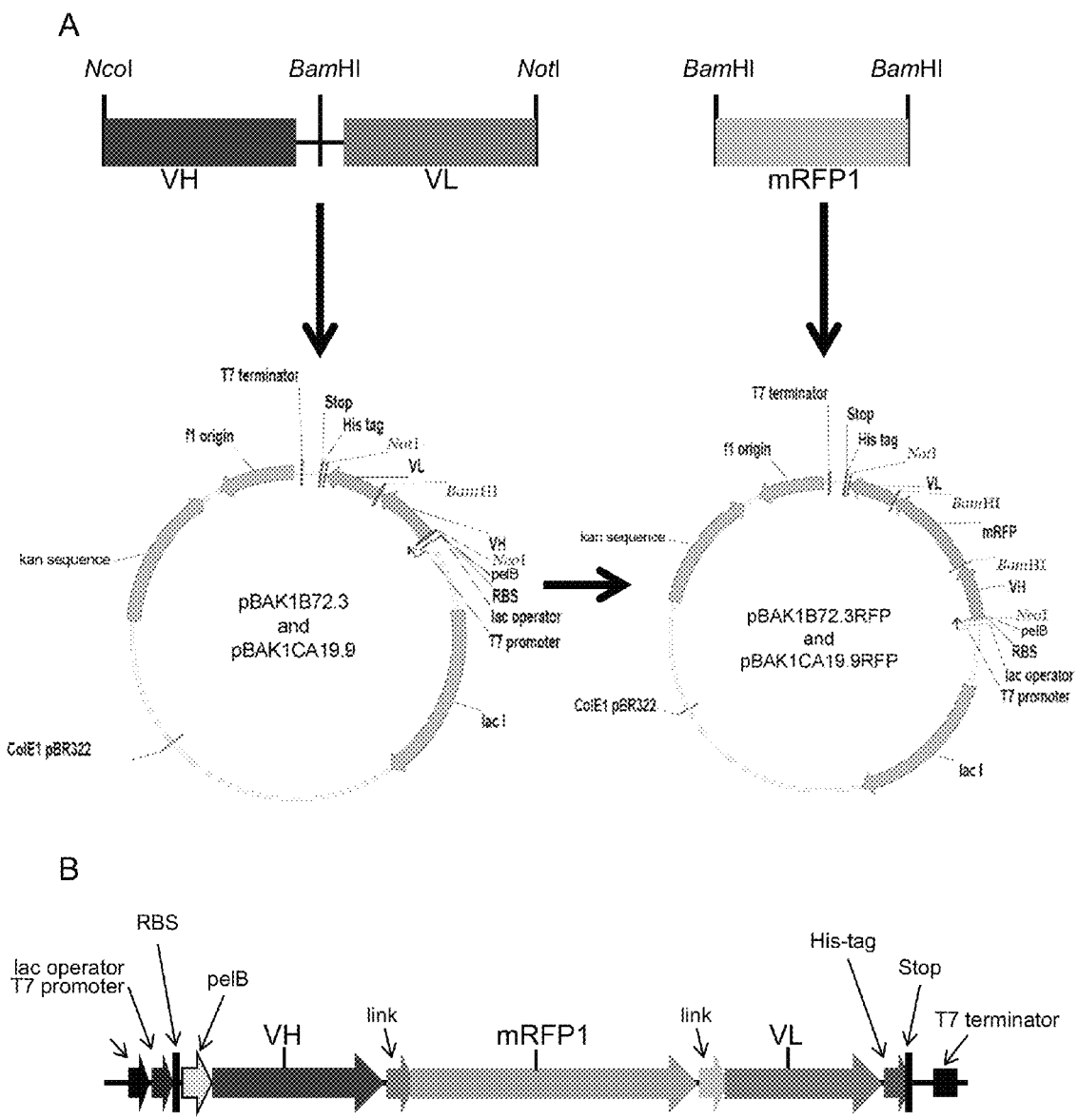
FIG. 2: Generation of expression plasmid (A) and E. coli expression cassette (B) of REDantibody. (A) The single chain Fv encoding fragment flanked by NcoI and NotI sites with an inframe BamHI site between the $V_H$ and $V_L$ was inserted into pBAK1 vector to generate pBAK1B72.3, pBAK1CA19.9 and pBAK14D5. The mRFP encoding fragment flanked by BamHI sites was inserted into the pBAK1B72.3, CA19.9 and 4D5 to generate pBAK172.3RFP, pBAK1CA19.9RFP and pBAK14D5RFP. (B) The expression cassette has a T7 promoter to initiate transcription using T7 RNA polymerase, lac operator is for the control of transcription using IPTG. RBS is ribosome binding site where translation begins, pelB sequence to guide newly synthesized molecule into the E. coli periplasm where this sequence is cleaved and disulphide bonds are formed. $V_H$ is variable heavy chain of antibody, Link is an additional 5 amino acids to flank either side of the mRFP1 gene, mRFP is a gene of red fluorescent protein and $V_L$ is variable light domain of antibody. This is followed by His-tag sequence for immobilized metal affinity purification and stop codon. T7 terminator is to terminate transcription by T7 RNA polymerase.

The vectors constructed encoding the REDantibodies are based on the pET series as shown in FIG. 2. The use of the T7 promoter and the BL21(DE3) host results in high level of expression of the recombinant protein, the majority of which is retained within the cell cytoplasm despite having a PelB leader sequence to direct the polypeptide into the periplasm. The amount of REDantibody recovered varied for each antibody construct. 4D5 had the highest recovery (5 mg/L) whereas the recovery of the corresponding anti-sialyl glycan antibodies were both just below 1 mg/L. Both levels are comparable to the recovery of scFv from *E. coli*. The recovery of anti-sialyl glycan REDantibodies may have been reduced since the secreted, correctly folded, and functional REDantibody in both cases bound to sialic acid, which is present on the host bacterial surface.

Sufficient REDantibody was recovered from the periplasmic extract to permit further affinity purification and functional analysis. The SDS-PAGE of the affinity isolated CA19.9 scFv and the corresponding REDantibody had proteins of 25 kDa and 51 kDa, respectively, as shown in FIG. 3A and FIG. 3B, respectively. The REDantibody also had a doublet band at 26 kDa, which could be due to cleavage within the mRFP that occurs when the sample is boiled in SDS as observed with DsRed.

Size exclusion chromatography on the affinity purified proteins was used to determine whether the molecules were monomeric or multimeric. Each of the mRFP and REDantibody eluted with a single peak, corresponding to 25 kDa and 51 kDa, respectively, as shown in FIG. 4B and FIG. 4C, respectively. These data indicate that both proteins are monomeric.

Features of this REDantibody platform include the intrinsic color of the bacteria producing the active molecule and the intrinsic color of the purified proteins. Consequently, sophisticated detection in the purification steps is not required. The excitation wavelength of REDantibody is 584 nm and the emission wavelength is 607 nm, which are identical to mRFP (Campbell et al., 2002 Proc Natl Acad Sci USA 99:7877-82; Khrameeva et al., 2008 Biochemistry (Mosc) 73:1085-95) confirming that the fusing immunoglobulin domains to both ends of a fluorescent protein does not compromise the fluorescent properties. Moreover, it may be possible to detect as little as 9.5 pmoles of REDantibody using a standard fluorometer as shown in FIG. 15B. This may permit quantitative analysis of target antigen. The kinetics of binding for the anti-glycan REDantibodies were difficult to perform since a defined antigen preparation was not readily available. Thus we carried out the binding studies on the REDantibody 4D5-8. The calculated $K_D$ value for REDantibody 4D5-8 of 2.19 nM was within the values determined independently for the 4D5-8 scFv with a $V_H$-(Gly4 Ser)3 linker $V_L$ orientation of 194 pM (Worn and Pluckthun, 1998 FEBS Lett 427:357-61), and 9.4 nM for HERCEPTIN (Genentech, Inc., South San Francisco, Calif.) (Troise et al., 2008 FEBS J 275:4967-79), further confirming that the binding characteristics are not compromised in this format.

These characteristics of the REDantibody permit its use with other conventional dyes for FACs analysis, immunochemistry, and confocal microscopy that utilize a range up to 543 nm. In this study we used the REDantibody B72.3 and CA19.9 to visualize the carbohydrate antigens sialylTn and sialylated Lewis (Le)a on the surface of *T. cruzi* epimastigotes, respectively, using immunofluorescence (FIG. 6A, FIG. 6B and FIG. 6D) and confocal (FIG. 6E and FIG. 6F) microscopy. The binding of the REDantibody CA19.9 is restricted to the surface of the parasite (FIG. 6B). The negative control REDantibody 4D5-8 did not label the parasites when examined using immunofluorescence microscopy, implying the specificity of binding observed using the B72.3 and CA19.9 antibodies was introduced by the antibody binding domains (FIG. 6C).

One feature of the REDantibodies described herein include robust stability; the slides prepared for this study could be viewed for at least a week without noticeable loss of signal, indicating robust stability of the REDantibody. Another feature is that the monomeric red fluorescent protein (mRFP1) derived from DsRed is stable within a wide range of pH 5.0-12.0 and in 6M urea. Thus, the antibody/antigen interaction may be disrupted by adjusting the pH and/or adding urea, and the released fluorophore may be quantified in solution. Yet another feature is that the REDantibody molecule is photo activated. Thus, the REDantibodies described herein permit detecting a target with increased sensitivity through the use of, for example, time-resolved dual laser pulsed analysis. Yet another feature is that the REDantibody can generate reactive oxygen species (e.g., $H_2O_2$) upon exposure to white light. This may potentially provide a wide range of therapeutic applications such as, for example, photo-ablation of target cells. Additionally, with a far red emission spectra, these types of molecule may have utility in in vivo whole body imaging.

Assembling the REDantibody using the fluorophore as a bridge introduces certain features. Firstly, with an integrated fluorophore, a single reagent has been created, which reduces time and cost and increases reproducibility of the binding assay. Secondly, the antibody binding site and fluorophore are stoichiometric. Thus, the signal generated is directly proportional to the amount of antibody bound (i.e., quantitative). Finally, expression and purification steps can be monitored without the need for the expensive equipment since the bacteria and the recombinant proteins are visible with a distinct red color.

The platform may be applied using other suitable fluorescent protein domains. Thus, the fluorescent domain can include at least a portion of mRFP, mCitrine, mCerulean, GFP(wt), EBFP, Sapphire, T-Sapphire, ECFP, mCFP, CyPet, Midori-Ishi Cyan, mTFP1, EGFP, AcGFP, TurboGFP, Emerald, Azami Green, EYFP, Topaz, Venus, yPet, PhiYFP, mBanana, Kusabira Orange, mOrange, dTomato, DsRed-Monomer, mTangerine, mStrawberry, Jred, mCherry, HcRed1, mRasberry, or mPlum. Thus, the preceding description of the construction of the REDantibody is merely exemplary; analogous constructs may be designed using any suitable fluorescent protein domain.

Moreover, this platform may be applied to other existing mAbs to create the next generation of diagnostic and therapeutic molecules. The platform may also be used to create libraries of $V_H$ and $V_L$ domains that may be readily accessed using high throughput non-isotopic screening and not rely on phage or other types of display selection technologies. In general, the use of other pre-folded protein domains with N- and C-termini in the same spatial plane with spacing close to 20-30 Å may be used in this modular approach to antibody engineering. Furthermore, the monomeric fluorophore also may be engineered to alter the excitation/emission spectra, thus enabling multicolored antibody-based reagents for multi-analyte detection or co-localization studies.

Figure 8A:
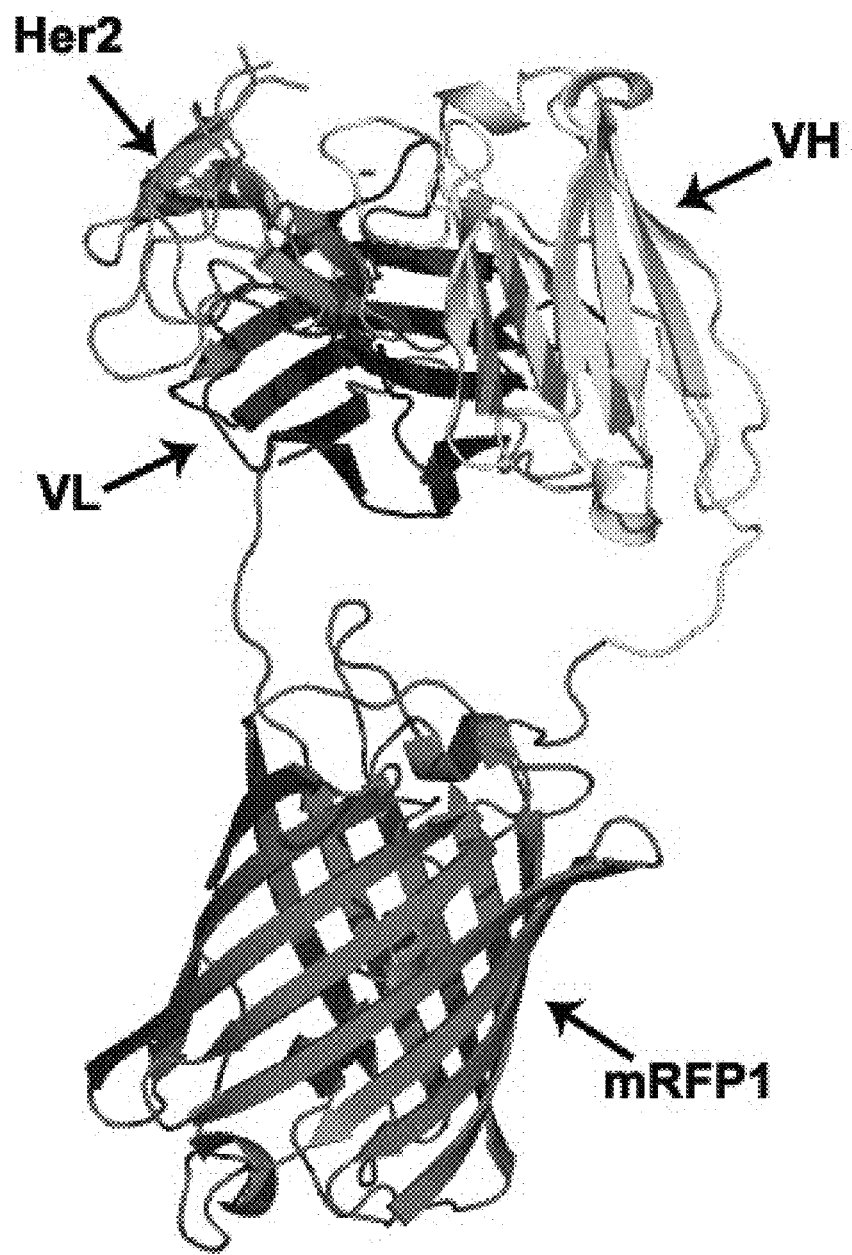
FIG. 8A-B shows plasmid maps and 3D model of genetically encoded fluorescent antibody. (A) Molecular model (ribbon representation) of the HERCEPTIN $V_H$ and $V_L$ (Genentech, Inc., South San Francisco, Calif.) antigen-binding fragment (Fv) complexed with human HER2 (PDB 1N8Z) with mRFP1 linker based on the DsRed (PDB 1G7K). A portion of HER2 is shown in orange, $V_H$ chain of 4D5-8 in green, mRFP1 in red and $V_L$ chain of 4D5-8 antibody in navy blue. (B) Plasmid maps of pBAK1 vector (FIG. 8B-1), p4D5-8Bam (FIG. 8B-1) and p4D5-8mRFP1 (FIG. 8B-2) used to clone and express red fluorescent antibody. The expression cassette has a T7 promoter region, a lac operator, a ribosome-binding site followed by a cloning region with NdeI, NcoI and NotI restriction sites for the insertion of the DNA sequences. At the end, there is a T7 termination sequence to restrict translation to the expression of RNA for the recombinant protein. The vector also has the kanamycin resistance gene, ColE1 pBR322 origin of replication and lad repressor gene. The 4D5-8mRFP1 construct starts with pelB leader sequence to direct the protein to the periplasmic space of E. coli where it is cleaved off. The mature protein begins with $V_H$ chain, followed by a 5-amino acid linker, mRFP1 sequence, second 5-amino acid linker, $V_L$ chain and terminates with an octa-His-tag.
Figure 9:
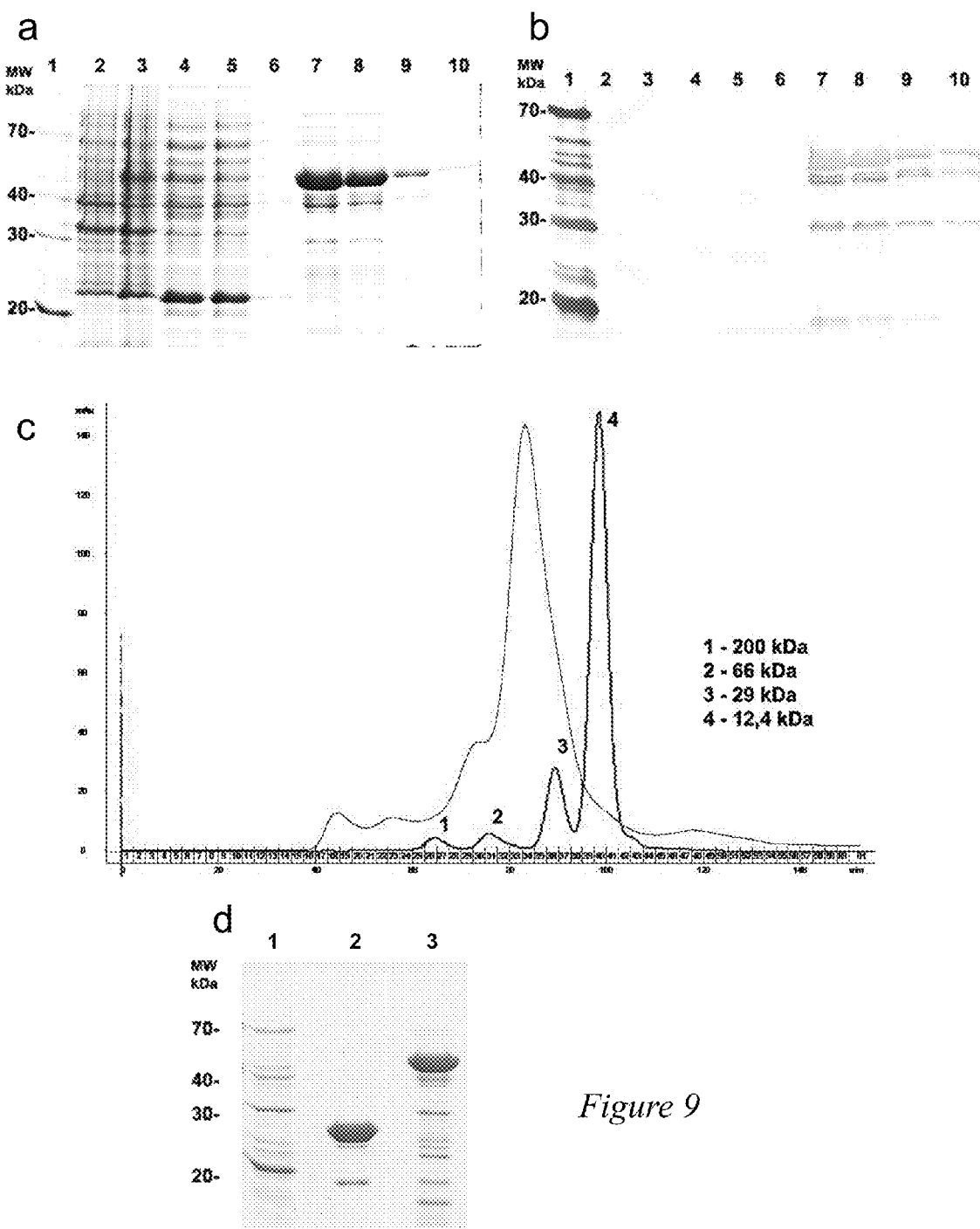
FIG. 9 shows purification and characterization of the 4D5-8mRFP1 recombinant protein. (a) SDS-PAGE and Coomassie stained gel of 4D5-8mRFP1: molecular markers (Lane 1), uninduced sample (Lane 2), IPTG induced sample (Lane 3), soluble fraction (Lane 4), flow-through $Ni^{2+}$-nitrilotriacetic acid column (Lane 5), wash fraction (Lane 6), elution fractions using 500 mM concentration imidazole (Lanes 7-10). (b) Western blotting of SDS-PAGE gel of 4D5-8mRFP1 (as in panel a) analyzed using HRP-labelled anti-His-tag antibody. (c) Gel filtration chromatography of standards proteins (peaks 1-4) and $Ni^{2+}$ nitrilotriacetic acid purified 4D5-8mRFP1 protein using Sephadex G 200 gel bead column. (d) SDS-PAGE and Coomassie stained gel of gel filtration chromatography 4D5-8mRFP1 (pooled fractions 32-37): molecular markers (Lane 1), mRFP1 (Lane 2) 4D5-8mRFP1 (Lane 3).

We engineered a scFv 4D5-8 fusion with mRFP1 based on the X-ray crystal structure of 4D5-8 Fab (PDB 1N8Z; Cho et al., 2003 Nature 421(6924):756-760) and the modeled structure of mRFP1 based on the DsRed dimer (PDB 1G7K; Yarbrough et al., 2001 Proc Natl Acad Sci USA 98(2):462-467). We fused the C-terminus of 4D5-8 $V_H$ chain to the N-terminus of mRFP1 and fused the 4D5-8 N-terminus of $V_L$ to the C-terminus of mRFP1, with the addition of optimal linkers separating both protein functions yet preserving the correct spatial dimensions for $V_H/V_L$ interaction and fluorophore activity (FIG. 8A). With the addition of five amino acid (Gly4Ser) linkers to either end of the mRFP1, the N-terminus, C-terminus, or both can readily be extended to create a distance of, for example, approximately 35 Å between the mRFP1 domain of the fusion and the $V_H/V_L$ chains. The predicted structure shows that the mRFP1 does not interfere with the scFv binding site, which is fully available to contact the target ligand. This spatial geometry permits the docking of mRFP1, or any of its derivatives, between the antibody $V_H/V_L$ or $V_L/V_H$ chains resulting in functional scFv-fluorophore fusions.

Construction of the Expression p4D5-8mRFP1 Vector.

Figures 1, 8B:
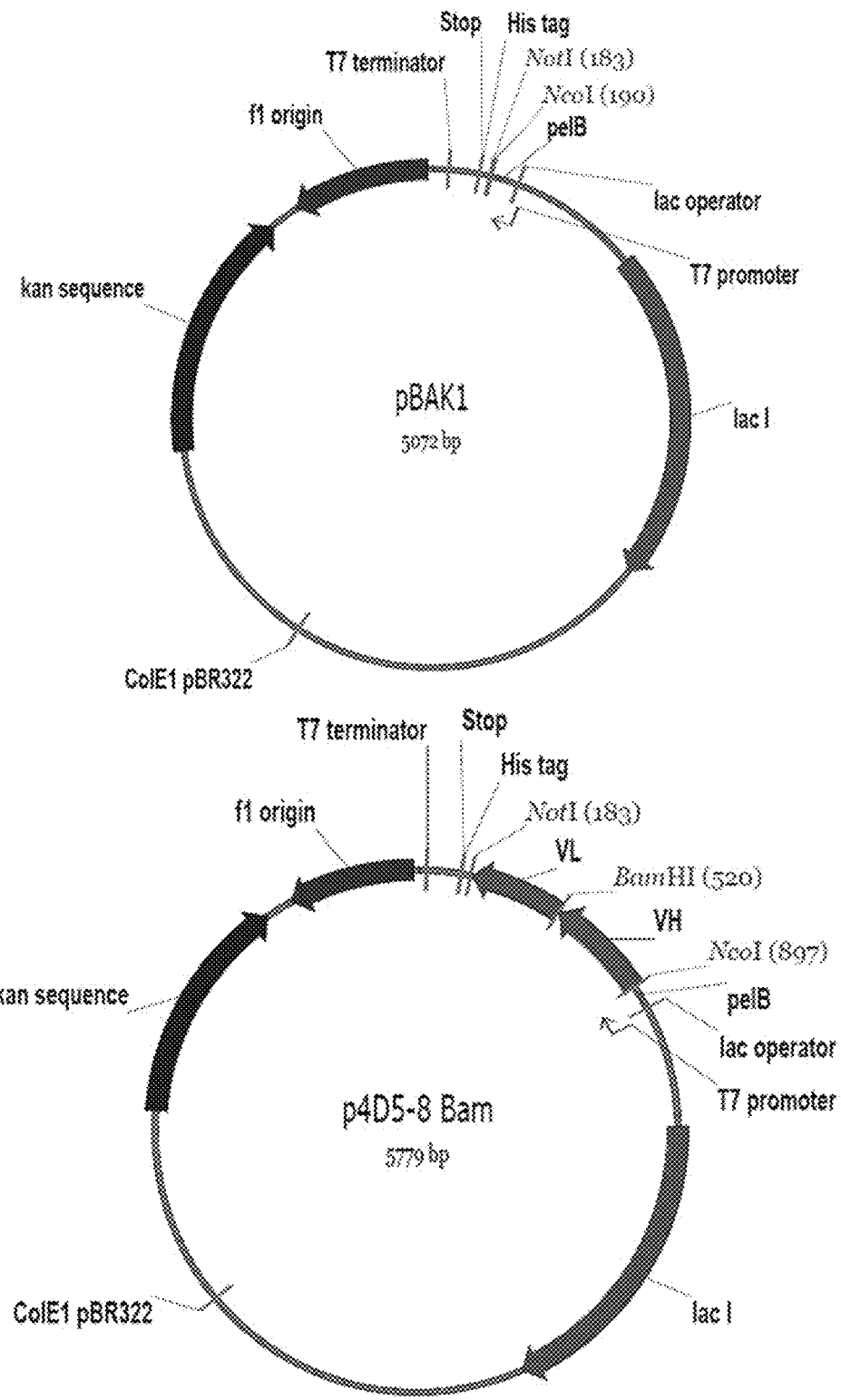
Figures 2, 8B:
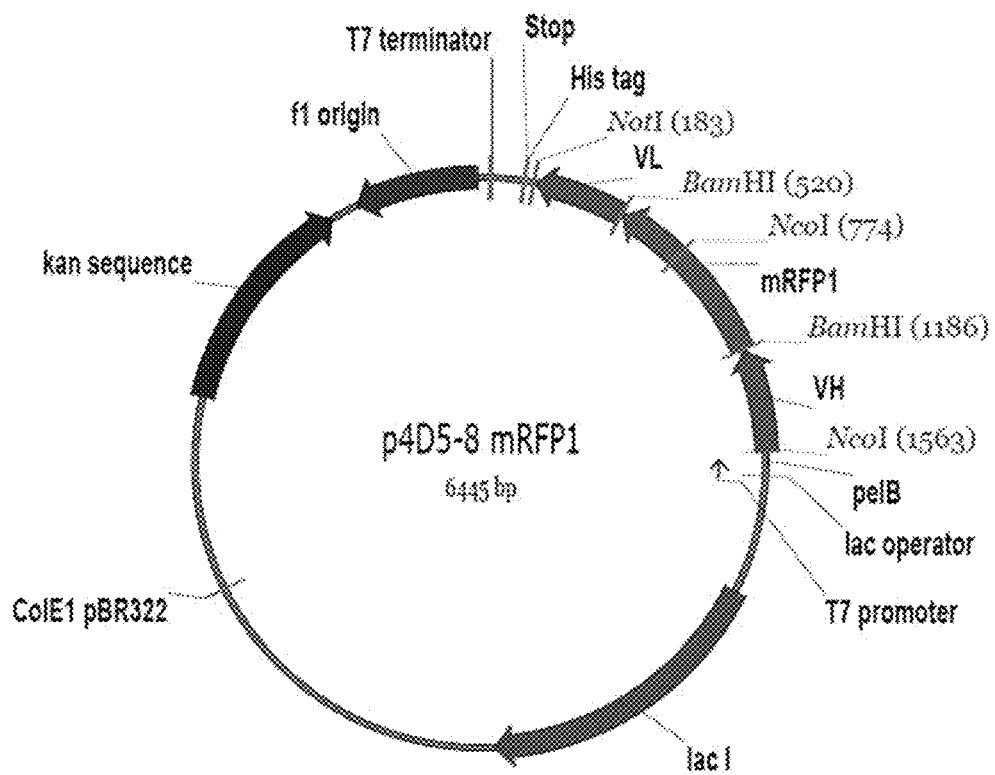

Construction of an exemplary vector expressing an exemplary scFv-fluorophore fusion is shown in FIG. 8B. A 714 bp NcoI/NotI fragment encoding the 4D5-8 scFv $V_H$-$V_L$ orientation with a five amino acid (Gly4Ser) linker incorporating an in-frame BamHI (GGA TCC) restriction site (encoding amino acids Gly Ser) was inserted into a modified pET-26b vector. Modified mRFP1 with similar (Gly4Ser) linkers on both ends was cloned into the scFv BamHI site.

Protein Expression and Purification.

The 52 kDa protein (4D5-8 $V_H$-RFP-$V_L$) was expressed in *E. coli* BL21 (DE3) pRARE or Rosetta gami B(DE3). During the growth and expression phase the bacteria had a distinct red pigmentation. The protein was initially enriched by immobilized metal ion affinity chromatography (IMAC) and fractions analyzed by SDS-PAGE (FIG. 9a) and western blot (FIG. 9b), and then analyzed by gel filtration chromatography compared with mRFP1 and standards confirming the basically monomeric state (FIG. 9c). The fractions with the red pigment corresponded to fractions 32-37. The purified monomeric protein was further analyzed by SDS-PAGE (FIG. 9d). Western blot analysis of the eluted fractions (FIG. 9b), revealed a band above the expected size, and smaller products. The higher band probably corresponds to the protein with the PelB leader intact, recovered from the cell lysis and the lower bands are the breakdown products due heat induced proteolysis of mRFP1 at the chromophore site which has also been reported by others (Serebrovskaya et al., 2009 Proc Natl Acad Sci USA 106(23):9221-9225). The proteolysis occurs upon sample preparation for SDS-PAGE. A final yield of the 4D5-8 REDantibody was 5 mg/L of bacterial culture.

Flow Cytometry and Fluorescence Microscopy Analysis.

Figure 10:
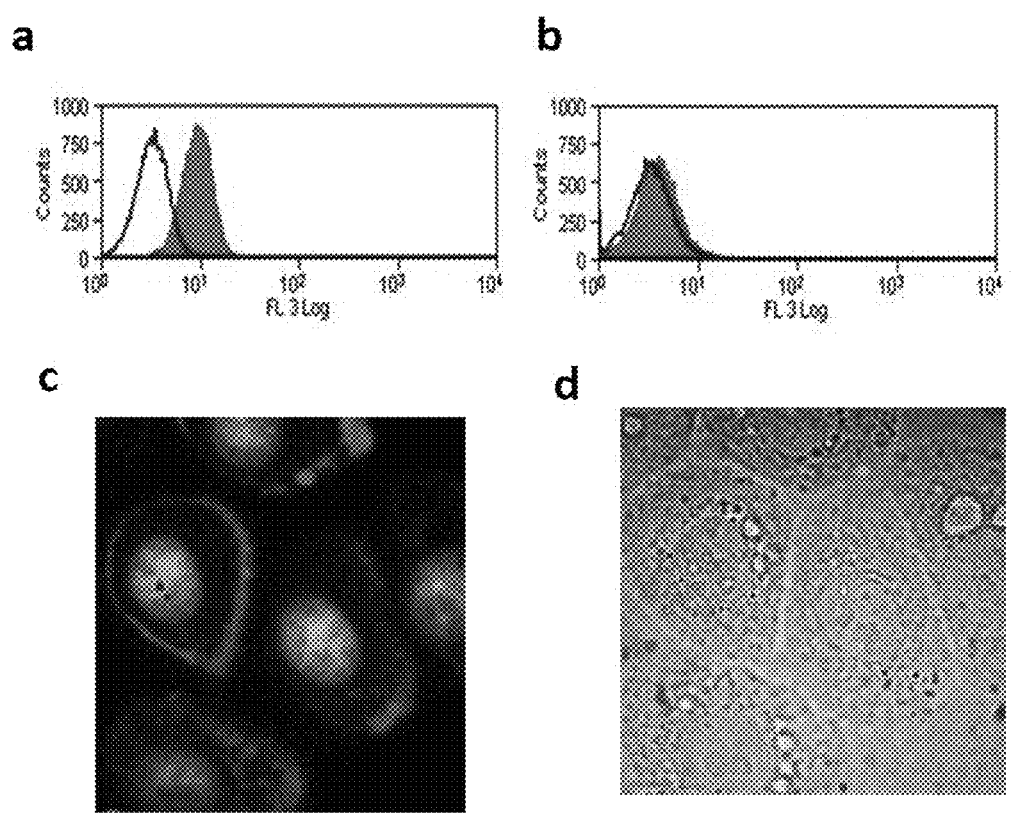
FIG. 10 shows binding properties of purified 4D5-8mRFP1. (a) Detection of 4D5-8mRFP1 binding to $p185^{HER-2-ECD}$-overexpressing SKBr-3 cells by flow cytometry. Cells incubated with 4D5-8mRFP1 are shown as filled peak and cells used as controls (solid line) were treated with MACS buffer alone. All experiments were normalized to 20,000 cells, excluding doublets. (b) Flow cytometry analysis of $p185^{HER-2-ECD}$ non expressing MDA-MD-231 cells incubated with 4D5-8mRFP1. (c) Fluorescence images of SKBr-3 cells incubated with 4D5-8mRFP1 and DNA (nucleus) binding dye GelGreen™ and (d) Bright-field images of the same SKBr-3 cells incubated with 4D5-8mRFP1.
Figure 16A:
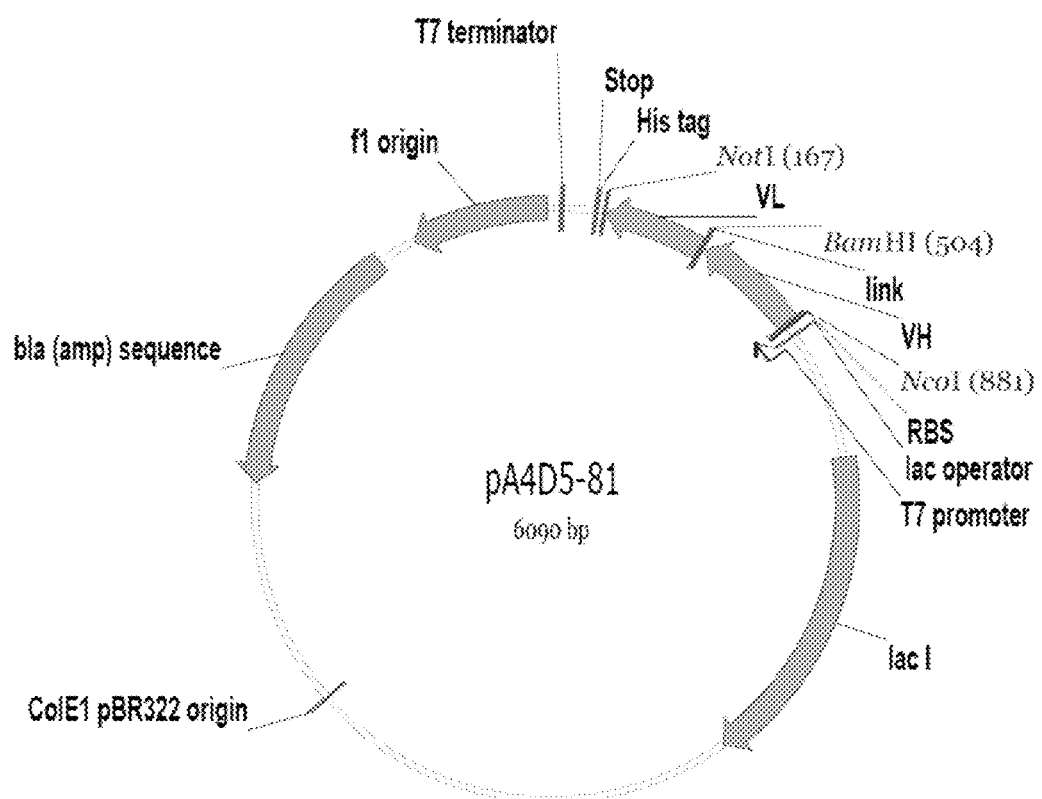
Figure 16C:
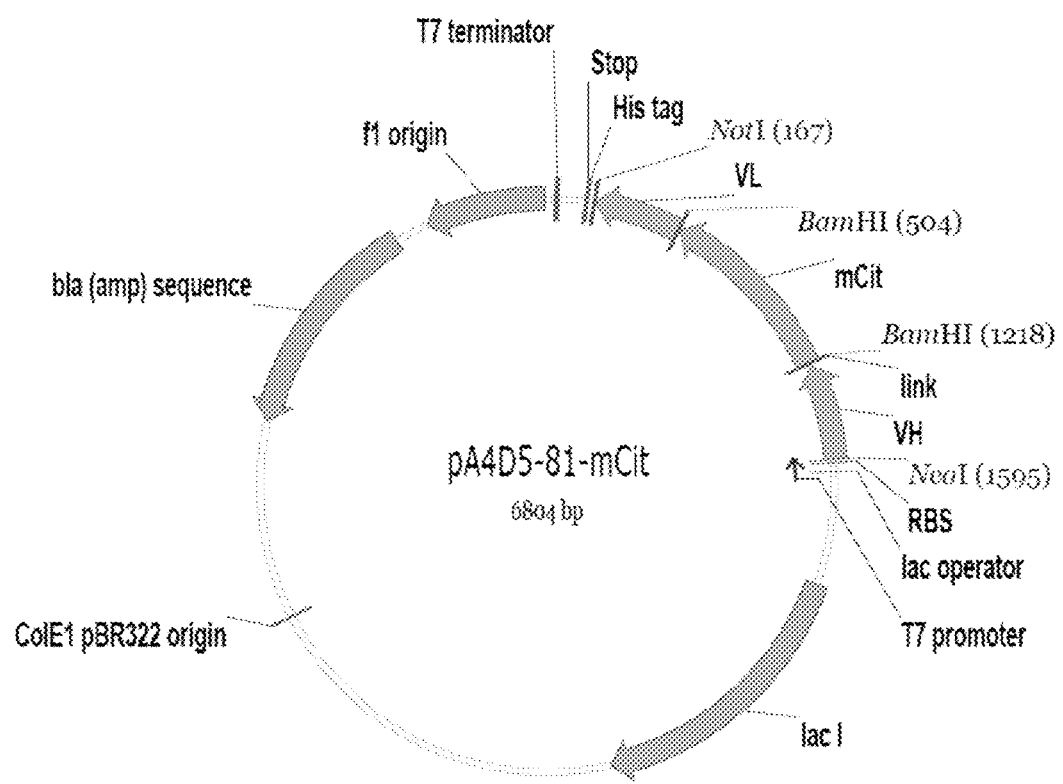
Figure 16D:
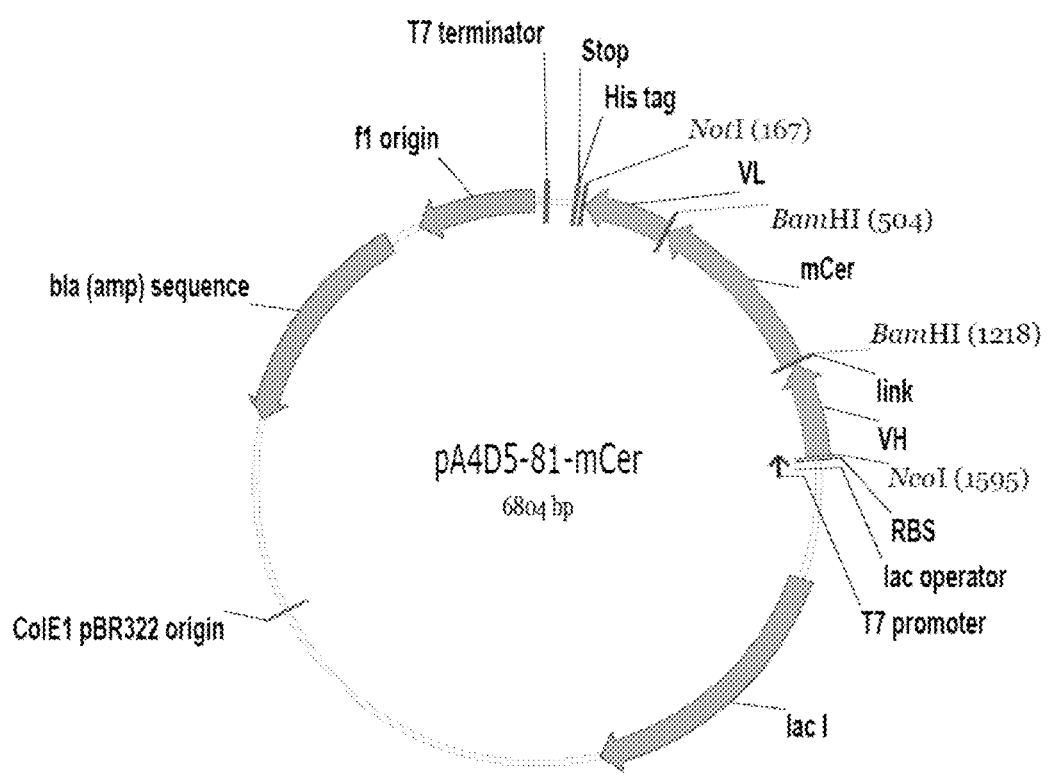
Figure 16E:
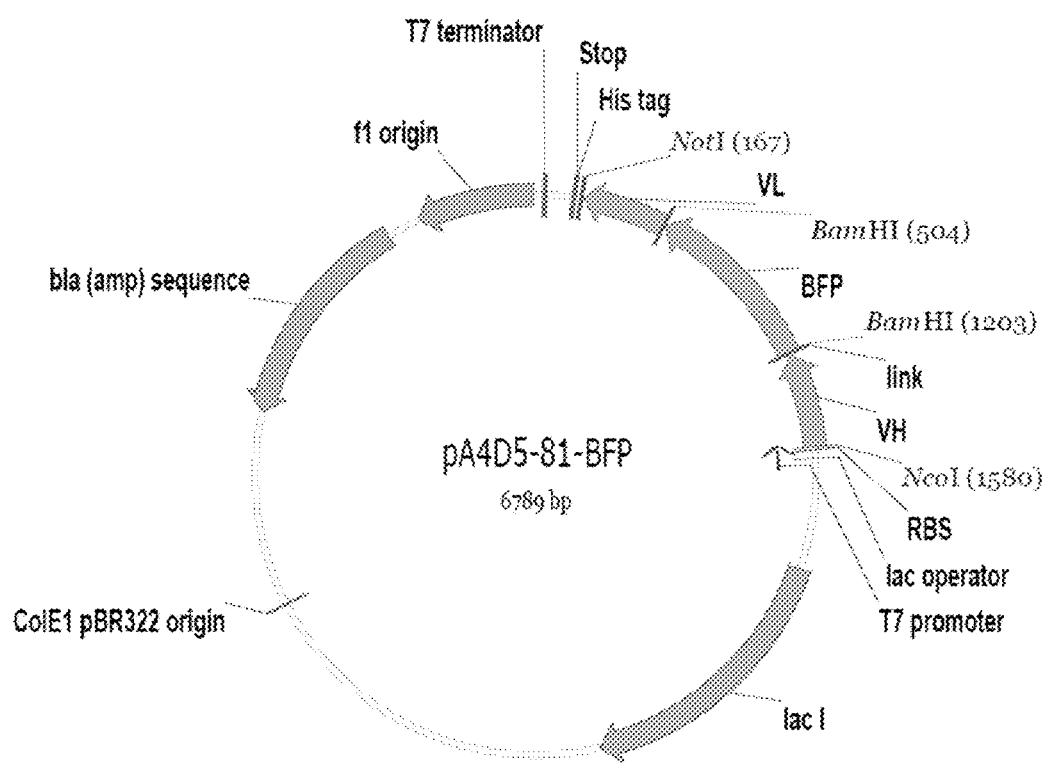
Figure 17A:
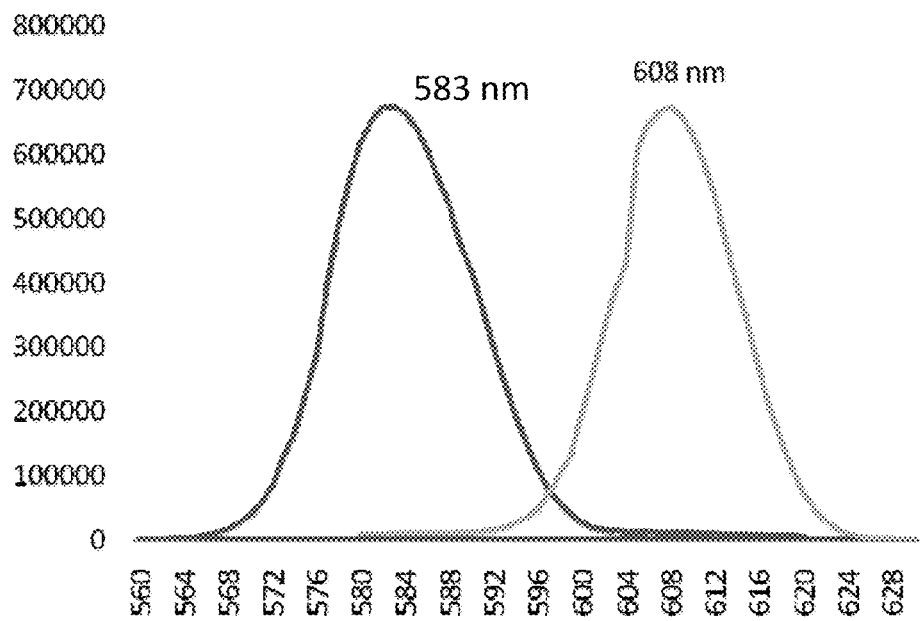
FIG. 17A-D shows excitation and emission spectra of 4D5-8 fluorescent fusion antibodies 4D5-8_mRFP (A), 4D5-8_mCit (B), 4D5-8_Cerul (C), and 4D5-8_BFP (D).
Figure 17B:
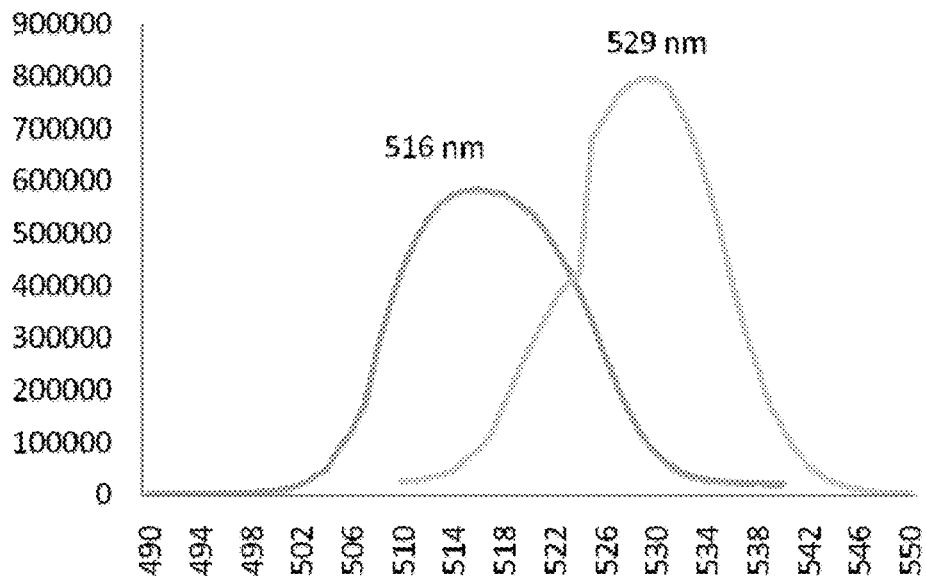
Figure 17C:
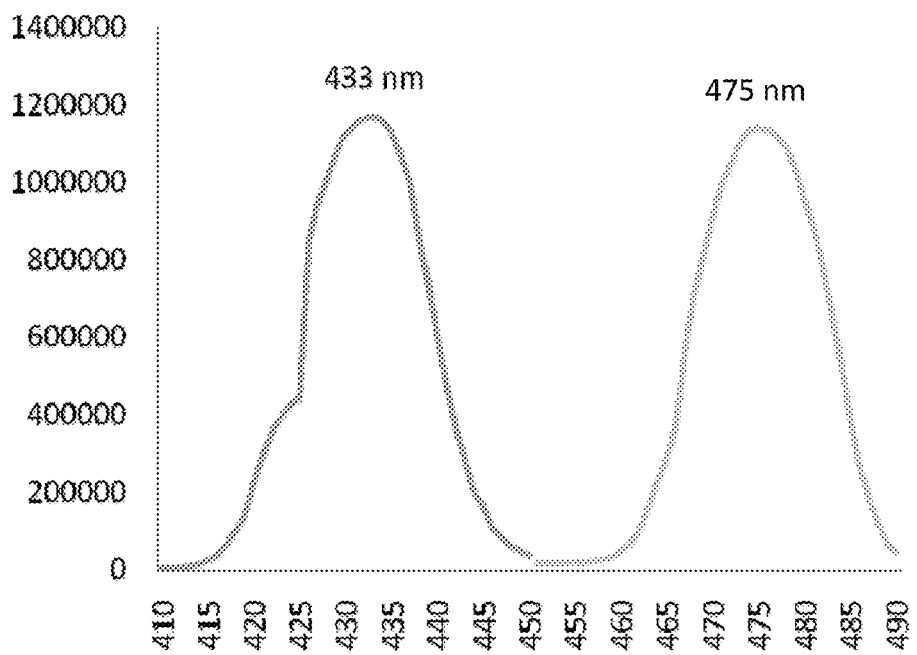
Figure 17D:
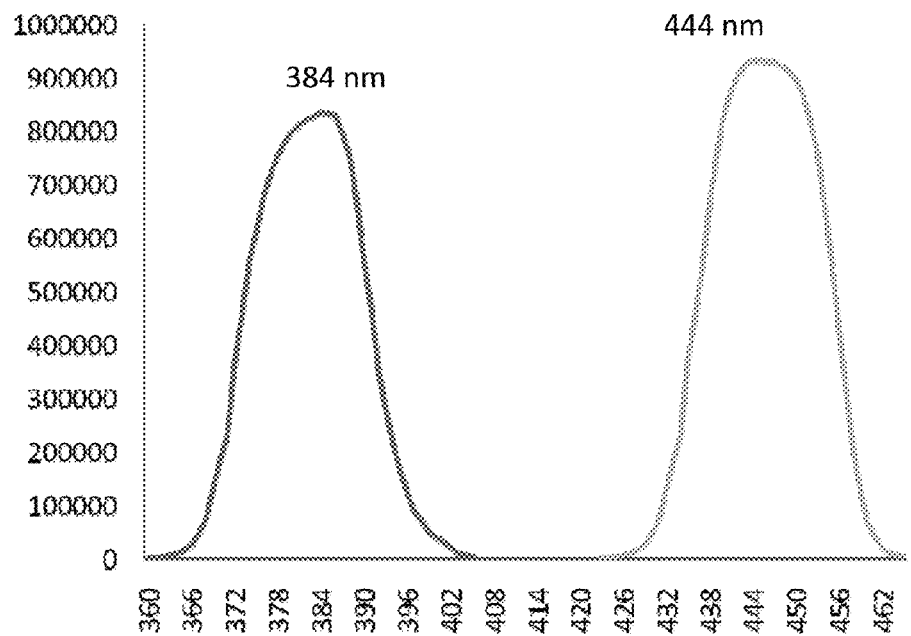

To further characterize the binding activity of 4D5-8 REDantibody we used flow cytometry and fluorescence microscopy. As shown in FIG. 10, purified red antibody effectively recognized SKBr-3 breast carcinoma cells that are characterized by high expression levels of p185HER-2-ECD (FIG. 10a) and is used as +++ positive control in the FDA approved HercepTest (Dako North America, Inc., Carpinteria, Calif.) and did not recognize the MDA-MD-231 cancer cells (FIG. 10b) which do not express p185HER-2-ECD and are used as a zero negative control in the same test (Prichard et al., 2008 Clin Lab Med 28(2):207-222, vi). Immunofluorescent staining of SKBr-3 breast cancer cells revealed that purified 4D5-8 REDantibody effectively accumulates on the surface of these cells after a 30-minute incubation at ambient temperature as shown in FIG. 10c and FIG. 10d.

Few genetically encoded fluorescent antibodies have been reported to date (Griep et al., 1999 J Immunol Methods 230(1-2):121-130; Lu et al., 2005 J Zhejiang Univ Sci B 6(8):832-837; Serebrovskaya et al., 2009 Proc Natl Acad Sci USA 106(23):9221-9225), in part because it has been proven difficult to maintain native affinity activity of antibody domains and maintain native fluorophore activity of the fluorophore domain. Efforts have included omitting the antibody component and creating a GFP-based biosensor possessing antibody-like properties using the GFP as a scaffold and introducing two proximal binding loops (Pavoor et al., 2009 Proc Natl Acad Sci USA 106(29):11895-11900). Conventional antibodies, however, have six proximal binding loops that, combined with subtle variations in the framework regions, can provide a much greater range of possible affinities and specificities. On the other hand, the rigid β-barrel structure of fluorescent proteins impose limits on the number of changes that can be accommodated without altering the spectral properties (Abedi et al., 1998 Nucleic Acids Res 26(2):623-630).

Ideally, a fluorescent antibody can possess as much native ligand-binding activity as possible from its antibody domains and as much of the native fluorophore spectral properties as possible from its fluorophore domain.

One way to retain as much ligand-binding activity and as much fluorophore activity as possible can involve a modular approach where the two functionalities reside in distinct, non-overlapping regions of a single molecule. However, recombinant scFv with linkers can be prone to disassociation and aggregation (Worn and Pluckthun, 2001 J Mol Biol 305(5):989-1010). Yet, in the context of a Fab molecule, the $V_H/V_L$ remain associated. Nature provides two solutions for stabilizing $V_H/V_L$ pairs. In conventional antibodies, the CH1 and the constant light chain orient and hold the $V_H$ and the $V_L$ in place for optimal interface pairing. In the other case, the $V_L$ is not required and only the $V_H$ is required for ligand binding, as is the case in camel antibodies (Hamers-Casterman et al., 1993 Nature 363(6428):446-448). Although making direct fluorophore fusions with engineered $V_H$ domains is possible, the vast majority of characterized monoclonal antibodies consist of both $V_H$ and $V_L$ domains. Thus, an approach that could conserve the Fab-like $V_H/V_L$ pairing and permit fusion with a fluorescent protein can produce a fluorescent antibody that possesses reliable spectral properties and high affinity and specificity characteristics.

We have devised a novel modular approach that produces efficient generation of a stable genetically-encoded intrinsically labeled fluorescent antibody. We have inserted the β-barrel structure of the fluorophore between the variable domains. These modular constructs not only introduce the fluorophore into the fusion molecule, but also stabilizes the positional orientation of the variable domain interfaces, resulting in Fab-like $V_H/V_L$ pairing and, therefore, Fab-like ligand binding.

In the embodiment described in Example 1, the $V_H$ C-terminus is fused to the N-terminus of mRFP1, replacing the CH1 domain. The C-terminus of mRFP1 is fused to the N-terminus of the $V_L$, providing an alternative anchor for the $V_L$ and thus eliminating a need for the CL. The exemplary 4D5-8 REDantibody described in Example 1 has the following characteristics: it is readily expressed and isolated from *E. coli*, with a molecular weight similar to the Fab fragment; the fluorophore activity remains unaltered; it is monomeric; it is stable; it retains the specificity of the parental antibody; and it is simple to use as a single reagent in immunohistochemistry, flow cytometry, and/or molecular imaging.

The 4D5-8 REDantibody molecule may be used, for example, for the development of a diagnostic test for Her2-positive breast cancer in biopsy samples by immunohistochemistry or possibly for circulating cancer cells by FACs. Using this platform it should be possible to create panels of REDantibodies against a range of cancer and other biomarkers. Moreover, since the palette of monomeric fluorescent proteins (mHoneydew to mPlum) are based on the basic architecture of mRFP1 used in this study, it should be possible to exchange the red fluorophore for these other colored proteins that have similar 11 β-sheet barrel-like structure (Zimmer, 2002 Chem Rev 102(3):759-781). The combination of different antibody specificities each with a distinct color spectrum opens up the possibility of antibody mediated multiplexed analysis by fluorescence microscopy and FACs analysis. Exemplary modular fluorescent antibodies that produce colors other than the red color produces by the 4D5-8 REDantibody are described in Example 3.

Recently, p185HER-2-ECD expressing cancer cells have been targeted using 4D5 scFv fused to the N-termini of KillerRed (dimeric) reporter (Serebrovskaya et al., 2009 Proc Natl Acad Sci USA 106(23):9221-9225). Upon light irradiation in oxygen rich environment the KillerRed produces highly reactive oxygen species (ROS) which oxidise molecules in close proximity resulting in p185HER-2-ECD expressing cancer cell damage and death (Serebrovskaya et al., 2009 Proc Natl Acad Sci USA 106(23):9221-9225). These properties have also been assigned to other fluorescent proteins and it has been experimentally confirmed that during formation of the chromophore one molecule of $H_2O_2$ is generated for each molecule of fluorescent protein (Zhang et al., 2006 J Am Chem Soc 128(14):4766-4772). Therefore the 4D5-8mRFP1 described could also generates ROS upon exposure to ambient light, thus it may also have therapeutic potential in targeted cell ablation and photodynamic therapy. Another advantage of mRFP1 is its far-red spectrum which has a greater tissue penetration permitting use for in vivo imaging (Yurchenko et al., 2007 Transgenic Res 16(1):29-40). Antibody targeted mRFP1 may also be evaluated for use in vivo in diagnostic and/or therapeutic applications. This dual modular assembly permits improvements to be incorporated on the scFv and the fluorophore, resulting in opportunities for further combinatorial optimised binding and more desirable spectral properties. Similar REDantibody constructs based on the anti-sialyl-Tn and anti-sialylated Lewis (Le)a antibody B72.3 (Brady et al., 1991 J Mol Biol 219(4):603-604) and CA19.9 (Koprowski et al., 1979 Somatic Cell Genet 5(6):957-971) respectively have also been assembled.

Assembling the REDantibody using the genetically encoded fluorophore as a bridge results in a stabilized, stoichiometric molecule with each binding site having a single reporter molecule, allowing quantitative analysis. This platform may also be applied to other existing mAbs to create the next generation of diagnostic imaging and sorting molecules. The modular platform may also be used to combine natural and synthetic immunoglobulin $V_H$ and $V_L$ domains with libraries of fluorophores based on mRFP1 and GFP to create a palette of highly specific colored binding molecules that retain optimal binding and spectral properties.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Materials and Methods
Molecular Design and Visualization

Structure of B72.3 and 4D5 antibodies were downloaded from PDB database (PBD: 1BBJ and 1FVC respectively). RFP structure was predicted using Swiss-Model Workspace server. Further modeling was performed using MIFit+ software version 2009.09-1 (Rigaku Americas Corp., The Woodlands, Tex.) and protein models were viewed using PyMOL software version 1.1 (DeLano Scientific LLC, Palo Alto, Calif.).
Plasmids, Primers and Synthetic DNA Plasmid pBAK1 and pA were previously constructed in our laboratory is based on pET-26b and pET-32a vectors, respectively (EMD Chemicals Inc., Gibbstown, N.J.). All primers were purchased from Invitrogen Corp. (Carlsbad, Calif.). Synthetic DNA sequences of B72.3 and CA19.9 antibody variable domains in $V_H$-$V_L$ orientation were codon optimized for *E. coli* expression and purchased from Epoch Biolabs, Inc. (Missouri City, Tex.) as plasmids pBSK-B72.3 and pBSK-CA19.9 respectively, with NcoI, BamHI and NotI restriction sites to facilitate construction of the expression vectors. Plasmid pAK19 encoding the 4D5 $V_H$ and $V_L$ was provided by Dan Yansura (Genentech, Inc., South San Francisco, Calif.). Plasmids pMTRFP and pMTBFP, with mRFP1 and BFP genes, respectively, were a gift from Professor Ray St. Ledger (University of Maryland, College Park, Md.). Synthetic DNA sequences of mCitrine and Cerulean were codon optimized for *E. coli* expression and purchased from Epoch Biolabs, Inc. (Missouri City, Tex.) as plasmids pBSK-mCit and pBSK-Cer respectively, with flanking BamHI restriction sites to facilitate insertion into the expression vectors.
Bacterial Strains, Growth Media and Recombinant DNA Technique XL1-Blue *Escherichia coil* strain (Stratagene, Agilent Technologies, Inc., Santa Clara, Calif.) was used for plasmid construction steps. To express recombinant antibodies BL21 (DE3) or Rosetta gami B(DE3) strain of *E. coli* (EMD Chemicals Inc., Gibbstown, N.J.) were used. *E. coli* cells were grown in Lysogeny Broth (LB) (Bertani, 2004) or LB agar plates. Kanamycin sulfate, carbenicillin, and chloramphenicol were used at 30 µg/mL, 100 µg/mL, and 34 µg/mL final concentration, respectively. Plasmid DNA was isolated using QIAprep Spin Miniprep Kit (Qiagen Inc.—USA, Valencia, Calif.) and DNA from gel was purified using QIAquick Gel Extraction Kit (Qiagen Inc.—USA, Valencia, Calif.). *Escherichia coli* cells were transformed using standard heat shock methods. Restriction and modification enzymes were purchased from New England Biolabs, Inc. (Ipswich, Mass.). Final plasmid constructs were confirmed by DNA sequence analysis.

Construction of the Expression Plasmids

Antibody scFv encoding fragments were either digested directly from pBSK-B72.3, pBSK-CA19.9 or assembled from $V_H$ and $V_L$ domains encoded by pASK19 plasmids respectively and inserted into NcoI, and NotI restriction sites of previously digested plasmid pBAK1 to make pBAK1B72.3, pBAK1CA19.9 and pBAK14D5 respectively. The competent E. coli XL1 Blue cells were transformed using ligation mixtures and the clones were selected on the LB plates containing kanamycin. Positive clones were confirmed by DNA sequencing. To make RFP chimeras in $V_H$-RFP-$V_L$ orientation, plasmids pBAK1B72.3, pBAK1CA19.9 and pBAK14D5 were digested with BamHI restriction enzyme and PCR product of mRFP1 gene obtained using pMT-RFP plasmid template and oligonucleotide primers RFPBamF and RFPBamR (Table 1), inserted to produce pBAK1B72.3RFP, pBAK1CA19.9RFP and pBAK14D5RFP respectively. Colonies were initially screened by colony PCR using primers T7F and RFPBamR (Table 1) and selected clones confirmed by plasmid DNA sequencing.

Antibody scFv encoding fragments of 4D5-8 were digested from plasmid pBAK14D5 and inserted into pA plasmid to make pA4D5. The competent E. coli XL1 Blue cells were transformed using ligation mixtures and the clones were selected on the LB plates containing carbenicillin. Positive clones were confirmed by DNA sequencing. To make RFP, Citrine, and Cerulean chimeras in $V_H$-FP-$V_L$ orientation, this plasmid was digested with BamHI and the mRFP1 gene obtained using pMT-RFP plasmid template and oligonucleotide primers RFPBamF and RFPBamR (Table 1), was inserted to produce pA4D5RFP. The BamHI fragment encoding the mRFP was replaced by mCit and mCer to generate pA4D5mCit and pA4D5mCer respectively. Colonies were initially screened by colony PCR using primers T7F and RFPBamR (Table 1) or CITBamR selected clones confirmed by plasmid DNA sequencing.

Antibody Expression in E. coli Periplasm.

To express scFv and REDantibody chimeras, E. coli BL21 (DE3) pRARE (Phage-resistant derivative of BL21 (DE3) (EMD Chemicals Inc., Gibbstown, N.J.) cells were transformed with the appropriate plasmid and plated onto LB agar supplemented with kanamycin sulfate (30 μg/mL final concentration) and chloramphenicol (34 μg/mL final concentration). The cells were allowed to grow at 37° C. for 18 hours and the following day, five fresh colonies were inoculated into 10 mL of LB media (with antibiotics) and grown at 37° C. (with shaking at 250 rpm) for 16 hours. Next day, 200 mL of pre-warmed LB media, prepared in 1 L conical flasks (with antibiotics) were inoculated with 10 mL of the overnight culture and grown at 37° C. (with shaking at 250 rpm) until the optical density at 600 nm had reached 0.5, then the cells were placed on ice for 30 minutes and Isopropyl β-D-1-thiogalactopyranoside (IPTG) added (final concentration 0.3 mM) to the cultures and the cells were grown at 20° C. for an additional 20 hours with shaking at 250 rpm. Bacterial cells were pelleted by centrifugation for 20 minutes, 5,000 rpm at 4° C. (using Sorvall SuperT 21 bench top centrifuge, with SL-250T rotor) the supernatant discarded and the pellets retained for periplasmic protein extraction.

Antibody Expression in E. coli Cytoplasm.

To express scFv and REDantibody chimeras, in the cytoplasm of E. coli Rosetta gami (DE3) (EMD Chemicals Inc., Gibbstown, N.J.) cells were transformed with the appropriate plasmid and plated onto LB agar supplemented with carbenicillin and chloramphenicol (100 μg/mL and 34 μg/mL final concentration respectively). The cells were allowed to grow at 37° C. for 18 hours and the following day, five fresh colonies were inoculated into 10 mL of LB media (with antibiotics) and grown at 37° C. (with shaking at 250 rpm) for 16 hours. Next day, 200 mL of pre-warmed LB media, prepared in 1 L conical flasks (with antibiotics) were inoculated with 10 mL of the overnight culture and grown at 37° C. (with shaking at 250 rpm) until the optical density at 600 nm had reached 0.5, then the cells were placed on ice for 30 minutes and Isopropyl β-D-1-thiogalactopyranoside (IPTG) added (final concentration 1 mM) to the cultures and the cells were grown at 20° C. for an additional 20 hours with shaking at 250 rpm. Fifty mL aliquots of bacterial cultures were pelleted by centrifugation for 20 minutes, 5,000 rpm at 4° C. (using Sorvall SuperT 21 bench top centrifuge, with SL-250T rotor) the supernatant discarded and the pellets retained for cytoplasmic protein extraction.

Antibody Purification from E. coli Periplasm.

Bacterial cell pellets from 200 mL culture were resuspended in 10 mL of periplasmic buffer (30 mM Tris-base, pH 8.0, 20% sucrose and 1 mM EDTA) supplemented to a final concentration of 0.1 mM phenylmethylsulfonyl fluoride (PMSF). The cells were incubated on ice for 10 minutes and centrifuged at 9000 rpm for 10 minutes at 4° C. (using Sorvall SuperT 21 bench top centrifuge, with SL-50T rotor). The supernatants were collected and stored on ice, whilst cell pellets were resuspended in 7 mL of 5 mM MgCl2 (4° C.). After incubation for five minutes on ice, bacterial cells were pelleted by centrifugation as described before, and the supernatants combined to give the periplasmic fraction.

Antibody Purification from E. coli Cytoplasm.

Bacterial cell pellets from 50 mL culture were resuspended in 3 mL of periplasmic buffer (20 mM Tris-base, pH 8.0, 0.5 M NaCl, 10 mM imidazole 0.1% Triton-X-100) supplemented to a final concentration of 0.1 mM phenylmethylsulfonyl fluoride (PMSF), lysozyme 0.2 mg/mL and sonicated 6×30 second bursts. The cells were incubated on ice for 10 minutes and centrifuged at 13000 rpm for 10 minutes at 4° C. (using Biofuge). The supernatants were collected to give the cytoplasmic fraction.

Ni-NTA Purification of Recombinant Proteins.

Recombinant proteins were purified using a 1 mL HisTrap HP column (GE Healthcare) fitted to an ÄKTAprime™ plus (GE Healthcare, Piscataway, N.J.) liquid chromatography system. First, the 1 mL column was equilibrated with five column volumes of equilibration buffer (20 mM Tris-HCl, pH 8.0, 500 mM NaCl, 10 mM imidazole). Following this, 17 mL E. coli periplasmic fraction (diluted two times with 20 mM Tris-HCl, pH 8.0, 500 mM NaCl buffer) or 3 mL of the cytoplasmic extract was loaded onto the column and the column was washed with five column volumes of wash buffer (20 mM Tris-HCl, pH 8.0, 500 Mm NaCl, 20 mM imidazole). The protein was eluted with five column volumes of elution buffer (20 mM Tris-HCl, pH 8.0, 500 mM NaCl, 500 mM imidazole) and collected in 1 mL aliquots. Protein elution was monitored at 280 nm. Eluted fractions 1-5 were analysed by SDS-PAGE.

Desalting and Anion Exchange Chromatography

Recombinant antibody obtained by Ni-NTA purification were desalted using 40 mL Sephadex G25 column (GE Healthcare, Piscataway, N.J.) fitted to an ÄKTAprime™ plus (GE Healthcare, Piscataway, N.J.) liquid chromatography system in 20 mM Tris-HCl, pH 8.0 buffer and further purified using 1 mL HiTrap Q Sepharose FF column (GE Healthcare, Piscataway, N.J.) and eluted by increasing buffer salt concentration. First, a 1 mL column was equilibrated with five column volumes of equilibration buffer (20 mM Tris-HCl, pH 8.0). Following this, 5 mL of desalted antibody fraction was loaded onto the column and protein was eluted by increasing concentration of NaCl in 20 mM Tris-HCl, pH 8.0 buffer and collected into 1 mL fractions. Eluted antibodies were concentrated and the buffer exchanged to 20 mM Tris-HCl, pH 8.0 and 150 mM NaCl using Ultracel YM-10 Amicon centrifugal devices from Millipore. Protein concentration was determined using Bradford assay kit. (Bio-Rad Laboratories, Hercules, Calif.) (Bradford, 1976 Anal Biochem 72:248-54).

Size Exclusion Chromatography

SEC was performed on an ÄKTA Prime Plus using a HiLoad 16/60 Superdex 200 size-exclusion column (GE Healthcare, Amersham, UK) equilibrated with degassed phosphate buffered saline (PBS). The purified proteins were separated by loading 1 mL of the sample at a concentration of 100-200 µg/mL. The flow rate was 1 mL/min, and the absorbance of the eluted protein was monitored at 280 nm. The column was calibrated with the following protein standards: β-amylase (200 kDa), bovine serum albumin (66 kDa), carbonic anhydrase (29 kDa) and cytochrome c (12.4 kDa).

SDS-PAGE

The fractions eluted from the HisTrap column (1-5) were analysed by SDS-PAGE using 12% Tris-Glycine gels. Proteins were stained with Coomassie Blue 8250 as follows: after electrophoresis gel was submerged in plastic container into 50 mL of 0.025% Coomassie Blue in 10% acetic acid solution and heated in the microwave until boiling (approximately 1 minute), cooled down for two minutes on bench and destained in 50 mL of 10% acetic acid by repeating previous procedure of heating in microwave and cooling down. Finally, the gel was kept in 10% acetic acid before scanning.

Optical Properties Determination

The fluorescent measurements were carried out using SpectraMAX Gemini EM fluorescence microplate reader with Gemini EM software (Molecular Devices, Inc., Sunnyvale, Calif.) using Optiplex 96F microtitre plates (PerkinElmer, Inc., Waltham Mass.) with mRFP, mCIT, CER, and BFP 4D5-8 antibodies, 50 µg in 0.1 mL/well in phosphate buffered saline (137 mM NaCl, 2.5 mM KCl, 10 mM $Na_2HPO_4$ and 1.8 mM $KH_2PO_4$) pH7.4. Excitation and emission spectra were determined at 1 nm intervals and the arbitrary fluorescence units (AFU) recorded. The concentration dependant fluorescence with excitation 584 nm and emission 607 nm was determined for ten-fold serial dilutions of REDantibody 4D5-8 from a stock solution of 95 nmoles.

Surface Plasmon Resonance (SPR) Measurements

The SPR measurements were carried out on the BIAcore 3000 following the procedure previously described to determine the binding of 4D5-8 scFv with p185HER2-ECD (Worn and Pluckthun, 1998 FEBS Lett 427:357-61). The p185HER2-ECD antigen (Sino Biological Inc; Beijing, China) 100 µg/mL in 20 mM citrate buffer pH 4.0 was coupled to the CM-5 research grade sensor chip using an amine coupling kit (GE Healthcare, Piscataway, N.J.). The 4D5-8 REDantibody was applied at 50 µg/mL, 100 µg/mL, 175 µg/mL, 250 µg/mL, and 500 µg/mL to the chip at a flow rate of 20 µL/min at 20° C. The surface was regenerated by injection of 45 µL of 0.1 M glycine-HCL, pH 2.2, 0.5 M NaCl. Data were analyzed using the global fit in the BIAevaluation program version 4.1

Immunofluorescent Confocal Microscopy

Wild-type *T. cruzi* epimastigote four-days-old cultures were fixed with 2% paraformaldehyde in phosphate buffer and allowed to adhere onto glass slides. Adhered cells were washed with PBS and non-specific antigen-binding sites were blocked with 2% BSA in PBS, pH 8.0, for 1 hour at room temperature. Samples were incubated for 60 minutes at room temperature with recombinant REDantibodies. REDantibody 4D5 was used as a negative control. Slides were mounted in Npropylgalate (Sigma P130, Sigma-Aldrich, St. Louis, Mo.) to reduce photobleaching and observed on a Leica SP2 Confocal Laser Scanning Microscope, using 543-nm He—Ne laser. All images were analysed using IMARIS software version 6.3 (Bitplane). Formaldehyde fixed *Trypanosoma cruzi* epimastigotes TC1 strain were a gift from Professor Michael Miles and Michael Lewis.

Example 2

Monomeric Recombinant Fluorescent Antibody Platform for Cell Sorting and Molecular Imaging Methods Molecular Modelling.

X-ray structures of human Her2 with HERCEPTIN (Genentech, Inc., South San Francisco, Calif.) antibody (PDB 1N8Z) and DsRed (PDB 1GyK) were downloaded from RCSB Protein data bank. A mRFP1 model was generated by homology-modeling using server Swiss-Model. MIFit program (Rigaku Americas Corp., The Woodlands, Tex.) was used to obtain a molecular 3D model of human Her2 with HERCEPTIN (Genentech, Inc., South San Francisco, Calif.) Fv domains and mRFP1. The 3D model of the proposed refined structure 4D5-8mRFP1 was generated using PyMOL software.

Construction of the Expression p4D5-8mRFP1 Vector.

Genetic engineering manipulations, plasmid preparation, cell culture, protein expression and cell lysis followed the standard protocols.

Primers are shown in Table 3.

TABLE 3

| Primer | Sequence | SEQ ID NO: |
|---|---|---|
| 4D5BAMF | 5'-GTCCCTTCTCGCTTCTCTGGGT CCAGATCTGGGACGGATTTCAC-3' | SEQ ID NO: 9 |
| 4D5BAMR | 5'-GTGAAATCCGTCCCAGATCTGG ACCCAGAGAAGCGAGAAGGGAC-3' | SEQ ID NO: 10 |
| PAKVLBAM | 5'-CAGCGGCGGAGGCGGATCCGAT ATCCAGATGACCCAGTC-3' | SEQ ID NO: 11 |
| PAKVLNOT | 5'-TCGAGTGCGGCCGCATCCGCGC GTTTGATCTCCACCTTGGTAC-3' | SEQ ID NO: 12 |
| PAKVHBAM | 5'-TCGGATCCGCCTCCGCCCGAGG AGACGGTGACCAGGGTTC-3' | SEQ ID NO: 13 |
| PAKVHNCO | 5'-TAGGCCATGGCCGAGGTTCAGC TGGTGGAG-3' | SEQ ID NO: 14 |
| RFPBamF | 5'-CAGTGGATCCGAGGACGTCATC AAGGAGTTC-3' | SEQ ID NO: 15 |
| RFPBamR | 5'-CAGTGGATCCGCCTCCGCCTGT GCGGCCCTCGGCGCGCTCGTAC-3' | SEQ ID NO: 16 |
| CITBamR | CAGTGGATCCGCCGCCGCCGGTAAT GCCCGCCGCGGTCAC | SEQ ID NO: 17 |

All primers were purchased from Invitrogen Corp. (Carlsbad, Calif.). Plasmids pAK19 was provided by Dan Yansura (Genentech, Inc., South San Francisco, Calif.), pMT-RFP and pMT-BFP were provided by Ray St. Ledger (University of Maryland, College Park, Md.). Restriction nuclease NcoI, NoI and BamHI, T4 DNA ligase, CIP were purchased from New England Biolabs, Inc. (Ipswich, Mass.). The mRFP1 was amplified by PCR from pMT-RFP plasmid using primers RFPBamF and RFPBamR. The $V_H$ and $V_L$ domains of the humanized humAb 4D5-8 antibody were amplified by PCR from the plasmid pAK19 using PAKVHNCO/PAKVHBAM and PAKVLBAM/PAKVLNOT respectively. To obtain the scFv of the humanized 4D5-8 antibody and simultaneously introduce BamHI restriction site between $V_H$ and $V_L$ chains, PCR amplified $V_H$ and $V_L$ chains were joined by splice-overlapping PCR using PAKVHNCO and PAKVLNOT. Internal BamHI site present in the original $V_L$ chain of humAb4D5-8 was eliminated by two-step mutagenesis PCR using primers 4D5BAMF and 4D5BAMR. Final product of scFv 4D5-8 was digested with NcoI and NotI restriction enzymes and inserted into the same sites of pBAK1 plasmid in frame with pelB leader sequence and an octa His-tag to make p4D5-8Bam plasmid. This plasmid was subsequently digested with BamHI and mRFP1 DNA inserted to obtain p4D5-8mRFP1 plasmid. All constructs were verified by DNA sequencing.

Protein Expression.

Transformants from strain BL21 (DE3) pRARE (Phage-resistant derivative of BL21(DE3), with pRARE plasmid encoding rare codon tRNAs, chloramphenicol-resistant) were inoculated into 200 mL Luria-Bertani (LB) medium plus kanamycin (30 µg/mL) and chloramphenicol (34 µg/mL), and grown overnight at 37° C. This culture was used to inoculate a 12 L fermentor (1:60 dilution) containing LB medium plus kanamycin (30 µg/mL) and chloramphenicol (34 µg/mL), and grown for approximately 5 hours at 37° C. until optical density ($OD_{600nm}$) of the culture reached 0.6. Then Isopropyl-β-D-thio-galactoside (IPTG) at the final concentration of 0.3 mM was added to the culture to induce protein expression. Fermentations were performed at 20° C. for 20 hours at 350 rpm, four gas volume flow per unit of liquid volume per minute (vvm) aeration at pH 7.2.

Protein Purification and Analysis.

Protein was prepared from the whole cell lysates, purified on 1 mL HisTrap HP Ni Sepharose™ column using ÄKTAprime™ plus purification system (GE Healthcare, Piscataway, N.J.) and analyzed by two 12% SDS-PAGE Tris-Glycine gels. One gel was stained with Coomassie and the other was used for Western immunoblots. The cells were harvested, washed with PBS, centrifuged, and the pellet was resuspended in lysis buffer (0.01 M Tris HCl pH 8.0, containing 0.5 M NaCl, 10 mM imidazole and 0.1% (vol/vol) Triton X100) and sonicated on ice. The lysate was then centrifuged at 22,000×g for 30 minutes at 4° C. The supernatant was used for the purification of His-tagged proteins using immobilized metal ion affinity chromatography (IMAC) and proteins were eluted with 500 mM imidazole. The metal affinity-enriched proteins were loaded onto Sephadex G200 gel filtration column (GE Healthcare, Piscataway, N.J.) run using 0.02 M Tris HCl pH 7.5, containing 0.15 M NaCl, with a flow rate of 1 mL/min, collecting 1 mL fractions. Fractions 32-37 were pooled and concentrated using Microcon concentrators (Millipore, Billerica, Mass.) with a molecular mass cutoff of 10 kDa, and verified by SDS-PAGE and Western blot analysis. SDS/PAGE analyses were performed according to the standard protocols using 12% polyacrylamide gels. Immunoblots on nitrocellulose membrane (Millipore, Billerica, Mass.) were carried out according to the manufacturer's instructions using monoclonal anti-poly histidine-alkaline phosphatase antibody clone His-1 (Sigma A5588, Sigma-Aldrich, St. Louis, Mo.) were visualized using an 5-bromo-4-chloro-3-indolyl phosphate (BCIP)/nitroblue tetrazolium (NBT) (Sigma B1911, Sigma-Aldrich, St. Louis, Mo.).

Flow Cytometry and Fluorescence Microscopy Analysis.

The SKBr-3 and MDA-MB-231 cell lines were maintained in RPMI medium 1640, supplemented with 10% FCS and 2 mM L-glutamine in culture flasks. For flow cytometry analysis, the adherent SKBr-3 and MDA-MB-231 cells were carefully detached with trypsin in PBS (pH 8.0) containing 5 mM EDTA. After a brief wash with cold PBS the cells were incubated with 0.2% paraformaldehyde in PBS for five minutes and again washed with cold PBS, counted, incubated with 4D5-8mRFP1 30 minutes on ice, washed twice with cold buffer Dulbecco's PBS containing 1% FCS, 2 mM EDTA (pH 7.2) (MACS), and analyzed by CyAn™ ADP flow cytometer (Dako North America, Inc., Carpinteria, Calif.). Results were analyzed using Summit software from Beckman Coulter. For immunofluorescent analysis, cells were plated on glass cover slips at density of $4 \times 10^3$ cells per well and cultured overnight at 37° C. in a 5% CO2 atmosphere. Cells were fixed in 0.2% paraformaldehyde in PBS for five minutes, washed with PBS 3x, permeabilized with 0.1% Triton-X 100 in PBS for five minutes, washed as before, incubated with 4D5-8mRFP1 (10 µg/mL) and GelGreen™ nuclear stain (Biotium, Inc., Hayward, Calif.) for 30 minutes, washed as before and analyzed using fluorescence microscope Axioscop 50 (Carl Zeiss MicroImaging, LLC; Thornwood, N.Y.). Images were captured by using a CCD camera (PowerShot digital camera, Canon U.S.A., Inc., Lake Success, N.Y.) and AxioVision software (Carl Zeiss MicroImaging, LLC; Thornwood, N.Y.).

Molecular Design and Visualisation

Structure of B72.3 and 4D5 antibodies were downloaded from PDB database (PBD: 1BBJ and 1FVC respectively). RFP structure was predicted using Swiss-Model Workspace server. Further modeling was performed using MIFit+ software version 2009.09-1 (Rigaku Americas Corp., The Woodlands, Tex.) and protein models were viewed using PyMOL software version 1.1 (DeLano Scientific LLC, Palo Alto, Calif.).

Plasmids, Primers and Synthetic DNA

Plasmid pBAK1, previously constructed in our laboratory is based on pET-26b vector (EMD Chemicals Inc., Gibbstown, N.J.). All primers were purchased from Invitrogen Corp. (Carlsbad, Calif.). Synthetic DNA sequences of B72.3 and CA19.9 antibody variable domains in $V_H$-$V_L$ orientation were codon optimized for *E. coli* expression and purchased from Epoch Biolabs, Inc. (Missouri City, Tex.) as plasmids pBSK-B72.3 and pBSK-CA19.9, respectively, with NcoI, BamHI and NotI restriction sites to facilitate construction of the expression vectors. Plasmid pAK19 encoding the 4D5-8 $V_H$ and $V_L$ was provided by Dan Yansura (Genentech, Inc., South San Francisco, Calif.). Plasmid pMT-RFP with mRFP1 gene was a gift from Professor Ray St. Ledger.

Bacterial Strains, Growth Media and Recombinant DNA Technique

XL1-Blue *Escherichia coli* strain (Stratagene, Agilent Technologies, Inc., Santa Clara, Calif.) was used for plasmid construction steps. To express recombinant antibodies BL21 (DE3) strain of *E. coli* (EMD Chemicals Inc., Gibbstown, N.J.) were used. *E. coli* cells were grown in Lysogeny Broth (LB) (Bertani, 2004 J Bacteriol 186:595-600) or LB agar plates. Kanamycin sulfate and carbenicillin were used at 30

μg/mL and 100 μg/mL final concentrations respectively. Plasmid DNA was isolated using QIAprep Spin Miniprep Kit (Qiagen Inc.—USA, Valencia, Calif.) and DNA from gel was purified using QIAquick Gel Extraction Kit (Qiagen Inc.—USA, Valencia, Calif.). E. coli cells were transformed using standard heat shock methods. Restriction and modification enzymes were purchased from New England Biolabs, Inc. (Ipswich, Mass.). Final plasmid constructs were confirmed by DNA sequence analysis.

Construction of the Expression Plasmid

Antibody scFv encoding fragments were either digested directly from pBSK-B72.3, pBSK-CA19.9 or assembled from $V_H$ and $V_L$ domains encoded by pASK19 plasmids respectively and inserted into NcoI, and NotI restriction sites of previously digested plasmid pBAK1 to make pBAK1B72.3, pBAK1CA19.9 and pBAK14D5 respectively. The competent E. coli XL1 Blue cells were transformed using ligation mixtures and the clones were selected on the LB plates containing kanamycin. Positive clones were confirmed by DNA sequencing. To make RFP chimeras in $V_H$-RFP-$V_L$ orientation, plasmids pBAK1B72.3, pBAK1CA19.9 and pBAK14D5 were digested with BamHI restriction enzyme and PCR product of mRFP1 gene obtained using pMT-RFP plasmid template and oligonucleotide primers RFPBamF and RFPBamR (Table 1), inserted to produce pBAK1B72.3RFP, pBAK1CA19.9RFP and pBAK14D5RFP respectively. Colonies were initially screened by colony PCR using primers T7F and RFPBamR (Table 1) and selected clones confirmed by plasmid DNA sequencing.

Antibody Expression in E. coli.

To express scFv and REDantibody chimeras, E. coli BL21 (DE3) (EMD Chemicals Inc., Gibbstown, N.J.) cells were transformed with the appropriate plasmid and plated onto LB agar supplemented with kanamycin sulfate (30 μg/mL final concentration). The cells were allowed to grow at 37° C. for 18 hours and the following day, five fresh colonies were inoculated into 10 mL of LB media (with antibiotics) and grown at 37° C. (with shaking at 250 rpm) for 16 hours. Next day, 200 mL of pre-warmed LB media, prepared in 1 L conical flasks (with antibiotics) were inoculated with 10 mL of the overnight culture and grown at 37° C. (with shaking at 250 rpm) until the optical density at 600 nm ($OD_{600}$) had reached 0.5, then the cells were placed on ice for 30 minutes and Isopropyl β-D-1-thiogalactopyranoside (IPTG) added (final concentration 0.3 mM) to the cultures and the cells were grown at 20° C. for an additional 20 hours with shaking at 250 rpm. Bacterial cells were pelleted by centrifugation for 20 minutes, 5,000 rpm at 4° C. (using Sorvall SuperT 21 bench top centrifuge, with SL-250T rotor), the supernatant discarded, and the pellets retained for periplasmic protein extraction.

Antibody Purification from E. coli Periplasm.

Bacterial cell pellets from 200 mL culture were resuspended in 10 mL of periplasmic buffer (30 mM Tris-base, pH 8.0, 20% sucrose and 1 mM EDTA) supplemented to a final concentration of 0.1 mM phenylmethylsulfonyl fluoride (PMSF). The cells were incubated on ice for 10 minutes and centrifuged at 9000 rpm for 10 minutes at 4° C. (using Sorvall SuperT 21 bench top centrifuge, with SL-50T rotor). The supernatants were collected and stored on ice; cell pellets were resuspended in 7 mL of 5 mM $MgCl_2$ (4° C.). After incubation for five minutes on ice, bacterial cells were pelleted by centrifugation as described above, and the supernatants combined to give the periplasmic fraction.

Ni-NTA Purification of Recombinant Proteins.

Recombinant proteins were purified using a 1 mL HisTrap HP column (GE Healthcare, Piscataway, N.J.) fitted to an ÄKTAprime™ plus (GE Healthcare, Piscataway, N.J.) liquid chromatography system. First, the 1 mL column was equilibrated with five column volumes of equilibration buffer (20 mM Tris-HCl, pH 8.0, 500 mM NaCl, 10 mM imidazole). Following this, 17 mL E. coli periplasmic fraction (diluted two times with 20 mM Tris-HCl, pH 8.0, 500 mM NaCl buffer) was loaded onto the column and the column was washed with five column volumes of wash buffer (20 mM Tris-HCl, pH 8.0, 500 mM NaCl, 20 mM imidazole). The protein was eluted with five column volumes of elution buffer (20 mM Tris-HCl, pH 8.0, 500 mM NaCl, 500 mM imidazole) and collected in 1 mL aliquots. Protein elution was monitored at 280 nm. Eluted fractions 1-5 were analyzed by SDS-PAGE.

Desalting and Anion Exchange Chromatography

Recombinant antibody obtained by Ni-NTA purification were desalted using 40 mL Sephadex G25 column (GE Healthcare, Piscataway, N.J.) fitted to an ÄKTAprime™ plus (GE Healthcare, Piscataway, N.J.) liquid chromatography system in 20 mM Tris-HCl, pH 8.0 buffer and further purified using 1 mL HiTrap Q Sepharose FF column (GE Healthcare, Piscataway, N.J.) and eluted by increasing buffer salt concentration. First, a 1 mL column was equilibrated with five column volumes of equilibration buffer (20 mM Tris-HCl, pH 8.0). Following this, 5 mL of desalted antibody fraction was loaded onto the column and protein was eluted by increasing concentration of NaCl in 20 mM Tris-HCl, pH 8.0 buffer and collected into 1 mL fractions. Eluted antibodies were concentrated and the buffer exchanged to 20 mM Tris-HCl, pH 8.0 and 150 mM NaCl using Ultracel YM-10 Amicon centrifugal devices (Millipore, Billerica, Mass.). Protein concentration was determined using Bradford assay kit (Bio-Rad Laboratories, Hercules, Calif.) (Bradford, 1976 Anal Biochem 72:248-54).

Size Exclusion Chromatography

Size exclusion chromatography was performed on an ÄKTA Prime Plus using a HiLoad 16/60 Superdex 200 size-exclusion column (GE Healthcare, Piscataway, N.J.) equilibrated with degassed phosphate buffered saline (PBS). The purified proteins were separated by loading 1 mL of the sample at a concentration of 100-200 μg/mL. The flow rate was 1 mL/min, and the absorbance of the eluted protein was monitored at 280 nm. The column was calibrated with the following protein standards: β-amylase (200 kDa), bovine serum albumin (66 kDa), carbonic anhydrase (29 kDa) and cytochrome c (12.4 kDa).

SDS-PAGE

The fractions eluted from the HisTrap column (1-5) were analysed by SDS-PAGE using 12% Tris-Glycine gels. Proteins were stained with Coomassie Blue 8250 as follows: after electrophoresis gel was submerged in plastic container into 50 mL of 0.025% Coomassie Blue in 10% acetic acid solution and heated in the microwave until boiling (approximately 1 min), cooled down for two minutes on the bench and destained in 50 mL of 10% acetic acid by repeating previous procedure of heating in microwave and cooling down. Finally, the gel was kept in 10% acetic acid before scanning.

Example 3

Delivery of Recombinant P. agglomerans to the Cibarium of H. vitripennis

For this experiment, one can use adult H. vitripennis collected from citrus orchards at the Agricultural Operations at UC Riverside. Experimental group plants can be coated with recombinant *P. agglomerans* containing a plasmid encoding a fluorescent antibody such as, for example, the REDantibody described herein. Control group plants can be coated with bacteria-free growth medium.

To verify that sharpshooters from the Agricultural Operations are free of recombinant *P. agglomerans* in their natural state, one can analyze *P. agglomerans* cibarial tissues using PCR and fluorescence microscopy. For each trial, one can use 10 potted Chardonnay grape vines of 3 years' age that exhibit new growth. The shoots of each plant can be hand painted with liquid cultures of recombinant *P. agglomerans* at a concentration of $10^8$ CFU/mL to achieve coverage of 100 percent surface area. Application of recombinant *P. agglomerans* cultures can occur with 1.0 mL/cm$^2$ of plant surface area (shoots only). In the set-up of this trial, one can trim the 10 plants to allow approximately 200 cm$^2$ of shoot surface area. Thus, one delivers approximately 200 mL or close to $2 \times 10^{10}$ CFU of recombinant *P. agglomerans* to each plant.

Sharpshooters (n=100) can be introduced into the cage and allowed to feed for 5 days. At this early stage, one observes little mortality and one can remove all sharpshooters from the cage and place them in a new cage containing five untreated plants. At transfer, 20 sharpshooters can be sacrificed and cibarial tissues can be dissected out. Analysis of colonization by recombinant *P. agglomerans* can be conducted using three methods: (1) confocal microscopy to detect Red Fluorescent Protein at 608 nm (2) qtPCR with primers specific for *P. agglomerans*, and (3) standard light microscopy for visualization of red bacteria. The remaining 80 insects can be serially analyzed over the next 20 days for retention of recombinant *P. agglomerans* in the cibarium.

Recombinant *P. agglomerans* will colonize the cibarium of *H. vitripennis*. In the initial 20 sharpshooters that are removed after five days, uniform colonization of the anterior mouthparts of *H. vitripennis* will be observed. The outcome of cibarial colonization can be measured by fluorescence/confocal microscopy, qtPCR, and/or light microscopy for visualization of red pigment. Two specific outcomes can be measured: (1) percent of sharpshooters that carry recombinant *P. agglomerans* in the cibarium, and (2) relative microbial CFU in the sharpshooters that are positive for recombinant *P. agglomerans*. Other environmental bacteria may colonize the mouthparts of *H. vitripennis* and microbial competition can occur. One can measure total bacterial load by performing qtPCR with universal 16S RNA primers and measure the fraction of total bacterial burden that is attributed to recombinant *P. agglomerans*. The experimental parameters of this study—i.e., 100 percent coverage of shoots with $10^8$ CFU of recombinant *P. agglomerans* per mL of applied culture—are established to optimize conditions for colonization. Statistical significance of recombinant *P. agglomerans* colonization in experimental group sharpshooters can be determined by comparing qtPCR values with control insects by chi squared analysis.

The second part of this study, persistence of recombinant *P. agglomerans* after initial exposure can reveal colonization of the cibarium in experimental group sharpshooters. There may be some decrease in CFU over the 20-day period, but one can calculate rates of decay via qtPCR. The decay rate can adjust for plasmid loss of the engineered recombinant *P. agglomerans*.

Transmission Blocking Effect of REDantibody in GWSS

One can assess the effect of REDantibody, expressed by recombinant *P. agglomerans* in paratransgenic *H. vitripennis*, in: (1) rendering the arthropod refractory to challenge infection by *X. fastidiosa*, and (2) preventing transmission of the pathogen to healthy grape vines. Three groups of fourth-instar GWSS can be used: (1) an experimental group can be colonized with recombinant *P. agglomerans* as above (n=100), (2) a control group of GWSS can be exposed to *P. agglomerans* transformed to express a marker antibody (rDB3) that has no activity against *Xylella* (N=100), (3) a second control can consist of GWSS exposed to untransformed *P. agglomerans*.

For these studies, we can use freshly molted adults to increase likelihood of *Xylella* transmission. Sharpshooters can be exposed to *P. agglomerans*-coated Chardonnay grape plants for five days. Ten insects from each group can be sacrificed at day 5 to confirm cibarial colonization by *P. agglomerans* and expression of antibody (ELISA, Western blot). Using the protocol of Almeida and Purcell (Almeida, R. P. and Purcell, A. H., Transmission of *Xylella fastidiosa* to grapevines by Homalodisca coagulata (Hemiptera: Cicadellidae). J Econ Entomol, 2003. 96:264-71), remaining insects can be challenged with *X. fastidiosa*. Briefly, GWSS that have been exposed to *P. agglomerans* can be transferred to closed containers containing *Xylella*-infected Chardonnay grape (confirmed by culture and PCR of plant issues). Seedlings with succulent growth can be used throughout to maximize feeding and transmission. The Acquisition Access Period (AAP) can be two days. This can permit acquisition of *Xylella* by the nymphs and prevent excessive loss of the recombinant *P. agglomerans*. Following the two-day AAP, 10 insects from each group can be sacrificed and cibarial tissues can be examined by both culture and PCR for *X. fastidiosa*. Since presence of *Xylella* alone in GWSS is not correlated to subsequent transmission, we can assess infectivity of the three groups of insects by transferring them to fresh, uninfected grape plants with succulent growth for an Inoculation Access Period (IAP) of 7-21 days, until molting occurs. This can allow ample time for transmission to occur and, possibly, cycles of transmission to occur between plants. Plants from the previous step can be stored separately and monitored for a minimum of eight weeks to assess for symptoms of Pierce's Disease. All plants can be examined by culture and PCR to verify *X. fastidiosa* infection.

Insects in the two control groups will be infected with *Xylella* at rates of nearly 100 percent. Likewise, between 80-90% transmission of the pathogen and disease in target grape vines are seen in the control groups. Transmission of *Xylella* and infection of grape plants after the IAP, however, will be reduced by approximately 30%, preferably by approximately 50%, in the experimental group of sharpshooters.

Example 4

Survival and Dispersal of pSCR-189b-Transformed (Recombinant) *P. agglomerans* in the *Rhizosphere* of Chardonnay Grape Vines One can measure soil CFU of recombinant *P. agglomerans* before and after each 25-day trial for each of the experimental pots containing recombinant *P. agglomerans*-treated grape plants. Five separate soil samples (1.0 cm$^3$) can be taken from the base of the grape vine at days 1, 12, and 25. Soil analysis for recombinant *P. agglomerans* can be conducted using one or more of three techniques: (1) culture on selection agar with PCR identification of colonies (gold standard), (2) fluorescence microscopy to detect RFP, and/or (3) direct visualization of colonies on agar for red color. Analytic techniques can evaluate not only the persistence and dispersal of recombinant *P. agglomerans* into the *rhizosphere* but also the accuracy of direct color visualization of bacterial colonies to identify recombinant bacteria.

No recombinant *P. agglomerans* are present in the *rhizosphere* on day 1. Probing of shoots by GWSS, physical detachment of bacteria from shoots and movement of bacteria through watering activities may to contribute to *rhizosphere* invasion by recombinant *P. agglomerans*. Therefore, CFU counts of recombinant *P. agglomerans* may increase by day 12. Values on day 25 can reflect a balance of bacterial replication and gene decay. Comparison of values with control pots using chi-squared analysis can yield measures of statistical significance.

Definitive detection of recombinant *P. agglomerans* may be performed using colony PCR derived from selection agar, but may be a cumbersome and expensive method for field use to detect paratransgenics. CFU counts of red bacteria can initially be compared statistically to values obtained by colony PCR to determine the accuracy of direct visualization of color. Similar comparison can be made to fluorescent readouts that detect mRFP. Certain factors may decrease accuracy of visualization methods. First, other soil bacteria may appear red on agar (e.g., *Serratia* spp., *Gordonia* spp.). Second, subjective variability can confound the readings. Third, intensity of red color can wane over time. All readings that involve direct visualization of colonies on agar can be repeated by a blinded observer to minimize bias. Concordance between direct visual methods and PCR data can be used to determine accuracy of this method.

Extent of Horizontal Gene Transfer Between Recombinant Pa and *Rhizosphere* Bacteria Populations of recombinant *P. agglomerans* can be exposed to a variety of microbes commonly found in soil consortia to determine the extent of horizontal gene transfer (HGT). HGT is a dynamic process and accounts for significant portions of the genomes of bacteria such as *E. coli*. Conjugative transfer of plasmids, heterologous recombination of chromosomal material, retrotransposons, and phage-mediated gene flow are some of the mechanisms by which microbes exchange genetic material.

HGT may occur in this milieu and one can assess the ability to monitor HGT events using the REDantibody platform. Though HGT has contributed to plasticity of microbial genomes, individual events are relatively infrequent and result from bacterial encounters in the $10^{7-8}$ range. One can score events in these experiments by counting CFUs of recipient bacteria that acquire the transgene using one or more of: (1) selection and PCR-based assay of REDantibody gene, and/or (2) direct visualization for red color. Control exchanges can involve direct co-incubation of wild-type *P. agglomerans* with consortium bacteria. Statistical significance of the difference in events—e.g., HGT from control versus recombinant *P. agglomerans*, and quantification of bacteria using PCR-based analysis versus direct color visualization—can be calculated using chi-squared analysis.

Recombinant *P. agglomerans* expressing bright red color can be co-incubated with representative bacteria of the *rhizosphere* of common agricultural plants. Though *rhizosphere* analysis reveals highly varied structure and variability over time, one can choose five representative organisms that are commonly found in soil environments: *Pseudomonas fluorescens, Arthrobacter globiformis, Escherichia coli, Enterobacter agglomerans*, and *Acinetobacter* sp. For these studies, one may elect to include only Gram-negative bacteria with similar lipid bilayer membranes as *P. agglomerans*. Though Gram-positive bacteria with peptidoglycan membranes and eukaryotic organisms such as yeast also may be present in the *rhizosphere*, one can exclude them from this analysis since direct visualization of red color is an endpoint.

One can first verify that the target organisms lack red color. Recombinant *P. agglomerans* can serve as the donor organism at a total CFU count of $10^{12}$ bacteria/reaction in liquid culture. Recipient bacteria can be co-incubated at 22° C. at equal CFU count for time points of 24 hours, 48 hours, 96 hours, or 168 hours. Cultures for ampicillin-resistant recipient bacteria can be done on selective agar and number of recombinant events can be scored. Identity of recombinant bacteria can be determined as above using 16S RNA-specific primers for PCR and compared to direct visualization for color.

Both invasion of the *rhizosphere* by recombinant *P. agglomerans* and HGT between recombinant *P. agglomerans* and consortium members may be observed. Indeed, the large numbers of recombinant *P. agglomerans* used in these trials, the protracted nature of these experiments, and the favorable conditions for HGT are designed to promote gene spread in the *rhizosphere*. One endpoint is evaluation of accuracy of direct color visualization to determine the extent of *rhizosphere* invasion and HGT in these confined settings.

It is noted that, as used in this specification and the appended claims, the singular forms "a," "an," and "the," include plural referents unless expressly and unequivocally limited to one referent. As used herein, the term "include" and its grammatical variants are intended to be non-limiting, such that recitation of items in a list is not to the exclusion of other like items that can be substituted or other items that can be added to the listed items.

Upon studying the disclosure, it will be apparent to those skilled in the art that various modifications and variations can be made in the devices and methods of various embodiments of the invention. Other embodiments will be apparent to those skilled in the art from consideration of the specification and practice of the embodiments disclosed herein. It is intended that the specification and examples be considered as examples only. The various embodiments are not necessarily mutually exclusive, as some embodiments can be combined with one or more other embodiments to form new embodiments.

What is claimed is:

1. A method of detecting an analyte comprising:
   providing a sample that comprises the analyte;
   contacting the sample with a polypeptide that comprises:
   a fluorescent domain comprising:
   a monomeric fluorescent polypeptide comprising
   a C-terminus; and
   an N-terminus;
   a first antibody domain covalently linked to the C-terminus of the fluorescent domain, wherein the first antibody domain comprises a variable light chain ($V_L$) or a variable heavy chain ($V_H$); and
   a second antibody domain covalently linked to the N-terminus of the fluorescent domain, wherein the second antibody domain comprises a variable light chain ($V_L$) or a variable heavy chain ($V_H$);
   wherein the N-terminus of first antibody domain and the C-terminus of the second antibody domain are separated by a distance of no less than 30 Å and no more than 40 Å, wherein at least one of the first antibody domain and the second antibody domain specifically binds to the analyte;
   removing unbound polypeptides; and
   detecting a fluorescent signal produced by the polypeptide specifically bound to the analyte, thereby detecting presence of the analyte in the sample.

2. The method of claim 1 further comprising immobilizing at least a portion of the sample on a substrate.

3. The method of claim 1 further comprising:
   contacting at least a portion of the sample with a second polypeptide that comprises:
   a second fluorescent domain comprising:
   a second monomeric fluorescent polypeptide comprising
   a C-terminus; and
   an N-terminus;
   a third antibody domain covalently linked to the C-terminus of the second fluorescent domain, wherein the third antibody domain comprises a variable light chain ($V_L$) or a variable heavy chain ($V_H$); and
   a fourth antibody domain covalently linked to the N-terminus of the second fluorescent domain, wherein the fourth antibody domain comprises a variable light chain ($V_L$) or a variable heavy chain ($V_H$);
   wherein the N-terminus of third antibody domain and the C-terminus of the fourth antibody domain are separated by a distance of no less than 30 Å and no more than 40 Å, wherein at least one of the third antibody domain and the fourth antibody domain specifically binds to a second analyte in the sample;

removing unbound second polypeptide; and detecting fluorescent signal produced by the second polypeptide specifically bound to the second analyte, thereby detecting presence of the second analyte in the sample.

4. The method of claim 1 further comprising quantifying the fluorescent signal.

* * * * *

SEQUENCE LISTING

```
<160> NUMBER OF SEQ ID NOS: 21

<210> SEQ ID NO 1
<211> LENGTH: 1400
<212> TYPE: DNA
<213> ORGANISM: artificial
<220> FEATURE:
```

<223> OTHER INFORMATION: plasmid sequence for VH, VL, and fluorophore of
     B72.3RFP

<400> SEQUENCE: 1

```
ccatggccca ggtgcagctg cagcagagcg atgcggaact ggtgaaaccg ggcgcgagcg      60
tgaaaattag ctgcaaagcg agcggctata cctttaccga tcatgcgatt cattgggcga     120
aacagaaacc ggaacagggc ctggaatgga ttggctatat tagcccgggc aacgatgata     180
ttaaatataa cgaaaaattt aaaggcaaag cgaccctgac cgcggataaa agcagcagca     240
ccgcgtatat gcagctgaac agcctgacca gcgaagatag cgcggtgtat ttttgcaaac     300
gcagctatta tggccattgg ggccaggca ccaccctgac cgtgagcagc ggcggaggcg      360
gatccgagga cgtcatcaag gagttcatgc gcttcaaggt gcgcatggag ggctccgtga     420
acggccacga gttcgagatc gagggcgagg gcgagggccg ccctacgag ggcacccaga      480
ccgccaagct gaaggtgacc aagggcggcc cctgcccctt cgcctgggac atcctgtccc     540
ctcagttcca gtacggctcc aaggcctacg tgaagcaccc cgccgacatc cccgactact     600
tgaagctgtc cttccccgag ggcttcaagt gggagcgcgt gatgaacttc gaggacggcg     660
gcgtggtgac cgtgacccag gactcctccc tgcaggacgg cgagttcatc tacaaggtga     720
agctgcgcgg caccaacttc ccctccgacg gccccgtaat gcagaagaag accatgggct     780
gggaggcctc caccgagcgg atgtacccg aggacgcgc cctgaagggc gagatcaaga      840
tgaggctgaa gctgaaggac ggcggccact acgacgccga ggtcaagacc acctacatgg     900
ccaagaagcc cgtgcagctg cccggcgcct acaagaccga catcaagctg gacatcacct     960
cccacaacga ggactacacc atcgtggaac agtacgagcg cgccgagggc cgcacaggcg    1020
gaggcggatc cgatattcag atgacccaga gcccggcgag cctgagcgtg agcgtgggcg    1080
aaaccgtgac cattacctgc cgcgcgagcg aaaacattta tagcaacctg gcgtggtatc    1140
agcagaaaca gggcaaaagc ccgcagctgc tggtgtatgc ggcgaccaac ctggcggatg    1200
gcgtgccgag ccgctttagc ggcagcggca gcggcaccca gtatagcctg aaaattaaca    1260
gcctgcagag cgaagatttt ggcagctatt attgccagca cttttggggc accccgtata    1320
cctttggcgg cggcacccgc ctggaaatta acgcgcgga tgcggccgca ctcgagcacc    1380
accaccacca ccaccac                                                    1400
```

<210> SEQ ID NO 2
<211> LENGTH: 466
<212> TYPE: PRT
<213> ORGANISM: artificial
<220> FEATURE:
<223> OTHER INFORMATION: amino acid sequence for VH, VL, and fluorophore
     of B72.3RFP
<220> FEATURE:
<221> NAME/KEY: MISC_FEATURE
<222> LOCATION: (1)..(116)
<223> OTHER INFORMATION: VH domain
<220> FEATURE:
<221> NAME/KEY: MISC_FEATURE
<222> LOCATION: (122)..(338)
<223> OTHER INFORMATION: fluorescent mRFP domain
<220> FEATURE:
<221> NAME/KEY: MISC_FEATURE
<222> LOCATION: (344)..(458)
<223> OTHER INFORMATION: VL domain

<400> SEQUENCE: 2

```
Met Ala Gln Val Gln Leu Gln Gln Ser Asp Ala Glu Leu Val Lys Pro
1               5                  10                  15
```

```
Gly Ala Ser Val Lys Ile Ser Cys Lys Ala Ser Gly Tyr Thr Phe Thr
             20                  25                  30

Asp His Ala Ile His Trp Ala Lys Gln Lys Pro Glu Gln Gly Leu Glu
         35                  40                  45

Trp Ile Gly Tyr Ile Ser Pro Gly Asn Asp Asp Ile Lys Tyr Asn Glu
     50                  55                  60

Lys Phe Lys Gly Lys Ala Thr Leu Thr Ala Asp Lys Ser Ser Ser Thr
 65                  70                  75                  80

Ala Tyr Met Gln Leu Asn Ser Leu Thr Ser Glu Asp Ser Ala Val Tyr
                 85                  90                  95

Phe Cys Lys Arg Ser Tyr Tyr Gly His Trp Gly Gln Gly Thr Thr Leu
            100                 105                 110

Thr Val Ser Ser Gly Gly Gly Ser Glu Asp Val Ile Lys Glu Phe
        115                 120                 125

Met Arg Phe Lys Val Arg Met Glu Gly Ser Val Asn Gly His Glu Phe
    130                 135                 140

Glu Ile Glu Gly Glu Gly Glu Gly Arg Pro Tyr Glu Gly Thr Gln Thr
145                 150                 155                 160

Ala Lys Leu Lys Val Thr Lys Gly Gly Pro Leu Pro Phe Ala Trp Asp
                165                 170                 175

Ile Leu Ser Pro Gln Phe Gln Tyr Gly Ser Lys Ala Tyr Val Lys His
            180                 185                 190

Pro Ala Asp Ile Pro Asp Tyr Leu Lys Leu Ser Phe Pro Glu Gly Phe
        195                 200                 205

Lys Trp Glu Arg Val Met Asn Phe Glu Asp Gly Gly Val Val Thr Val
210                 215                 220

Thr Gln Asp Ser Ser Leu Gln Asp Gly Glu Phe Ile Tyr Lys Val Lys
225                 230                 235                 240

Leu Arg Gly Thr Asn Phe Pro Ser Asp Gly Pro Val Met Gln Lys Lys
                245                 250                 255

Thr Met Gly Trp Glu Ala Ser Thr Glu Arg Met Tyr Pro Glu Asp Gly
            260                 265                 270

Ala Leu Lys Gly Glu Ile Lys Met Arg Leu Lys Leu Lys Asp Gly Gly
        275                 280                 285

His Tyr Asp Ala Glu Val Lys Thr Thr Tyr Met Ala Lys Lys Pro Val
290                 295                 300

Gln Leu Pro Gly Ala Tyr Lys Thr Asp Ile Lys Leu Asp Ile Thr Ser
305                 310                 315                 320

His Asn Glu Asp Tyr Thr Ile Val Glu Gln Tyr Glu Arg Ala Glu Gly
                325                 330                 335

Arg Thr Gly Gly Gly Gly Ser Asp Ile Gln Met Thr Gln Ser Pro Ala
            340                 345                 350

Ser Leu Ser Val Ser Val Gly Glu Thr Val Thr Ile Thr Cys Arg Ala
        355                 360                 365

Ser Glu Asn Ile Tyr Ser Asn Leu Ala Trp Tyr Gln Gln Lys Gln Gly
370                 375                 380

Lys Ser Pro Gln Leu Leu Val Tyr Ala Ala Thr Asn Leu Ala Asp Gly
385                 390                 395                 400

Val Pro Ser Arg Phe Ser Gly Ser Gly Ser Gly Thr Gln Tyr Ser Leu
                405                 410                 415

Lys Ile Asn Ser Leu Gln Ser Glu Asp Phe Gly Ser Tyr Tyr Cys Gln
            420                 425                 430

His Phe Trp Gly Thr Pro Tyr Thr Phe Gly Gly Gly Thr Arg Leu Glu
```

```
             435                 440                 445
Ile Lys Arg Ala Asp Ala Ala Ala Leu Glu His His His His His
        450                 455                 460

His His
465

<210> SEQ ID NO 3
<211> LENGTH: 672
<212> TYPE: DNA
<213> ORGANISM: artificial
<220> FEATURE:
<223> OTHER INFORMATION: nucleotide sequence for mRFP1

<400> SEQUENCE: 3
ggatccgagg acgtcatcaa ggagttcatg cgcttcaagg tgcgcatgga gggctccgtg      60
aacggccacg agttcgagat cgagggcgag ggcgagggcc gcccctacga gggcacccag     120
accgccaagc tgaaggtgac caagggcggc cccctgccct tcgcctggga catcctgtcc     180
cctcagttcc agtacggctc caaggcctac gtgaagcacc ccgccgacat ccccgactac     240
ttgaagctgt ccttccccga gggcttcaag tgggagcgcg tgatgaactt cgaggacggc     300
ggcgtggtga ccgtgaccca ggactcctcc ctgcaggacg gcgagttcat ctacaaggtg     360
aagctgcgcg gcaccaactt ccccctccga cggccccgta atgcagaagaa gactatgggc     420 tgggaggcct ccaccgagcg gatgtacccc gaggacggcg ccctgaaggg cgagatcaag     480
atgaggctga agctgaagga cggcggccac tacgacgccg aggtcaagac cacctacatg     540
gccaagaagc ccgtgcagct gcccggcgcc tacaagaccg acatcaagct ggacatcacc     600
tcccacaacg aggactacac catcgtggaa cagtacgagc gcgccgaggg ccgcacaggc     660
ggaggcggat cc                                                         672

<210> SEQ ID NO 4
<211> LENGTH: 224
<212> TYPE: PRT
<213> ORGANISM: artificial
<220> FEATURE:
<223> OTHER INFORMATION: amino acid sequence for mRFP1
<220> FEATURE:
<221> NAME/KEY: MISC_FEATURE
<222> LOCATION: (3)..(219)
<223> OTHER INFORMATION: fluorescent domain

<400> SEQUENCE: 4

Gly Ser Glu Asp Val Ile Lys Glu Phe Met Arg Phe Lys Val Arg Met
1               5                   10                  15

Glu Gly Ser Val Asn Gly His Glu Phe Glu Ile Glu Gly Glu Gly Glu
            20                  25                  30

Gly Arg Pro Tyr Glu Gly Thr Gln Thr Ala Lys Leu Lys Val Thr Lys
        35                  40                  45

Gly Gly Pro Leu Pro Phe Ala Trp Asp Ile Leu Ser Pro Gln Phe Gln
    50                  55                  60

Tyr Gly Ser Lys Ala Tyr Val Lys His Pro Ala Asp Ile Pro Asp Tyr
65                  70                  75                  80

Leu Lys Leu Ser Phe Pro Glu Gly Phe Lys Trp Glu Arg Val Met Asn
                85                  90                  95

Phe Glu Asp Gly Gly Val Val Thr Val Thr Gln Asp Ser Ser Leu Gln
            100                 105                 110

Asp Gly Glu Phe Ile Tyr Lys Val Lys Leu Arg Gly Thr Asn Phe Pro
        115                 120                 125
```

Ser Asp Gly Pro Val Met Gln Lys Lys Thr Met Gly Trp Glu Ala Ser
             130                 135                 140

Thr Glu Arg Met Tyr Pro Glu Asp Gly Ala Leu Lys Gly Glu Ile Lys
145                 150                 155                 160

Met Arg Leu Lys Leu Lys Asp Gly Gly His Tyr Asp Ala Glu Val Lys
                165                 170                 175

Thr Thr Tyr Met Ala Lys Lys Pro Val Gln Leu Pro Gly Ala Tyr Lys
            180                 185                 190

Thr Asp Ile Lys Leu Asp Ile Thr Ser His Asn Glu Asp Tyr Thr Ile
        195                 200                 205

Val Glu Gln Tyr Glu Arg Ala Glu Gly Arg Thr Gly Gly Gly Ser
    210                 215                 220

<210> SEQ ID NO 5
<211> LENGTH: 720
<212> TYPE: DNA
<213> ORGANISM: artificial
<220> FEATURE:
<223> OTHER INFORMATION: nucleotide sequence for mCitrine

<400> SEQUENCE: 5
ggatccgatc cgatggtgag caaaggcgaa gaactgttta ccggcgtggt gccgattctg      60
gtggaactgg atggcgatgt gaacggccat aaatttagcg tgagcggcga aggcgaaggc     120
gatgcgacct atggcaaact gaccctgaaa tttatttgca ccaccggcaa actgccggtg     180
ccgtggccga ccctggtgac cacctttggc tatggcctga tgtgctttgc gcgttatccg     240
gatcacatga aacagcatga ttttttttaaa agcgcgatgc cggaaggcta tgtgcaggaa     300
cgtaccattt ttttttaaaga tgatggcaac tataaaaccc gtgcggaagt gaaatttgaa     360
ggcgataccc tggtgaaccg tattgaactg aaaggcattg attttaaaga agatggcaac     420
attctgggcc ataaactgga atataactat aacagccata acgtgtatat tatggcggat     480
aaacagaaaa acggcattaa agtgaacttt aaaattcgtc ataacattga agatggcagc     540
gtgcagctgg cggatcatta tcagcagaac accccgattg gcgatggccc ggtgctgctg     600
ccggataacc attatctgag ctatcagagc gcgctgagca agatccgaa cgaaaaacgt     660 gatcacatgg tgctgctgga atttgtgacc gcggcgggca ttaccggcgg cggcggatcc     720

<210> SEQ ID NO 6
<211> LENGTH: 240
<212> TYPE: PRT
<213> ORGANISM: artificial
<220> FEATURE:
<223> OTHER INFORMATION: amino acid sequence for mCitrine
<220> FEATURE:
<221> NAME/KEY: MISC_FEATURE
<222> LOCATION: (3)..(235)
<223> OTHER INFORMATION: fluorescent domain

<400> SEQUENCE: 6

Gly Ser Asp Pro Met Val Ser Lys Gly Glu Glu Leu Phe Thr Gly Val
1               5                   10                  15

Val Pro Ile Leu Val Glu Leu Asp Gly Asp Val Asn Gly His Lys Phe
            20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
    50                  55                  60

```
Leu Val Thr Thr Phe Gly Tyr Gly Leu Met Cys Phe Ala Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Tyr
        195                 200                 205

Gln Ser Ala Leu Ser Lys Asp Pro Asn Glu Lys Arg Asp His Met Val
210                 215                 220

Leu Leu Glu Phe Val Thr Ala Ala Gly Ile Thr Gly Gly Gly Gly Ser
225                 230                 235                 240

<210> SEQ ID NO 7
<211> LENGTH: 720
<212> TYPE: DNA
<213> ORGANISM: artificial
<220> FEATURE:
<223> OTHER INFORMATION: nucleotide sequence for mCerulean

<400> SEQUENCE: 7
ggatccgatc cgatggtgag caaaggcgaa gaactgttta ccggcgtggt gccgattctg      60
gtggaactgg atggcgatgt gaacggccat aaatttagcg tgagcggcga aggcgaaggc     120
gatgcgacct atggcaaact gaccctgaaa tttatttgca ccaccggcaa actgccggtg     180
ccgtggccga ccctggtgac cacccctgacc tggggcgtgc agtgctttgc gcgttatccg     240
gatcacatga acagcatga tttttttaaa agcgcgatgc cggaaggcta tgtgcaggaa      300
cgtaccattt ttttaaaga tgatggcaac tataaaaccc gtgcggaagt gaaatttgaa      360
ggcgatcccc tggtgaaccg tattgaactg aaaggcattg attttaaaga agatggcaac     420
attctgggcc ataaactgga atataacgcg attagcgata cgtgtatat accgcggat      480 aaacagaaaa acggcattaa agcgaacttt aaaattcgtc ataacattga agatggcagc     540
gtgcagctgg cggatcatta tcagcagaac ccccgattg cgatggccc ggtgctgctg      600 ccggataacc attatctgag cacccagagc gcgctgagca agatccgaa cgaaaaacgt     660 gatcacatgg tgctgctgga atttgtgacc gcggcgggca ttaccggcgg cggcggatcc     720

<210> SEQ ID NO 8
<211> LENGTH: 240
<212> TYPE: PRT
<213> ORGANISM: artificial
<220> FEATURE:
<223> OTHER INFORMATION: amino acid sequence for mCerulean
<220> FEATURE:
<221> NAME/KEY: MISC_FEATURE
<222> LOCATION: (3)..(235)
<223> OTHER INFORMATION: fluorescent domain
```

<400> SEQUENCE: 8

```
Gly Ser Asp Pro Met Val Ser Lys Gly Glu Glu Leu Phe Thr Gly Val
1               5                   10                  15

Val Pro Ile Leu Val Glu Leu Asp Gly Asp Val Asn Gly His Lys Phe
            20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
    50                  55                  60

Leu Val Thr Thr Leu Thr Trp Gly Val Gln Cys Phe Ala Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Ala Ile Ser Asp Asn Val Tyr Ile Thr Ala Asp
145                 150                 155                 160

Lys Gln Lys Asn Gly Ile Lys Ala Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr Gly Gly Gly Ser
225                 230                 235                 240
```

<210> SEQ ID NO 9
<211> LENGTH: 44
<212> TYPE: DNA
<213> ORGANISM: artificial
<220> FEATURE:
<223> OTHER INFORMATION: synthetic oligonucleotide primer

<400> SEQUENCE: 9
gtcccttctc gcttctctgg gtccagatct gggacggatt tcac     44

<210> SEQ ID NO 10
<211> LENGTH: 44
<212> TYPE: DNA
<213> ORGANISM: artificial
<220> FEATURE:
<223> OTHER INFORMATION: synthetic oligonucleotide primer

<400> SEQUENCE: 10
gtgaaatccg tcccagatct ggacccagag aagcgagaag ggac     44

<210> SEQ ID NO 11
<211> LENGTH: 39
<212> TYPE: DNA
<213> ORGANISM: artificial
<220> FEATURE:
<223> OTHER INFORMATION: synthetic oligonucleotide primer -continued

<400> SEQUENCE: 11
cagcggcgga ggcggatccg atatccagat gacccagtc                                39

<210> SEQ ID NO 12
<211> LENGTH: 43
<212> TYPE: DNA
<213> ORGANISM: artificial
<220> FEATURE:
<223> OTHER INFORMATION: synthetic oligonucleotide primer

<400> SEQUENCE: 12
tcgagtgcgg ccgcatccgc gcgtttgatc tccaccttgg tac                           43

<210> SEQ ID NO 13
<211> LENGTH: 40
<212> TYPE: DNA
<213> ORGANISM: artificial
<220> FEATURE:
<223> OTHER INFORMATION: synthetic oligonucleotide primer

<400> SEQUENCE: 13
tcggatccgc ctccgcccga ggagacggtg accagggttc                               40

<210> SEQ ID NO 14
<211> LENGTH: 30
<212> TYPE: DNA
<213> ORGANISM: artificial
<220> FEATURE:
<223> OTHER INFORMATION: synthetic oligonucleotide primer

<400> SEQUENCE: 14
taggccatgg ccgaggttca gctggtggag                                          30

<210> SEQ ID NO 15
<211> LENGTH: 31
<212> TYPE: DNA
<213> ORGANISM: artificial
<220> FEATURE:
<223> OTHER INFORMATION: synthetic oligonucleotide primer

<400> SEQUENCE: 15
cagtggatcc gaggacgtca tcaaggagtt c                                        31

<210> SEQ ID NO 16
<211> LENGTH: 44
<212> TYPE: DNA
<213> ORGANISM: artificial
<220> FEATURE:
<223> OTHER INFORMATION: synthetic oligonucleotide primer

<400> SEQUENCE: 16
cagtggatcc gcctccgcct gtgcggccct cggcgcgctc gtac                          44

<210> SEQ ID NO 17
<211> LENGTH: 40
<212> TYPE: DNA
<213> ORGANISM: artificial
<220> FEATURE:
<223> OTHER INFORMATION: synthetic oligonucleotide primer

<400> SEQUENCE: 17
cagtggatcc gccgccgccg gtaatgcccg ccgcggtcac                               40

<210> SEQ ID NO 18
<211> LENGTH: 31

```
<212> TYPE: DNA
<213> ORGANISM: artificial
<220> FEATURE:
<223> OTHER INFORMATION: synthetic oligonucleotide primer

<400> SEQUENCE: 18
cagtggatcc gaggacgtca tcaaggagtt c                              31

<210> SEQ ID NO 19
<211> LENGTH: 44
<212> TYPE: DNA
<213> ORGANISM: artificial
<220> FEATURE:
<223> OTHER INFORMATION: synthetic oligonucleotide primer

<400> SEQUENCE: 19
cagtggatcc gcctccgcct gtgcggccct cggcgcgctc gtac                44

<210> SEQ ID NO 20
<211> LENGTH: 24
<212> TYPE: DNA
<213> ORGANISM: artificial
<220> FEATURE:
<223> OTHER INFORMATION: synthetic oligonucleotide primer

<400> SEQUENCE: 20
gcagctaata cgactcacta tagg                                      24

<210> SEQ ID NO 21
<211> LENGTH: 5
<212> TYPE: PRT
<213> ORGANISM: artificial
<220> FEATURE:
<223> OTHER INFORMATION: exemplary 5 amino acid linker sequence

<400> SEQUENCE: 21

Gly Gly Gly Gly Ser
1               5
```